United States Patent
Samby et al.

(10) Patent No.: US 10,174,035 B2
(45) Date of Patent: Jan. 8, 2019

(54) 6-MORPHOLINYL-2-PYRAZOLYL-9H-PURINE DERIVATIVES AND THEIR USE AS PI3K INHIBITORS

(71) Applicant: Daiichi Sankyo Company, Limited, Chuo-ku, Tokyo (JP)

(72) Inventors: Kirandeep Kaur Samby, Haryana (IN); Yogesh Baban Surase, Maharashtra (IN); Sagar Ramdas Amale, Haryana (IN); Suresh Kumar Gorla, Telangana (IN); Priyanka Patel, Maharastra (IN); Ashwani Kumar Verma, New Delhi (IN)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 15/560,466

(22) PCT Filed: Mar. 29, 2016

(86) PCT No.: PCT/IB2016/051762
§ 371 (c)(1),
(2) Date: Sep. 21, 2017

(87) PCT Pub. No.: WO2016/157074
PCT Pub. Date: Oct. 6, 2016

(65) Prior Publication Data
US 2018/0072732 A1    Mar. 15, 2018

(30) Foreign Application Priority Data
Mar. 30, 2015 (IN) .............................. 878/DEL/2015

(51) Int. Cl.
*C07D 471/04* (2006.01)
*C07D 473/34* (2006.01)
*C07D 519/00* (2006.01)

(52) U.S. Cl.
CPC ......... *C07D 473/34* (2013.01); *C07D 471/04* (2013.01); *C07D 519/00* (2013.01)

(58) Field of Classification Search
CPC ... C07D 471/04; C07D 473/34; C07D 519/00
See application file for complete search history.

(56) References Cited

FOREIGN PATENT DOCUMENTS

WO    2007/127175 A2    11/2007
WO    2010/138589 A1    12/2010

OTHER PUBLICATIONS

Golub et al., Science, vol. 286, Oct. 15, 1999, pp. 531-537.*
Columbian Office Action, dated Nov. 16, 2017, issued in Columbian Application No. NC2017/0011020, 3 pages.
International Search Report and Written Opinion dated Jun. 13, 2016, issued in corresponding International Application No. PCT/IB2016/051762, filed Mar. 29, 2016, 10 pages.
Murray, J.M., et al., "Potent and Highly Selective Benzimidazole Inhibitors of PI3-Kinase Delta," Journal of Medicinal Chemistry 55(17):7686-7695, Sep. 2012.
Safina, B.S., et al., "Identification of GNE-293, a Potent and Selective PI3Kδ Inhibitor: Navigating in vitro Genotoxicity While Improving Potency and Selectivity," Bioorganic & Medicinal Chemistry Letters 23(17):4953-4959, Sep. 2013.

* cited by examiner

*Primary Examiner* — Laura L Stockton
(74) *Attorney, Agent, or Firm* — Christensen O'Connor Johnson Kindness PLLC

(57) ABSTRACT

The present invention relates to a pyrazole derivative of formula (I), a pharmaceutically acceptable salt thereof, a prodrug thereof, a hydrate thereof, stereoisomer thereof or a deuterium form thereof, wherein, n, Y, $R^a$, $R^1$, $R^2$, $R^3$, $R^4$, $R^5$ and $R^6$ are as defined hereinafter in the specification, a pharmaceutical composition comprising a compound of formula (I) as an active ingredient, methods of production, and methods of use thereof.

formula (I)

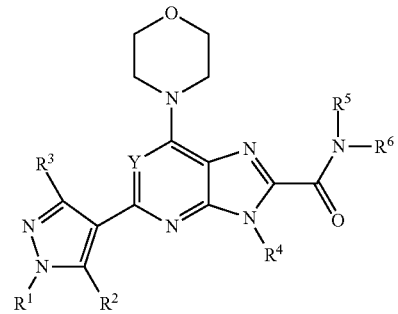

Particularly, the present invention provides a compound of formula (I) as inhibitors of phosphatidylinositol-3-kinase (PI3K), which can be used for treating or preventing inflammatory, autoimmune, orphan and hyperproliferative disease and disorder.

14 Claims, No Drawings

6-MORPHOLINYL-2-PYRAZOLYL-9H-PURINE DERIVATIVES AND THEIR USE AS PI3K INHIBITORS

FIELD OF THE INVENTION

The present invention provides a pyrazole derivative of formula (I), a pharmaceutically acceptable salt thereof, a prodrug thereof, a hydrate thereof, stereoisomer thereof or a deuterium form thereof, wherein, n, Y, $R^a$, $R^1$, $R^2$, $R^3$, $R^4$, $R^5$ and $R^6$ are as defined hereinafter in the specification, a pharmaceutical composition comprising a compound of formula (I) as an active ingredient, methods of production, and methods of use thereof. Particularly, the present invention provides a compound of formula (I) as inhibitors of phosphatidylinositol-3-kinase (PI3K), which can be used for treating or preventing inflammatory, autoimmune, orphan and hyperproliferative disease and disorder.

BACKGROUND OF THE INVENTION

The phosphoinositol-3-kinase (PI3K) family, comprised of lipid kinases, is divided into three different classes: Class I, Class II, and Class III. The classifications are based on primary structure, regulation, and in vitro lipid substrate specificity. Class 1 PI3Ks are most extensively studied and they are activated by cell surface receptors, such as G-protein coupled receptors (GPCRs), growth factors and insulin. Class I PI3Ks are further classified into two subclass, IA and IB. PI3Ks IA enzymes are heterodimers consisting of a catalytic p110 subunit (α, β and δ) and a regulatory subunit (p85, p55, p50). PI3Ks IB enzyme family consists of one member, PI3 kinase γ. PI3K-α is involved in glucose metabolism and insulin signaling, whereas, PI3K-β is involved in platelets activation in thrombotic diseases. In contrast, PI3K-δ and PI3K-γ isoforms are mainly expressed in the hematopoietic systems. Pharmacological and genetic intervention have revealed that PI3K-δ is integral in the orchestration of both the innate and adaptive immune response including expression and activation of inflammatory mediators, inflammatory cell recruitment, airway remodeling and corticosteroid insensitivity in chronic inflammatory airway disease [Rommel C, et al. *Nat. Rev. Lmmunol.* 2007; 7(3):191-201; Medina-Tato D A, et. al. *Immunology.* 2007; 121(4):448-61 and Foster J G et. al. *Pharmacol. Rev.* 2012; 64(4):1027-54].

PI3K has been a validated target being explored by various pharma companies. For example, Idelalisib (Gilead), a PI3Kδ inhibitor, has been launched in 2014 for cancer treatment; however it carries black box warning (hepatotoxicity, severe diarrhea or colitis) and DDI risk (monitoring recommended for steroids; not recommended with salmeterol). GSK-2269557 (GlaxoSmithKline), a PI3Kδ specific inhibitor, has been in phase II for asthma and chronic obstructive pulmonary disease (COPD) as an inhaled product. Duvelisib (Infinity), PI3Kδ/γ dual inhibitor, has been discontinued in January 2015 (Phase II, Inhaled product for asthma and rheumatoid arthritis). PI3K δ/γ K/O mice showed severe impairment of thymocyte development (opportunistic infections). RV-1729 (RespiVert), another PI3Kδ/γ dual inhibitor, has been in phase I for asthma and COPD as an inhaled therapy. AMG-319 (Amgen), TGR-1202/RP-5264 (lncozen/TG therapeutics) and INCB040093 (Incyte) have been at different stages of development for treating lymphoid malignancy.

PI3K inhibitors, preferably PI3Kδ inhibitors have been disclosed in WO2012/082997, WO2012/037226, WO2012/007493, WO2012/107465, WO2011/058027, WO2010/136491, WO2010/138589, WO2010/044401, WO2009/146406, WO2009/045174, WO2009/045175, WO2009/053716 and GB2431156.

Also included herein by references are WO2012/104776, WO2010/005558, WO2010/114494, WO2009/100406, WO2009/034386 WO2008/116129, WO2005/000404 and WO2004035740. However, none of the cited reference disclose pyrazole derivatives as disclosed hereinafter.

Despite significant progress, there is an unmet need and huge opportunity for safe and orally efficacious phosphatidylinositol-3-kinase δ (PI3Kδ) inhibitors for treating and/or preventing inflammatory, autoimmune and hyperproliferative disease or disorder such as allergic asthma, severe asthma, steroid resistant asthma, COPD, psoriasis, psoriatic arthritis, rheumatoid arthritis multiple sclerosis, Systemic lupus erythematous or cancer. As a result of extensive research, the inventors of the present invention have identified safe and orally efficacious PI3Kδ inhibitors that can be used for said purpose.

SUMMARY OF THE INVENTION

Accordingly, the present invention provides a pyrazole derivative of formula (I) or a pharmaceutically acceptable salt thereof, a pharmaceutical composition comprising a compound of formula (I) as an active ingredient, methods of production, and methods of use thereof. Particularly, the present invention provides a compound of formula (I) useful for treating or preventing inflammatory and autoimmune disease or disorder associated with dysregulation of PI3Kδ.

Thus, one aspect of the present invention provides a compound of formula (I)

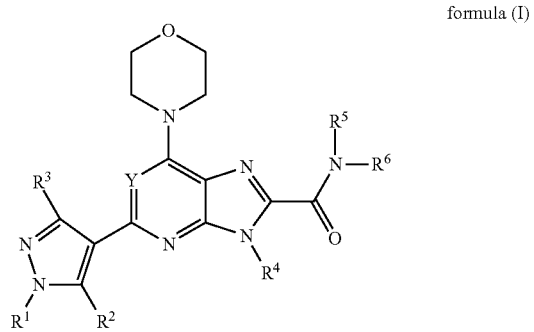

formula (I)

or a pharmaceutically acceptable salt thereof, wherein:

Y represents N, CH, CF, CCl or $CCH_3$;

$R^1$, $R^2$ and $R^3$ independently represent H, alkyl containing 1 to 3 carbon atoms or halogenated alkyl containing 1 to 3 carbon atoms;

$R^4$ and $R^5$ independently represent H or optionally substituted alkyl containing 1 to 3 carbon atoms;

$R^6$ represents alkyl, cycloalkyl or heterocyclyl, wherein alkyl, cycloalkyl and heterocyclyl are optionally substituted; and $R^5$ and $R^6$ are taken together with nitrogen to which they are attached to form optionally substituted heterocyclyl optionally containing one or more heteroatom(s) selected from N, O or S.

Another aspect provides a pharmaceutical composition comprising a compound of formula (I) or a pharmaceutically acceptable salt thereof as its active ingredient and one or more pharmaceutically acceptable excipient(s).

Another aspect provides use of a compound of formula (I) or a pharmaceutically acceptable salt thereof for the manufacture of a medicament for treating or lessening the severity of disease or disorder responsive to the inhibition of PI3Kδ.

Yet another aspect provides a method for treating or lessening the severity of disease or disorder responsive to the inhibition of PI3Kδ in a patient administering to the said patient a therapeutically effective amount of a compound of formula (I), a pharmaceutically acceptable salt thereof, or a pharmaceutical composition thereof.

Yet another aspect provides a compound of formula (1) or a pharmaceutically acceptable salt thereof for use in treating or lessening the severity of disease or disorder responsive to the inhibition of PI3Kδ.

In yet another embodiment, there is provided a medicament for inhibiting PI3Kδ comprising the compound of formula (1) or a pharmaceutically acceptable salt thereof as an active ingredient.

The present invention comprises embodiments as follows [1] to [24] and [1a] to [23a].

[1] The compound of formula (I) or a pharmaceutically acceptable salt thereof, wherein Y represents N.

[2] The compound of formula (I) or a pharmaceutically acceptable salt thereof, wherein Y represents CH, CF, CCl or CCH$_3$.

[3] The compound of formula (I) or a pharmaceutically acceptable salt thereof, wherein R$^1$ and R$^4$ independently represent H, methyl, ethyl, propyl or isopropyl.

[4] The compound of formula (I) or a pharmaceutically acceptable salt thereof, wherein R$^2$ and R$^3$ represent H, methyl or trifluoromethyl.

[5] The compound of formula (I) or a pharmaceutically acceptable salt thereof, wherein R$^5$ represents H, methyl or ethyl, and R$^6$ represents optionally substituted alkyl containing 1 to 6 carbon atoms.

[6] The compound of formula (I) or a pharmaceutically acceptable salt thereof, wherein R$^5$ represents H, methyl or ethyl, and R$^6$ represents optionally substituted 5 to 6 membered cycloalkyl.

[7] The compound of formula (I) or a pharmaceutically acceptable salt thereof, wherein R$^5$ represents H, methyl or ethyl, and R$^6$ represents optionally substituted 5 to 6 membered heterocyclyl.

[8] The compound of formula (I) or a pharmaceutically acceptable salt thereof, wherein R$^5$ and R$^6$ are taken together with nitrogen to which they are attached to form 4-6 membered heterocyclyl, optionally substituted with R$^a$, which is selected from alkyl, aryl, heteroaryl, heterocyclyl, —(CH$_2$)$_p$NR$^b$R$^c$, —NR$^b$COR$^c$, —NR$^c$S(O)$_2$R$^c$, (CH$_2$)$_p$C(O)OR$^d$, —C(O)NR$^b$R$^c$, —C(O)R$^d$, —C(O)OR$^d$, —OR$^d$, wherein alkyl, aryl, heteroaryl and heterocyclyl are optionally substituted; R$^b$, R$^c$, R$^d$ are independently selected from H or optionally substituted alkyl containing 1 to 6 carbon atoms; and p is an integer 0, 1, 2 or 3.

[9] The compound of formula (I) or a pharmaceutically acceptable salt thereof, R$^5$ and R$^6$ are taken together with nitrogen to which they are attached to form 6-membered heterocyclyl, optionally substituted with R$^a$, which is selected from alkyl, aryl, heteroaryl, heterocyclyl, —(CH$_2$)$_p$NR$^b$R$^c$, —NR$^b$COR$^c$, —NR$^b$S(O)$_2$R$^c$, (CH$_2$)$_p$C(O)OR$^d$, —C(O)NR$^b$R$^c$, —C(O)R$^d$, —C(O)OR$^d$, —OR$^d$, wherein alkyl, aryl, heteroaryl and heterocyclyl are optionally substituted; R$^b$, R$^c$, R$^d$ are independently selected from H or alkyl containing 1 to 6 carbon atoms; and p is an integer 0, 1, 2 or 3.

[10] The compound of formula (I) or a pharmaceutically acceptable salt thereof, wherein R$^5$ and R$^6$ are taken together with nitrogen to which they are attached to form spiro ring containing 5-7 carbon atoms, and at least one N or O.

[11] The compound of formula (I) or a pharmaceutically acceptable salt thereof, wherein R$^5$ and R$^6$ are taken together with nitrogen to which they are attached to form fused ring containing 5-7 carbon atoms, and at least one N or O.

[12] The compound of formula (I), which is selected from:

2-(1-Methyl-1H-pyrazol-4-yl)-6-(morpholin-4-yl)-N-[2-(pyridin-3-yl)ethyl]-9H-purine-8-carboxamide (Compound No. 1), 2-(1-Methyl-1H-pyrazol-4-yl)-6-(morpholin-4-yl)-N-[2-(morpholin-4-yl)ethyl]-9H-purine-8-carboxamide (Compound No. 2),

[2-(1-Methyl-1H-pyrazol-4-yl)-6-(morpholin-4-yl)-9H-purin-8-yl](2-oxa-7-azaspiro[3.5]non-7-yl)methanone (Compound No. 3), (3-Hydroxyazetidin-1-yl)[2-(1-methyl-1H-pyrazol-4-yl)-6-(morpholin-4-yl)-9H-purin-8-yl]methanone (Compound No. 4), {4-[cis-2,6-Dimethylmorpholin-4-yl]piperidin-1-yl}[2-(1-methyl-1H-pyrazol-4-yl)-6-(morpholin-4-yl)-9H-purin-8-yl]methanone (Compound No. 5), (9aR)-8-{[2-(1-Methyl-1H-pyrazol-4-yl)-6-(morpholin-4-yl)-9H-purin-8-yl]carbonyl}hexahydropyrazino[2,1-c][1,4]oxazin-4(3H)-one (Compound No. 6), 4-(1-{[2-(1-Methyl-1H-pyrazol-4-yl)-6-(morpholin-4-yl)-9H-purin-8-yl]carbonyl}piperidin-4-yl)morpholin-3-one (Compound No. 7), 2-(4-{[2-(1,3-Dimethyl-1H-pyrazol-4-yl)-6-(morpholin-4-yl)-9H-purin-8-yl]carbonyl}piperazin-1-yl)-2-methylpropanamide (Compound No. 8),

[2-(1,3-Dimethyl-1H-pyrazol-4-yl)-6-(morpholin-4-yl)-9H-purin-8-yl][4-(tetrahydro-2H-pyran-4-yl)piperazin-1-yl]methanone (Compound No. 9), 2-Methyl-2-(4-{[2-(1-methyl-1H-pyrazol-4-yl)-6-(morpholin-4-yl)-9H-purin-8-yl]carbonyl}piperazin-1-yl)propanamide (Compound No. 10),

[2-(1-Methyl-1H-pyrazol-4-yl)-6-(morpholin-4-yl)-9H-purin-8-yl][4-(tetrahydro-2H-pyran-4-yl)piperazin-1-yl]methanone (Compound No. 11),

[2-(1,3-Dimethyl-1H-pyrazol-4-yl)-6-(morpholin-4-yl)-9H-purin-8-yl][4-(2-hydroxypropan-2-yl)piperidin-1-yl]methanone (Compound No. 12),

[2-(1-Methyl-1H-pyrazol-4-yl)-6-(morpholin-4-yl)-9H-purin-8-yl][(3S)-3-(morpholin-4-yl)piperidin-1-yl]methanone (Compound No. 13),

[4-(2-Hydroxypropan-2-yl)piperidin-1-yl][2-(1-methyl-1H-pyrazol-4-yl)-6-(morpholin-4-yl)-9H-purin-8-yl]methanone (Compound No. 14), (1,1-Dioxidothiomorpholin-4-yl)[2-(1-methyl-1H-pyrazol-4-yl)-6-(morpholin-4-yl)-9H-purin-8-yl]methanone (Compound No. 15),

[2-(3,5-Dimethyl-1H-pyrazol-4-yl)-6-(morpholin-4-yl)-9H-purin-8-yl][4-(morpholin-4-yl)piperidin-1-yl]methanone (Compound No. 16), {2-[1-Methyl-3-(trifluoromethyl)-1H-pyrazol-4-yl]-6-(morpholin-4-yl)-9H-purin-8-yl}[4-(morpholin-4-yl)piperidin-1-yl]methanone (Compound No. 17),

[4-(Morpholin-4-yl)piperidin-1-yl]{6-(morpholin-4-yl)-2-[1-(propan-2-yl)-1H-pyrazol-4-yl]-9H-purin-8-yl}methanone (Compound No. 18),

[4-(Morpholin-4-yl)piperidin-1-yl]{6-(morpholin-4-yl)-2-[3-(trifluoromethyl)-1H-pyrazol-4-yl]-9H-purin-8-yl}methanone (Compound No. 19),

[2-(1-Methyl-1H-pyrazol-4-yl)-6-(morpholin-4-yl)-9H-purin-8-yl](piperazin-1-yl)methanone (Compound No. 20),

[4-(Dimethylamino)piperidin-1-yl][9-ethyl-2-(1-methyl-1H-pyrazol-4-yl)-6-(morpholin-4-yl)-9H-purin-8-yl]methanone (Compound No. 21),

[9-Ethyl-2-(1-methyl-1-pyrazol-4-yl)-6-(morpholin-4-yl)-9H-purin-8-yl][4-(morpholin-4-yl)piperidin-1-yl]methanone (Compound No. 22),

[9-Methyl-2-(1-methyl-1H-pyrazol-4-yl)-6-(morpholin-4-yl)-9H-purin-8-yl][4-(morpholin-4-yl)piperidin-1-yl]methanone (Compound No. 23),

[4-(Dimethylamino)piperidin-1-yl][9-methyl-2-(1-methyl-1H-pyrazol-4-yl)-6-(morpholin-4-yl)-9H-purin-8-yl]methanone (Compound No. 24),

[2-(1-Methyl-1H-pyrazol-4-yl)-6-(morpholin-4-yl)-9H-purin-8-yl][4-(pyrimidin-2-ylcarbonyl)piperazin-1-yl]methanone (Compound No. 25), N-(1-{[2-(1-methyl-1H-pyrazol-4-yl)-6-(morpholin-4-yl)-9H-purin-8-yl]carbonyl}piperidin-4-yl)acetamide (Compound No. 26),

[2-(1-Methyl-1H-pyrazol-4-yl)-6-(morpholin-4-yl)-9H-purin-8-yl][4-(pyrimidin-2-yl)piperazin-1-yl]methanone (Compound No. 27), N-(1-{[2-(1-methyl-1H-pyrazol-4-yl)-6-(morpholin-4-yl)-9H-purin-8-yl]carbonyl}piperidin-4-yl)methanesulfonamide (Compound No. 28), 1-(4-{[2-(1-Methyl-1H-pyrazol-4-yl)-6-(morpholin-4-yl)-9H-purin-8-yl]carbonyl}piperazin-1-yl)-2-(pyrazin-2-yl)ethanone (Compound No. 29), 5,6-Dihydroimidazo[1,2-a]pyrazin-7(8H)-yl[2-(1-methyl-1H-pyrazol-4-yl)-6-(morpholin-4-yl)-9H-purin-8-yl]methanone (Compound No. 30), 4-{[2-(1-Methyl-1H-pyrazol-4-yl)-6-(morpholin-4-yl)-9H-purin-8-yl]carbonyl}piperazin-2-one (Compound No. 31),

[2-(1-Methyl-1H-pyrazol-4-yl)-6-(morpholin-4-yl)-9H-purin-8-yl](4-phenylpiperazin-1-yl)methanone (Compound No. 32), N-cyclohexyl-2-(1-methyl-1H-pyrazol-4-yl)-6-(morpholin-4-yl)-9H-purine-8-carboxamide (Compound No. 33),

[2-(1-Methyl-1H-pyrazol-4-yl)-6-(morpholin-4-yl)-9H-purin-8-yl][4-(methylsulfonyl)piperazin-1-yl]methanone (Compound No. 34),

[2-(1-Methyl-1H-pyrazol-4-yl)-6-(morpholin-4-yl)-9H-purin-8-yl](4-phenylpiperidin-1-yl)methanone (Compound No. 35), N-(Cyclohexylmethyl)-2-(1-methyl-1H-pyrazol-4-yl)-6-(morpholin-4-yl)-9H-purine-8-carboxamide (Compound No. 36), N-[(3S)-1-{[2-(1-methyl-1H-pyrazol-4-yl)-6-(morpholin-4-yl)-9H-purin-8-yl]carbonyl}pyrrolidin-3-yl]acetamide (Compound No. 37), N-[(3R)-1-{[2-(1-methyl-1H-pyrazol-4-yl)-6-(morpholin-4-yl)-9H-purin-8-yl]carbonyl}pyrrolidin-3-yl]methanesulfonamide (Compound No. 38), 1-(4-{[2-(1-Methyl-1H-pyrazol-4-yl)-6-(morpholin-4-yl)-9H-purin-8-yl]carbonyl}piperazin-1-yl)ethanone (Compound No. 39),

[2-(1,5-Dimethyl-1H-pyrazol-4-yl)-6-(morpholin-4-yl)-9H-purin-8-yl][4-(morpholin-4-yl)piperidin-1-yl]methanone (Compound No. 40),

[2-(1,3-Dimethyl-1H-pyrazol-4-yl)-6-(morpholin-4-yl)-9H-purin-8-yl][4-(morpholin-4-yl)piperidin-1-yl]methanone (Compound No. 41),

[4-(Morpholin-4-yl)piperidin-1-yl][6-(morpholin-4-yl)-2-(1H-pyrazol-4-yl)-9H-purin-8-yl]methanone (Compound No. 42), Tert-butyl 4-{[2-(1-methyl-1H-pyrazol-4-yl)-6-(morpholin-4-yl)-9H-purin-8-yl]carbonyl}piperazine-1-carboxylate (Compound No. 43),

[(3S)-3-(Dimethylamino)pyrrolidin-1-yl][2-(1-methyl-1H-pyrazol-4-yl)-6-(morpholin-4-yl)-9H-purin-8-yl]methanone (Compound No. 44), Ethyl (4-{[2-(1-methyl-1H-pyrazol-4-yl)-6-(morpholin-4-yl)-9H-purin-8-yl]carbonyl}piperazin-1-yl)acetate (Compound No. 45), (4-Methylpiperazin-1-yl)[2-(1-methyl-1H-pyrazol-4-yl)-6-(morpholin-4-yl)-9H-purin-8-yl]methanone (Compound No. 46), N-(1-Methylpiperidin-4-yl)-2-(1-methyl-1H-pyrazol-4-yl)-6-(morpholin-4-yl)-9H-purine-8-carboxamide (Compound No. 47), N,N-Dimethyl-2-(1-methyl-1H-pyrazol-4-yl)-6-(morpholin-4-yl)-9H-purine-8-carboxamide (Compound No. 48), N-(1-Benzylpiperidin-4-yl)-2-(1-methyl-1H-pyrazol-4-yl)-6-(morpholin-4-yl)-9H-purine-8-carboxamide (Compound No. 49), (1-{[2-(1-Methyl-1H-pyrazol-4-yl)-6-(morpholin-4-yl)-9H-purin-8-yl]carbonyl}piperidin-4-yl)acetic acid (Compound No. 50), Ethyl (1-{[2-(1-methyl-1H-pyrazol-4-yl)-6-(morpholin-4-yl)-9H-purin-8-yl]carbonyl}piperidin-4-yl)acetate (Compound No. 51), N-(2-Methoxyethyl)-2-(1-methyl-1H-pyrazol-4-yl)-6-(morpholin-4-yl)-9H-purine-8-carboxamide (Compound No. 52),

[2-(1-Methyl-1H-pyrazol-4-yl)-6-(morpholin-4-yl)-9H-purin-8-yl](piperidin-1-yl)methanone (Compound No. 53),

[4-(Dimethylamino)piperidin-1-yl][6-(morpholin-4-yl)-2-(1H-pyrazol-4-yl)-9H-purin-8-yl]methanone (Compound No. 54),

[4-(Dimethylamino)piperidin-1-yl][6-(morpholin-4-yl)-2-(1-propyl-1H-pyrazol-4-yl)-9H-purin-8-yl]methanone (Compound No. 55),

[4-(Dimethylamino)piperidin-1-yl][2-(1-ethyl-1H-pyrazol-4-yl)-6-(morpholin-4-yl)-9H-purin-8-yl]methanone (Compound No. 56),

[4-(Dimethylamino)piperidin-1-yl][2-(1-methyl-1H-pyrazol-4-yl)-6-(morpholin-4-yl)-9H-purin-8-yl]methanone (Compound No. 57),

[2-(1-Methyl-1H-pyrazol-4-yl)-6-(morpholin-4-yl)-9H-purin-8-yl][4-(morpholin-4-yl)piperidin-1-yl]methanone (Compound No. 58), N-ethyl-2-(1-methyl-1H-pyrazol-4-yl)-6-(morpholin-4-yl)-N-[2-(morpholin-4-yl)ethyl]-9H-purine-8-carboxamide (Compound No. 59), N-methyl-2-(1-methyl-1H-pyrazol-4-yl)-6-(morpholin-4-yl)-N-[2-(morpholin-4-yl)ethyl]-9H-purine-8-carboxamide (Compound No. 60), 9-Methyl-2-(1-methyl-1H-pyrazol-4-yl)-6-(morpholin-4-yl)-N-[2-(morpholin-4-yl)ethyl]-9H-purine-8-carboxamide (Compound No. 61),

[(3S)-3-Hydroxypyrrolidin-1-yl][2-(1-methyl-1H-pyrazol-4-yl)-6-(morpholin-4-yl)-9H-purin-8-yl]methanone (Compound No. 62), 2-(1-Methyl-1H-pyrazol-4-yl)-6-(morpholin-4-yl)-N-[3-(morpholin-4-yl)propyl]-9H-purine-8-carboxamide (Compound No. 63), 2-(1-Methyl-1H-pyrazol-4-yl)-N-{2-[1-methylpyrrolidin-2-yl]ethyl}-6-(morpholin-4-yl)-9H-purine-8-carboxamide (Compound No. 64), {4-[cis-2,6-Dimethylmorpholin-4-yl]piperidin-1-yl}[6-(morpholin-4-yl)-2-(1H-pyrazol-4-yl)-9H-purin-8-yl]methanone (Compound No. 65),

[2-(3-Methyl-1H-pyrazol-4-yl)-6-(morpholin-4-yl)-9H-purin-8-yl][4-(morpholin-4-yl)piperidin-1-yl]methanone (Compound No. 66), 9-Methyl-2-(1-methyl-1H-pyrazol-4-yl)-6-(morpholin-4-yl)-N-[3-(morpholin-4-yl)propyl]-9H-purine-8-carboxamide (Compound No. 67), 2-(1-Methyl-1H-pyrazol-4-yl)-6-(morpholin-4-yl)-N-[3-(2-oxopyrrolidin-1-yl)propyl]-9H-purine-8-carboxamide (Compound No. 68), N-ethyl-2-(1-methyl-1H-pyrazol-4-yl)-6-(morpholin-4-yl)-N-[3-(morpholin-4-yl)propyl]-9H-purine-8-carboxamide (Compound No. 69), N-[2-(4-methylpiperazin-1-yl)ethyl]-2-(1-methyl-1H-pyrazol-4-yl)-6-(morpholin-4-yl)-9H-purine-8-carboxamide (Compound No. 70), 2-(1,3-Dimethyl-1H-pyrazol-4-yl)-N-{[3-(hydroxymethyl)oxetan-3-yl]methyl}-6-(morpholin-4-yl)-9H-purine-8-carboxamide (Compound No. 71),

[6-(Morpholin-4-yl)-2-(1H-pyrazol-4-yl)-9H-purin-8-yl](2-oxa-7-azaspiro[3.5]non-7-yl)methanone (Compound No. 72), 9-Methyl-2-(1-methyl-1H-pyrazol-4-yl)-6-(morpholin-4-yl)-N-[3-(2-oxopyrrolidin-1-yl)propyl]-9H-purine-8-carboxamide (Compound No. 73), 4-(1-{[6-(Morpholin-4-yl)-2-(1H-pyrazol-4-yl)-9H-purin-8-yl]carbonyl}piperidin-4-yl)morpholin-3-one (Compound No. 74), N-{3-[cis-2,6-dimethylmorpholin-4-yl]propyl}-2-(1-methyl-1H-pyrazol-4-yl)-6-(morpholin-4-yl)-9H-purine-8-carboxamide (Compound No. 75), N-(3-hydroxy-2,2-dimethylpropyl)-2-(1-methyl-1H-pyrazol-4-yl)-6-(morpholin-4-yl)-9H-purine-8-carboxamide (Compound No. 76), 4-(1-{[5-(1-Methyl-1H-pyrazol-4-yl)-7-(morpholin-4-yl)-3H-imidazo[4,5-b]pyridin-2-yl]carbonyl}piperidin-4-yl)morpholin-3-one (Compound No. 77),

[5-(1-Methyl-1H-pyrazol-4-yl)-7-(morpholin-4-yl)-3H-imidazo[4,5-b]pyridin-2-yl](2-oxa-7-azaspiro[3.5]non-7-yl)methanone (Compound No. 78),

[6-Fluoro-5-(1-methyl-1H-pyrazol-4-yl)-7-(morpholin-4-yl)-3H-imidazo[4,5-b]pyridin-2-yl](2-oxa-7-azaspiro[3.5]non-7-yl)methanone (Compound No. 79), (9aR)-8-{[6-Fluoro-5-(1-methyl-1H-pyrazol-4-yl)-7-(morpholin-4-yl)-3H-imidazo[4,5-b]pyridin-2-yl]carbonyl}hexahydropyrazino[2,1-c][1,4]oxazin-4(3H)-one (Compound No. 80),

[6-Fluoro-5-(1-methyl-1H-pyrazol-4-yl)-7-(morpholin-4-yl)-3H-imidazo[4,5-b]pyridin-2-yl][4-(tetrahydro-2H-pyran-4-yl)piperazin-1-yl]methanone (Compound No. 81), 2-(4-{[6-Fluoro-5-(1-methyl-1H-pyrazol-4-yl)-7-(morpholin-4-yl)-3H-imidazo[4,5-b]pyridin-2-yl]carbonyl}piperazin-1-yl)-2-methylpropanamide (Compound No. 82),

[3-(Cyclopropylmethyl)-5-(1,3-dimethyl-1H-pyrazol-4-yl)-6-fluoro-7-(morpholin-4-yl)-3H-imidazo[4,5-b]pyridin-2-yl][4-(morpholin-4-yl)piperidin-1-yl]methanone (Compound No. 83),

[5-(1,3-Dimethyl-1H-pyrazol-4-yl)-6-fluoro-7-(morpholin-4-yl)-3H-imidazo[4,5-b]pyridin-2-yl][4-(2-hydroxypropan-2-yl)piperidin-1-yl]methanone (Compound No. 84), 1-{[5-(1,3-Dimethyl-1H-pyrazol-4-yl)-6-fluoro-7-(morpholin-4-yl)-3H-imidazo[4,5-b]pyridin-2-yl]carbonyl}piperidine-4-carboxamide (Compound No. 85),

[5-(1,3-Dimethyl-1H-pyrazol-4-yl)-6-fluoro-7-(morpholin-4-yl)-3H-imidazo[4,5-b]pyridin-2-yl](4-hydroxypiperidin-1-yl)methanone (Compound No. 86),

[5-(1,3-Dimethyl-1H-pyrazol-4-yl)-6-fluoro-3-methyl-7-(morpholin-4-yl)-3H-imidazo[4,5-b]pyridin-2-yl][4-(morpholin-4-yl)piperidin-1-yl]methanone (Compound No. 87),

[6-Methyl-7-(morpholin-4-yl)-5-(1,3,5-trimethyl-1H-pyrazol-4-yl)-3H-imidazo[4,5-b]pyridin-2-yl][4-(morpholin-4-yl)piperidin-1-yl]methanone (Compound No. 88),

[5-(1,3-Dimethyl-1H-pyrazol-4-yl)-6-methyl-7-(morpholin-4-yl)-3H-imidazo[4,5-b]pyridin-2-yl][4-(morpholin-4-yl)piperidin-1-yl]methanone (Compound No. 89),

[6-Methyl-5-(1-methyl-1H-pyrazol-4-yl)-7-(morpholin-4-yl)-3H-imidazo[4,5-b]pyridin-2-yl][4-(morpholin-4-yl)piperidin-1-yl]methanone (Compound No. 90),

[6-Chloro-5-(1,3-dimethyl-1H-pyrazol-4-yl)-7-(morpholin-4-yl)-3H-imidazo[4,5-b]pyridin-2-yl][4-(morpholin-4-yl)piperidin-1-yl]methanone (Compound No. 91),

[6-Chloro-5-(1-methyl-1H-pyrazol-4-yl)-7-(morpholin-4-yl)-3H-imidazo[4,5-b]pyridin-2-yl][4-(morpholin-4-yl)piperidin-1-yl]methanone (Compound No. 92),

[6-Fluoro-7-(morpholin-4-yl)-5-(1,3,5-trimethyl-1H-pyrazol-4-yl)-3H-imidazo[4,5-b]pyridin-2-yl][4-(morpholin-4-yl)piperidin-1-yl]methanone (Compound No. 93),

[5-(1,3-Dimethyl-1H-pyrazol-4-yl)-7-(morpholin-4-yl)-3H-imidazo[4,5-b]pyridin-2-yl][4-(morpholin-4-yl)piperidin-1-yl]methanone (Compound No. 94),

[5-(1,5-Dimethyl-1H-pyrazol-4-yl)-6-fluoro-7-(morpholin-4-yl)-3H-imidazo[4,5-b]pyridin-2-yl][4-(morpholin-4-yl)piperidin-1-yl]methanone (Compound No. 95),

[5-(1,3-Dimethyl-1H-pyrazol-4-yl)-6-fluoro-7-(morpholin-4-yl)-3H-imidazo[4,5-b]pyridin-2-yl][4-(morpholin-4-yl)piperidin-1-yl]methanone (Compound No. 96),

[4-(Dimethylamino)piperidin-1-yl][5-(1,3-dimethyl-1H-pyrazol-4-yl)-6-fluoro-7-(morpholin-4-yl)-3H-imidazo[4,5-b]pyridin-2-yl]methanone (Compound No. 97),

[6-Fluoro-5-(1-methyl-1H-pyrazol-4-yl)-7-(morpholin-4-yl)-3H-imidazo[4,5-b]pyridin-2-yl][4-(morpholin-4-yl)piperidin-1-yl]methanone (Compound No. 98),

[4-(Dimethylamino)piperidin-1-yl][6-fluoro-5-(1-methyl-1H-pyrazol-4-yl)-7-(morpholin-4-yl)-3H-imidazo[4,5-b]pyridin-2-yl]methanone (Compound No. 99),

[4-(Dimethylamino)piperidin-1-yl][3-methyl-5-(1-methyl-1H-pyrazol-4-yl)-7-(morpholin-4-yl)-3H-imidazo[4,5-b]pyridin-2-yl]methanone (Compound No. 100),

[4-(Dimethylamino)piperidin-1-yl][5-(1-methyl-1H-pyrazol-4-yl)-7-(morpholin-4-yl)-3H-imidazo[4,5-b]pyridin-2-yl]methanone (Compound No. 101),

[5-(1-Methyl-1H-pyrazol-4-yl)-7-(morpholin-4-yl)-3H-imidazo[4,5-b]pyridin-2-yl][4-(morpholin-4-yl)piperidin-1-yl]methanone (Compound No. 102), 5-(1-Methyl-1H-pyrazol-4-yl)-7-(morpholin-4-yl)-N-[2-(morpholin-4-yl)ethyl]-3H-imidazo[4,5-b]pyridine-2-carboxamide (Compound No. 103),

[5-(1,3-Dimethyl-1H-pyrazol-4-yl)-3-methyl-7-(morpholin-4-yl)-3H-imidazo[4,5-b]pyridin-2-yl][4-(morpholin-4-yl)piperidin-1-yl]methanone (Compound No. 104), 6-Fluoro-5-(1-methyl-1H-pyrazol-4-yl)-7-(morpholin-4-yl)-N-[2-(morpholin-4-yl)ethyl]-3H-imidazo[4,5-b]pyridine-2-carboxamide (Compound No. 105),

[3-Methyl-5-(1-methyl-1-pyrazol-4-yl)-7-(morpholin-4-yl)-3H-imidazo[4,5-b]pyridin-2-yl][4-(morpholin-4-yl)piperidin-1-yl]methanone (Compound No. 106),

[5-(1,3-Dimethyl-1H-pyrazol-4-yl)-6-fluoro-3-methyl-7-(morpholin-4-yl)-3H-imidazo[4,5-b]pyridin-2-yl][4-(2-hydroxypropan-2-yl)piperidin-1-yl]methanone (Compound No. 107),

[6-Fluoro-3-methyl-5-(1-methyl-1-pyrazol-4-yl)-7-(morpholin-4-yl)-3H-imidazo[4,5-b]pyridin-2-yl](2-oxa-7-azaspiro[3.5]non-7-yl)methanone (Compound No. 108), {4-[cis-2,6-Dimethylmorpholin-4-yl]piperidin-1-yl}[5-(1-methyl-1H-pyrazol-4-yl)-7-(morpholin-4-yl)-3H-imidazo[4,5-b]pyridin-2-yl]methanone (Compound No. 109), {4-[cis-2,6-Dimethylmorpholin-4-yl]piperidin-1-yl}[3-methyl-5-(1-methyl-1H-pyrazol-4-yl)-7-(morpholin-4-yl)-3H-imidazo[4,5-b]pyridin-2-yl]methanone (Compound No. 110),

[6-Fluoro-3-methyl-5-(1-methyl-1-pyrazol-4-yl)-7-(morpholin-4-yl)-3H-imidazo[4,5-b]pyridin-2-yl][4-(morpholin-4-yl)piperidin-1-yl]methanone (Compound No. 111), {4-[cis-2,6-Dimethylmorpholin-4-yl]piperidin-1-yl}[5-(1,3-dimethyl-1H-pyrazol-4-yl)-6-fluoro-3-methyl-7-(morpholin-4-yl)-3H-imidazo[4,5-b]pyridin-2-yl]methanone (Compound No. 112), {4-[cis-2,6-Dimethylmorpholin-4-yl]piperidin-1-yl}[5-(1,3-dimethyl-1H-pyrazol-4-yl)-7-(morpholin-4-yl)-3H-imidazo[4,5-b]pyridin-2-yl]methanone (Compound No. 113), {4-[cis-2,6-Dimethylmorpholin-4-yl]piperidin-1-yl}[5-(1,3-dimethyl-1H-pyrazol-4-yl)-3-methyl-7-(morpholin-4-yl)-3H-imidazo[4,5-b]pyridin-2-yl]methanone (Compound No. 114), 5-(1-Methyl-1H-pyrazol-4-yl)-7-(morpholin-4-yl)-N-[3-(morpholin-4-yl)propyl]-3H-imidazo[4,5-b]pyridine-2-carboxamide (Compound No. 115), 5-(1-Methyl-1H-pyrazol-4-yl)-7-(morpholin-4-yl)-N-[3-(2-oxopyrrolidin-1-yl)propyl]-3H-imidazo[4,5-b]pyridine-2-carboxamide (Compound No. 116),

[4-(2-Hydroxypropan-2-yl)piperidin-1-yl][5-(1-methyl-1H-pyrazol-4-yl)-7-(morpholin-4-yl)-3H-imidazo[4,5-b]pyridin-2-yl]methanone (Compound No. 117), {4-[cis-2,6-Dimethylmorpholin-4-yl]piperidin-1-yl}[7-(morpholin-4-yl)-5-(1H-pyrazol-4-yl)-3H-imidazo[4,5-b]pyridin-2-yl]methanone (Compound No. 118), {3-[(2R,6S)-2,6-dimethylmorpholin-4-yl]azetidin-1-yl}[5-(1-methyl-1H-pyrazol-4-yl)-7-(morpholin-4-yl)-3H-imidazo[4,5-b]pyridin-2-yl]methanone (Compound No. 119),

[5-(1-Methyl-1H-pyrazol-4-yl)-7-(morpholin-4-yl)-3H-imidazo[4,5-b]pyridin-2-yl][3-(morpholin-4-yl)azetidin-1-yl]methanone (Compound No. 120), N-methyl-5-(1-methyl-1H-pyrazol-4-yl)-7-(morpholin-4-yl)-N-[1-(tetrahydro-2H-pyran-4-yl)piperidin-4-yl]-3H-imidazo[4,5-b]pyridine-2-carboxamide (Compound No. 121), 8-{[2-(1-Methyl-1H-pyrazol-4-yl)-6-(morpholin-4-yl)-9H-purin-8-yl]carbonyl}-2,8-diazaspiro[4.5]decan-3-one (Compound No. 122), {6-Fluoro-7-(morpholin-4-yl)-5-[3-(trifluoromethyl)-1H-pyrazol-4-yl]-3H-imidazo[4,5-b]pyridin-2-yl}[4-(morpholin-4-yl)piperidin-1-yl]methanone (Compound No. 123), 6-Fluoro-5-(1-methyl-1H-pyrazol-4-yl)-7-(morpholin-4-yl)-N-[3-(morpholin-4-yl)propyl]-3H-imidazo[4,5-b]pyridine-2-carboxamide (Compound No. 124),

[6-Fluoro-7-(morpholin-4-yl)-5-(1H-pyrazol-4-yl)-3H-imidazo[4,5-b]pyridin-2-yl][4-(morpholin-4-yl)piperidin-1-yl]methanone (Compound No. 125),

[6-Fluoro-5-(1-methyl-1H-pyrazol-4-yl)-7-(morpholin-4-yl)-3H-imidazo[4,5-b]pyridin-2-yl][3-(morpholin-4-yl)azetidin-1-yl]methanone (Compound No. 126), {3-[(2R,6S)-2,6-dimethylmorpholin-4-yl]azetidin-1-yl}[6-fluoro-5-(1-methyl-1H-pyrazol-4-yl)-7-(morpholin-4-yl)-3H-imidazo[4,5-b]pyridin-2-yl]methanone (Compound No. 127), 4-(1-{[5-(1-Methyl-1H-pyrazol-4-yl)-7-(morpholin-4-yl)-3H-imidazo[4,5-b]pyridin-2-yl]carbonyl}azetidin-3-yl)piperazin-2-one (Compound No. 128), 1-Methyl-4-(1-{[5-(1-methyl-1H-pyrazol-4-yl)-7-(morpholin-4-yl)-3H-imidazo[4,5-b]pyridin-2-yl]carbonyl}azetidin-3-yl)piperazin-2-one (Compound No. 129), 1-Methyl-4-(1-{[2-(1-methyl-1H-pyrazol-4-yl)-6-(morpholin-4-yl)-9H-purin-8-yl]carbonyl}azetidin-3-yl)piperazin-2-one (Compound No. 130), N-Methyl-5-(1-methyl-1H-pyrazol-4-yl)-7-(morpholin-4-yl)-N-[1-(oxetan-3-yl)piperidin-4-yl]-3H-imidazo[4,5-b]pyridine-2-carboxamide (Compound No. 131), N-Methyl-2-(1-methyl-1H-pyrazol-4-yl)-6-(morpholin-4-yl)-N-[1-(oxetan-3-yl)piperidin-4-yl]-9H-purine-8-carboxamide (Compound No. 132),

[4-(Morpholin-4-yl)piperidin-1-yl][7-(morpholin-4-yl)-5-(1H-pyrazol-4-yl)-3H-imidazo[4,5-b]pyridin-2-yl]methanone (Compound No. 133),

[4-(Morpholin-4-yl)piperidin-1-yl]{7-(morpholin-4-yl)-5-[3-(trifluoromethyl)-1H-pyrazol-4-yl]-3H-imidazo[4,5-b]pyridin-2-yl}methanone (Compound No. 134),

[5-(1-Methyl-1H-pyrazol-4-yl)-7-(morpholin-4-yl)-3H-imidazo[4,5-b]pyridin-2-yl][4-(tetrahydro-2H-pyran-4-yl)piperazin-1-yl]methanone (Compound No. 135), or a pharmaceutically acceptable salt thereof.

[13] The compound of formula (I) or a pharmaceutically acceptable salt thereof for use in therapy.

[14] The compound of formula (I) or a pharmaceutically acceptable salt thereof for use in treating autoimmune disease or disorder.

[15] The compound of formula (I) or a pharmaceutically acceptable salt thereof for use in treating inflammatory disease or disorder.

[16] The compound of formula (I) or a pharmaceutically acceptable salt thereof for use in treating hyperproliferative disease or disorder.

[17] The compound of formula (I) or a pharmaceutically acceptable salt thereof for use in treating psoriasis, psoriatic arthritis or rheumatoid arthritis.

[18] The compound of formula (I) or a pharmaceutically acceptable salt thereof for use in treating allergic asthma, severe asthma, steroid resistant asthma or COPD.

[19] The compound of formula (I) or a pharmaceutically acceptable salt thereof for use in treating systemic lupus erythematous, primary immunodeficiency syndrome, tumor or cancer.

[20] The pharmaceutical composition comprising a compound of formula (I) or a pharmaceutically acceptable salt thereof for use in treating allergic asthma.

[21] The pharmaceutical composition comprising a compound of formula (I) or a pharmaceutically acceptable salt thereof for use in treating severe asthma.

[22] The pharmaceutical composition comprising a compound of formula (I) or a pharmaceutically acceptable salt thereof for use in treating steroid resistant asthma.

[23] The pharmaceutical composition comprising a compound of formula (I) or a pharmaceutically acceptable salt thereof for use in treating COPD.

[24] The pharmaceutical composition comprising a compound of formula (I) or a pharmaceutically acceptable salt thereof for use in treating rheumatoid arthritis.

[1a] A pyrazole derivative of formula (I) or a pharmaceutically acceptable salt thereof, wherein:
Y represents N, CH, CF, CCl or CCH$_3$;
R$^1$, R$^2$ and R$^3$ independently represent H, alkyl containing 1 to 3 carbon atoms or halogenated alkyl containing 1 to 3 carbon atoms;
R$^4$ and R$^5$ independently represent H or optionally substituted alkyl containing 1 to 3 carbon atoms;
R$^6$ represents alkyl, cycloalkyl or heterocyclyl, wherein alkyl, cycloalkyl and heterocyclyl are optionally substituted; and
R$^5$ and R$^6$ are taken together with nitrogen to which they are attached to form optionally substituted heterocyclyl optionally containing one or more heteroatom(s) selected from N, O or S.

[2a] The compound according to [1a] or a pharmaceutically acceptable salt thereof, wherein
Y represents N, CH, CF, CCl or CCH$_3$;
R$^1$, R$^2$ and R$^3$ independently represent H, a (C$_1$-C$_3$)alkyl group or a halogenated (C$_1$-C$_3$)alkyl group;
R$^4$ represents H or a (C$_1$-C$_3$)alkyl group,
wherein the (C$_1$-C$_3$)alkyl group is optionally substituted with a (C$_3$-C$_6$)cycloalkyl group;
R$^5$ represents H or a (C$_1$-C$_3$)alkyl group;
R$^6$ represents a group having the formula —X—R$^{6a}$,
[wherein X represents a bond or a (C$_1$-C$_3$) alkylenyl group,
R$^{6a}$ represents a (C$_3$-C$_6$)cycloalkyl group, a heteroaryl group or a 4 to 6 membered heterocyclyl group which has optionally 1 to 3 substituents independently selected from the substituent group A],
R$^5$ and R$^6$ are taken together with nitrogen to which they are attached to form a 4 to 6 membered heterocyclyl ring, a spiro or fused ring containing 5-7 carbon atoms, and at least one N or O,
wherein the 4 to 6 membered heterocyclyl ring is optionally substituted with a group having the formula —W—R$^{6b}$
[wherein W represents the group consisting of a bond, a (C$_1$-C$_3$)alkylenyl group, —NH—, —CO—, —(C$_1$-C$_3$)alkylenyl-CO— or —CO—(C$_1$-C$_3$)alkylenyl-,
R$^{6b}$ represents a hydroxy group, a (C$_1$-C$_6$)alkoxy group, an amino group, di(C$_1$-C$_3$)alkyl amino group, a (C$_1$-C$_3$)alkylcarbonyl group, a (C$_1$-C$_3$)alkylsulfonyl group, a heteroaryl group, an aryl group or a 4 to 6 membered heterocyclyl group which optionally has 1 to 3 substituents independently selected from substituent group A],
the substituent group A represents the group consisting of a (C$_1$-C$_3$)alkyl group, an aryl-(C$_1$-C$_3$)alkyl group, an oxo group, a hydroxy-(C$_1$-C$_3$)alkyl group and an oxetanyl group.

[3a] The compound according to [1a] or [2a] or a pharmaceutically acceptable salt thereof, wherein Y represents N.

[4a] The compound according to any one of [1a] to [3a] or a pharmaceutically acceptable salt thereof, wherein Y represents CH, CF, CCl or CCH$_3$.

[5a] The compound according to any one of [1a] to [4a] or a pharmaceutically acceptable salt thereof, wherein R$^1$ represents a methyl group, and R$^2$ and R$^3$ independently represent H or a methyl group.

[6a] The compound according to any one of [1a] to [5a] or a pharmaceutically acceptable salt thereof, wherein R$^4$ represents H or a methyl group,

[7a] The compound according to any one of [1a] to [6a] or a pharmaceutically acceptable salt thereof, wherein R$^5$ and R$^6$ are taken together with nitrogen to which they are attached to form an azetidine ring, a pyrrolidine ring, a piperidine ring or a piperazine ring,
wherein the azetidine ring, the pyrrolidine ring, the piperidine ring and the piperazine ring are optionally substituted with a tetrahydropyranyl group, a morpholinyl group or a 2,6-dimethylmorpholinyl group.

[8a] The compound according to any one of [1a] to [7a] or a pharmaceutically acceptable salt thereof, which is {4-[cis-2,6-Dimethylmorpholin-4-yl]piperidin-1-yl}[2-(1-methyl-1H-pyrazol-4-yl)-6-(morpholin-4-yl)-9H-purin-8-yl]methanone.

[9a] The compound according to any one of [1a] to [7a] or a pharmaceutically acceptable salt thereof, which is [5-(1,3-Dimethyl-1H-pyrazol-4-yl)-6-fluoro-3-methyl-7-(morpholin-4-yl)-3H-imidazo[4,5-b]pyridin-2-yl][4-(morpholin-4-yl)piperidin-1-yl]methanone.

[10a] The compound according to any one of [1a] to [7a] or a pharmaceutically acceptable salt thereof, which is [2-(1-Methyl-1H-pyrazol-4-yl)-6-(morpholin-4-yl)-9H-purin-8-yl][4-(morpholin-4-yl)piperidin-1-yl]methanone.

[11a] The compound according to any one of [1a] to [7a] or a pharmaceutically acceptable salt thereof, which is [5-(1,3-Dimethyl-1H-pyrazol-4-yl)-7-(morpholin-4-yl)-3H-imidazo[4,5-b]pyridin-2-yl][4-(morpholin-4-yl)piperidin-1-yl]methanone.

[12a] The compound according to any one of [1a] to [7a] or a pharmaceutically acceptable salt thereof, which is {4-[cis-2,6-Dimethylmorpholin-4-yl]piperidin-1-yl}[5-(1,3-dimethyl-1H-pyrazol-4-yl)-7-(morpholin-4-yl)-3H-imidazo[4,5-b]pyridin-2-yl]methanone.

[13a] A pharmaceutical composition comprising a compound according to any one of [1a] to [12a] or a pharmaceutically acceptable salt thereof as an active ingredient and one or more pharmaceutically acceptable excipient(s).

[14a] A pharmaceutical composition according to [13a] for treating or lessening the severity of disease or disorder responsive to the inhibition of phosphoinositol-3-kinase δ(PI3Kδ).

[15a] A pharmaceutical composition according to [14a], wherein the disease or the disorder is psoriasis, psoriatic arthritis, rheumatoid arthritis, allergic asthma, severe asthma, steroid resistant asthma, COPD, systemic lupus erythematous, primary immunodeficiency syndrome or cancer.

[16a] Use of a compound according to any one of [1a] to [12a] or a pharmaceutically acceptable salt thereof for the manufacture of a medicament for treating or lessening the severity of disease or disorder responsive to the inhibition of PI3Kδ.

[17a] Use according to [16a], wherein the disease or the disorder is psoriasis, psoriatic arthritis, rheumatoid arthritis, allergic asthma, severe asthma, steroid resistant asthma, COPD, systemic lupus erythematous, primary immunodeficiency syndrome or cancer.

[18a] A method for treating or lessening the severity of disease or disorder responsive to the inhibition of PI3Kδ in a patient administering to the said patient a therapeutically effective amount of a compound according to any one of [1a] to [12a] or a pharmaceutically acceptable salt thereof.

[19a] A method according to [18a], wherein the disease or the disorder is psoriasis, psoriatic arthritis, rheumatoid arthritis, allergic asthma, severe asthma, steroid resistant asthma, COPD, systemic lupus erythematous, primary immunodeficiency syndrome or cancer.

[20a] The compound according to any one of [1a] to [12a] or a pharmaceutically acceptable salt thereof for use in treating or lessening the severity of disease or disorder responsive to the inhibition of PI3Kδ.

[21a] The compound according to [20a] or a pharmaceutically acceptable salt thereof, wherein the disease or the disorder is psoriasis, psoriatic arthritis, rheumatoid arthritis, allergic asthma, severe asthma, steroid resistant asthma, COPD, systemic lupus erythematous, primary immunodeficiency syndrome or cancer.

[22a] A medicament for inhibiting PI3Kδ comprising the compound according to any one of [1a] to [12a] or a pharmaceutically acceptable salt thereof as an active ingredient.

[23a] A medicament according to [22a], wherein the disease or the disorder is psoriasis, psoriatic arthritis, rheumatoid arthritis, allergic asthma, severe asthma, steroid resistant asthma, COPD, systemic lupus erythematous, primary immunodeficiency syndrome or cancer.

The aforementioned aspects and embodiments, and other aspects, objects, features and advantages of the present invention will be apparent from the following detailed description and the appended claims thereof.

DETAILED DESCRIPTION OF THE INVENTION

As used herein the following definitions apply unless clearly indicated otherwise.

It should be understood that unless expressly stated to the contrary, "a compound of general formula (I) or a pharmaceutically acceptable salt thereof" refers to and includes any and all compounds described by formula (I), its embodiments, as well as sub genuses, inclusive of all salts, prodrugs, hydrates, stereoisomers and deuterium forms thereof. It should also be noted that the singular forms "a" "an" and "the" include plural reference unless the context clearly dictates otherwise.

The term "halo" as used herein alone or in combination refers to fluorine, chlorine, bromine, and iodine.

The term "alkyl" as used herein alone or in combination refers to straight or branched chain containing from 1 to 12 carbon atoms. The straight or branched alkyl group is attached at any available point to produce a stable compound. In certain embodiments straight or branched alkyl group contains from 1-6, 1-4 or 1-3 carbon atoms, such as methyl, ethyl, propyl, isopropyl, butyl, t-butyl, and the like. A "substituted alkyl" denotes alkyl that is independently substituted, unless indicated otherwise, with one or more, preferably 1, 2 or 3, more preferably 1 or 2 substituents, attached at any available atom to produce a stable compound, wherein the substituents are selected from, but are not limited to, halo, $OR^d$, —$C(O)NR^bR^c$, optionally substituted cycloalkyl, aryl, heteroaryl or heterocyclyl. A "($C_1$-$C_3$)alkyl group" refers to a liner or branched alkyl group having 1 to 3 carbon atoms. Examples thereof include a methyl group, an ethyl group, a propyl group and an isopropyl group. A "halogenated ($C_1$-$C_3$)alkyl group" means the above-described ($C_1$-$C_3$)alkyl group substituted by one halogen group. Examples thereof include a chloromethyl group, a bromomethyl group, a fluoromethyl group, a 2-chloromethyl group, a 2-bromomethyl group and a 2-fluoromethyl group. A "($C_1$-$C_6$)alkoxy group" refers to a liner or branched alkoxy group having 1 to 6 carbon atoms. Examples thereof include a methoxy group, an ethoxy group, a propoxy group, a butoxy group and a t-butoxy group. A "di($C_1$-$C_3$)alkylamino group" means an amino group substituted by two above-described ($C_1$-$C_3$)alkyl group. Example thereof include a dimethylamino group, a diethylamino group and a diisopropylamino group. A "($C_1$-$C_3$)alkylcarbonyl group" means a carbonyl group substituted by one above-described ($C_1$-$C_3$)alkyl group. Examples thereof include a methylcarbonyl group (acetyl group), an ethyl carbonyl group and a propylcarbonyl group. A "($C_1$-$C_3$)alkylsulfonyl group" means a sulfonyl group substituted by one ($C_1$-$C_3$)alkyl group. Examples thereof include a methylsulfonyl group (methanesulfonyl group), an ethylsulfonyl group and a propylsulfonyl group. A "aryl-($C_1$-$C_3$) alkyl group" means the above-described ($C_1$-$C_3$)alkyl group substituted by one aryl group. Examples thereof include a phenylmethyl group and a 2-phenethyl group. A "hydroxy-($C_1$-$C_3$)alkyl group" means the above-described ($C_1$-$C_3$) alkyl group substituted by one hydroxy group. Examples thereof include a hydroxymethyl group and a 2-hydroxyethyl group.

The term "($C_1$-$C_3$)alkylenyl group" as used herein refers to a straight or branched bivalent alkyl chain. Examples thereof include —$CH_2$—, —$(CH_2)_2$—, —$(CH_2)_3$—, —$CH(CH_3)$— and —$C(CH_3)_2$—.

The term "cycloalkyl" as used herein refers to saturated or unsaturated non-aromatic monocyclic, bicyclic or tricyclic carbon ring systems of 3 to 10, preferably 3 to 8, more preferably 3 to 6 ring members per ring. Examples of cycloalkyl include, but are not limited to, cyclopropyl, cyclobutyl, cyclopentyl, cyclohexyl, adamantly, and the like. A "substituted cycloalkyl" denotes cycloalkyl that is independently substituted, unless indicated otherwise, with one or more, preferably 1, 2 or 3, more preferably 1 or 2 substituents, attached at any available atom to produce a stable compound, wherein the substituents are selected from, but are not limited to, halo or optionally substituted alkyl containing 1 to 3 carbon atoms. A "($C_3$-$C_6$)cycloalkyl group" denotes a cyclopropyl group, a cyclobutyl group, a cyclopentyl group or a cyclohexyl group.

The term "heterocyclyl" as used herein refers to a saturated or unsaturated non-aromatic mono or polycyclic cycloalkyl group in which from 1 to 3 carbon atoms in the ring are replaced by heteroatom selected from oxygen, sulphur or nitrogen. Heterocyclyl is also intended to include oxidized S or N, such as sulfinyl, sulfonyl, and N-oxide of tertiary ring nitrogen. Heterocyclyl is also intended to include compounds, in which a ring carbon may be oxo substituted, i.e., the ring carbon is carbonyl group, such as lactones and lactams. Heterocyclyl is also intended to include fused, bridged and spiro ring system. Preferably, heterocyclyl rings are optionally fused with benzo or 4 to 6 membered heteroaryl or heterocyclyl ring. The point of attachment of the heterocyclyl ring is at a carbon or nitrogen atom such that a stable ring is retained. Examples of heterocyclyl include, but are not limited to, oxiranyl, thiaarnyl, aziridinyl, oxetanyl, thiatanyl, azetidinyl, tetrahydrofuranyl, tetrahydrothiophenyl, pyrrolidinyl, tetrahydropyranyl, pyranyl, tetrahydrothiopyranyl, thiopyranyl, piperidinyl, 1,4-dioxanyl, 1,4-oxathianyl, morpholinyl, thiomorpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazepanyl, 1,4-azaphosphinanyl, 1,4-diazepanyl, 1,2-tetrahydrothiazin-2-yl, 1,3-tetrahydrothiazin-3-yl, tetrahydrothiadiazinyl, 1,2-tetrahydrodiazin-2-yl, 1,3-tetrahydrodiazin-1-yl, tetrahydroazepinyl, chromanyl, chromenyl, isooxazolidinyl, 1,3-oxazolidin-3-yl, isothiazolidinyl, 1,3-thiazolidin-3-yl, 1,2-pyrazolidin-2-yl, 1,3-pyrazolidin-1-yl, 7-oxa-1-aza-spiro[4,4]nonanyl, 3-azabicyclo[3.1.0]hexanyl, indolinyl, dihydroindolinyl, octahydro-1H-indolyl, octahydro-2H-pyrido[1,2-a]pyrazinyl, 3-azabicyclo[4.1.0]heptanyl, 3,4-dihydro-2H-pyranyl, 1,2,3,4-tetrahydropyridinyl, 1,2,5,6-tetrahydropyridinyl, or tetrahydro-1H-benzo[d]azepinyl, etc. A "substituted heterocyclyl" denotes heterocyclyl that is independently substituted, unless indicated otherwise, with one or more, preferably 1, 2 or 3, more preferably 1 or 2 substituents, attached at any available atom to produce a stable compound, wherein the substituents are selected from, but are not limited to, halo, alkyl, aryl, heteroaryl, heterocyclyl, —(CH$_2$)$_p$NR$^b$R$^c$, —NR$^b$COR$^c$, —NR$^b$S(O)$_2$R$^c$, (CH$_2$)$_p$C(O)OR$^d$, —C(O)NR$^b$R$^c$, —C(O)R$^d$, —C(O)OR$^d$, —OR$^d$, wherein alkyl, aryl, heteroaryl and heterocyclyl are optionally substituted; R$^b$, R$^c$, R$^d$ are independently selected from H or optionally substituted alkyl containing 1 to 6 carbon atoms; and p is an integer 0, 1, 2 or 3. A "4 to 6 membered heterocyclyl group" means a saturated non-aromatic mono cycloalkyl group in which from 1 to 3 carbon atoms in the ring are replaced by at least one heteroatom selected from oxygen, sulphur or nitrogen. Examples thereof include an azetidinyl group, a pyrrolidinyl group, a piperidinyl group, a piperazinyl group, an ocxetanyl group, a tetrandrofuranyl group, a tetrahydropyranyl group and a morpholinyl group.

The term "aryl" as used herein alone or in combination refers to monocyclic and polycyclic aromatic hydrocarbon ring systems containing the requisite number of carbon atoms as described above. Representative examples include, but not limited to, phenyl, naphhthyl, etc. A "substituted aryl" denotes aryl that is independently substituted, unless indicated otherwise, with one or more, preferably 1, 2 or 3, more preferably 1 or 2 substituents, attached at any available atom to produce a stable compound, wherein the substituents are selected from, but are not limited to, halo, —NO$_2$, —CN, alkyl, aryl, heteroaryl, heterocyclyl, —(CH$_2$)$_p$NR$^b$R$^c$, —NR$^b$COR$^c$, —NR$^b$S(O)$_2$R$^c$, (CH$_2$)$_p$C(O)OR$^d$, —C(O)NR$^b$R$^c$, —C(O)R$^d$, —C(O)OR$^d$, —OR$^d$, wherein alkyl, aryl, heteroaryl and heterocyclyl are optionally substituted; R$^b$, R$^c$, R$^d$ are independently selected from H or optionally substituted alkyl containing 1 to 6 carbon atoms; and p is an integer 0, 1, 2 or 3.

The term "heteroaryl" as used herein alone or in combination refers to monocyclic or polycyclic aromatic ring systems containing requisite number of carbon atoms, and at least one heteroatom selected from N, O or S. Polycyclic ring systems may contain aromatic portions, while other portions of the ring system may be fully saturated or non-aromatic. Representative examples of heteroaryl include, but are not limited to pyrrolyl, furanyl, thiophenyl, thienyl, pyrazolyl, imidazolyl, isoxazolyl, oxazolyl, isothiazolyl, thiazolyl, 1,2,3-triazolyl, 1,2,4-triazolyl, tetrazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridinyl, pyridazinyl, pyrimidinyl, pyrazinyl, 1,2,3-triazinyl, pyrazolo[3,4-b]pyridinyl, cinnolinyl, pteridinyl, purinyl, 6,7-dihydro-5H-[1]pyrindinyl, benzo[b]thiophenyl, benzoxazolyl, benzothiazolyl, benzoisothiazolyl, benzoisoxazolyl, benzimidazolyl, benzofuranyl, isobenzofuranyl, isoindolyl, indolyl, indolizinyl, indazolyl, isoquinolinyl, quinolinyl, phthalazinyl, quinoxalinyl, quinazolinyl, benzoxazinyl, and the like. A "substituted heteroaryl" denotes heteroaryl that is independently substituted, unless indicated otherwise, with one or more, preferably 1, 2 or 3, more preferably 1 or 2 substituents, attached at any available atom to produce a stable compound, wherein the substituents are selected from, but are not limited to, halo, —NO$_2$, —CN, alkyl, aryl, heteroaryl, heterocyclyl, —(CH$_2$)$_p$NR$^b$R$^c$, —NR$^b$COR$^c$, —NR$^b$S(O)$_2$R$^c$, (CH$_2$)$_p$C(O)OR$^d$, —C(O)NR$^b$R$^c$, —C(O)R$^d$, —C(O)OR$^d$, —OR$^d$, wherein alkyl, aryl, heteroaryl and heterocyclyl are optionally substituted; R$^b$, R$^c$, R$^d$ are independently selected from H or optionally substituted alkyl containing 1 to 6 carbon atoms; and p is an integer 0, 1, 2 or 3.

In one embodiment, the present invention provides a compound of formula (I):

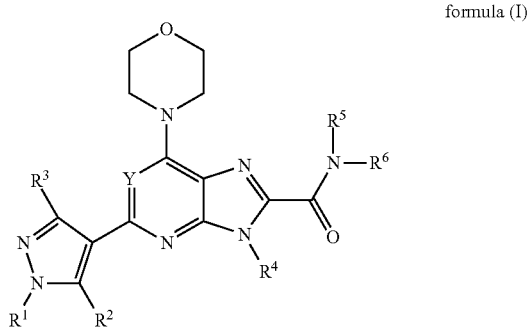

formula (I)

or a pharmaceutically acceptable salt thereof, wherein:
Y represents N;
R$^1$, R$^2$ and R$^3$ independently represent H, alkyl containing 1 to 3 carbon atoms or halogenated alkyl containing 1 to 3 carbon atoms;
R$^4$ and R$^5$ independently represent H or optionally substituted alkyl containing 1 to 3 carbon atoms;
R$^6$ represents alkyl, cycloalkyl or heterocyclyl, wherein alkyl cycloalkyl and heterocyclyl are optionally substituted; and
R$^5$ and R$^6$ are taken together with nitrogen to which they are attached to form optionally substituted heterocyclyl optionally containing one or more heteroatom(s) selected from N, O or S.

Another embodiment provides a compound of formula (I),

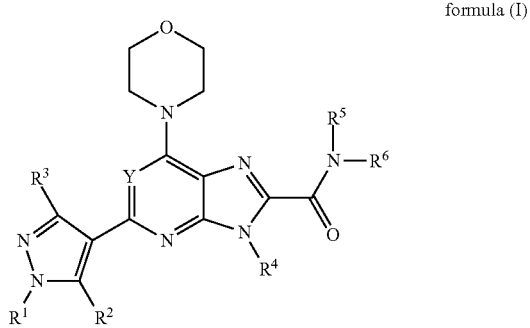

formula (I)

or a pharmaceutically acceptable salt thereof, wherein:
Y represents CH, CCl, CF or CMe;
R$^1$, R$^2$ and R$^3$ independently represent H, alkyl containing 1 to 3 carbon atoms or halogenated alkyl containing 1 to 3 carbon atoms;
R$^4$ and R$^5$ independently represent H or optionally substituted alkyl containing 1 to 3 carbon atoms;
R$^6$ represents alkyl, cycloalkyl or heterocyclyl, wherein alkyl cycloalkyl and heterocyclyl are optionally substituted; and
R$^5$ and R$^6$ are taken together with nitrogen to which they are attached to form optionally substituted heterocyclyl optionally containing one or more heteroatom(s) selected from N, O or S.

Yet another embodiment provides a compound of formula (1),

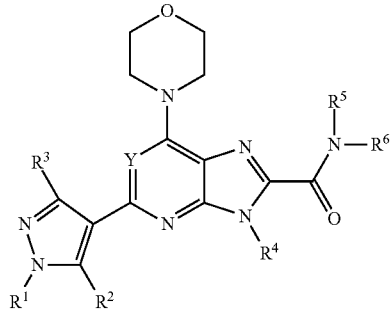

formula (I)

or a pharmaceutically acceptable salt thereof, wherein: Y represents N, CH, CF, CCl or CCH$_3$;
R$^1$, R$^2$ and R$^3$ independently represent H, a (C$_1$-C$_3$)alkyl group or a halogenated (C$_1$-C$_3$)alkyl group;
R$^4$ represents H or a (C$_1$-C$_3$)alkyl group, wherein the (C$_1$-C$_3$)alkyl group is optionally substituted with a (C$_3$-C$_6$) cycloalkyl group;
R$^5$ and R$^6$ are taken together with nitrogen to which they are attached to form an azetidine ring, a pyrrolidine ring, a piperidine ring or a piperazine ring, wherein azetidine ring, pyrrolidine ring, piperidine ring and piperazine ring are optionally substituted with a tetrahydropyranyl group, a morpholinyl group or a 2,6-dimethylmorpholinyl group.

Yet another embodiment provides a compound of formula (I) or a pharmaceutically acceptable salt thereof, wherein R$^5$ represents H, methyl or ethyl, and R$^6$ represents optionally substituted alkyl containing 1 to 6 carbon atoms, optionally substituted 5 to 6 membered cycloalkyl and optionally substituted 4 to 6 membered heterocyclyl, wherein optional substituents are selected from, but are not limited to, halo, —NO$_2$, —CN, alkyl, aryl, heteroaryl, heterocyclyl, —(CH$_2$)$_p$NR$^b$R$^c$, —NR$^b$COR$^c$, —NR$^b$S(O)$_2$R$^c$, (CH$_2$)$_p$C(O)OR$^d$, —C(O)NR$^b$R$^c$, —C(O)R$^d$, —C(O)OR$^d$, —OR$^d$, wherein alkyl, aryl, heteroaryl and heterocyclyl are optionally substituted; R$^b$, R$^c$, R$^d$ are independently selected from H or optionally substituted alkyl containing 1 to 6 carbon atoms; and p is an integer 0, 1, 2 or 3

In a particular embodiment, —NR$^5$R$^6$ is selected from, but not limited to:

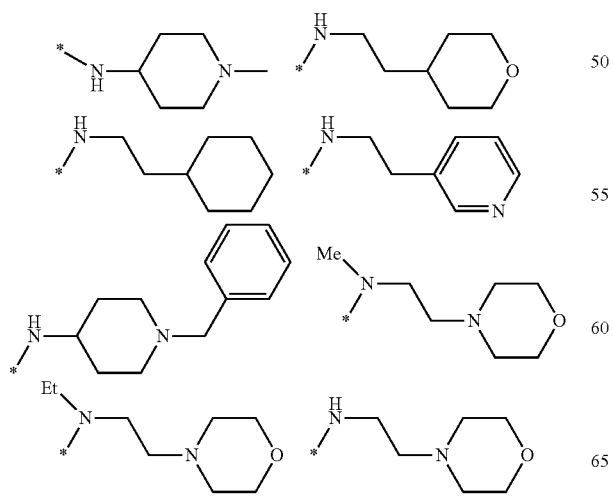

-continued

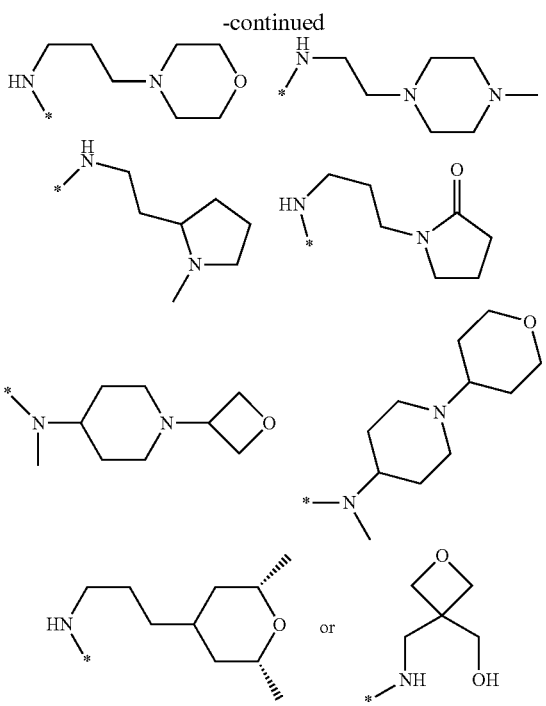

* represents point of attachment.

Another embodiment provides a compound of formula (I) or a pharmaceutically acceptable salt thereof, R$^5$ and R$^6$ are taken together with nitrogen to which they are attached to form 4-6 membered heterocyclyl, optionally substituted with R$^b$, which is selected from alkyl, aryl, heteroaryl, heterocyclyl, —(CH$_2$)$_p$NR$^b$R$^c$, —NR$^b$COR$^c$, —NR$^b$S(O)$_2$R$^c$, (CH$_2$)$_p$C(O)OR$^d$, —C(O)NR$^b$R$^c$, —C(O) R$^d$, —C(O)OR$^d$, —OR$^d$, wherein alkyl, aryl, heteroaryl and heterocyclyl are optionally substituted; R$^b$, R$^c$, R$^d$ are independently selected from H or alkyl containing 1 to 6 carbon atoms; and p is an integer 0, 1, 2 or 3.

In a particular embodiment, —NR$^5$R$^6$ is selected from, but not limited to:

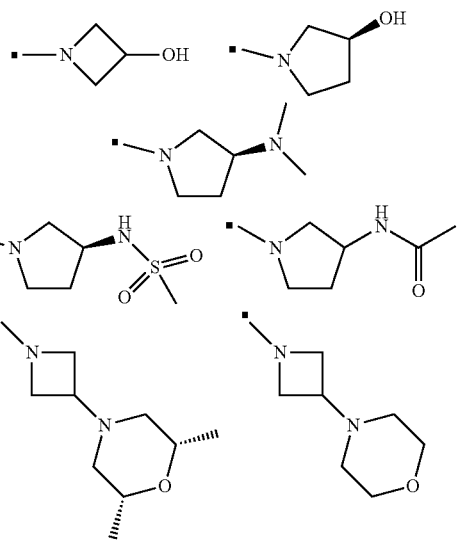

-continued

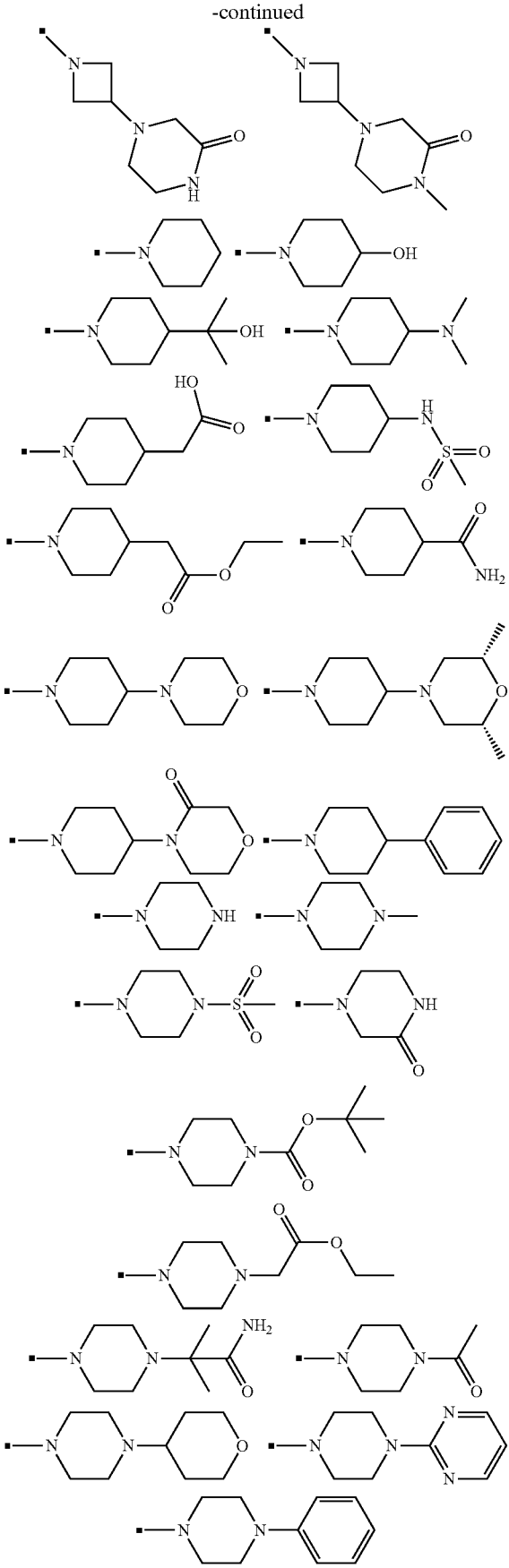

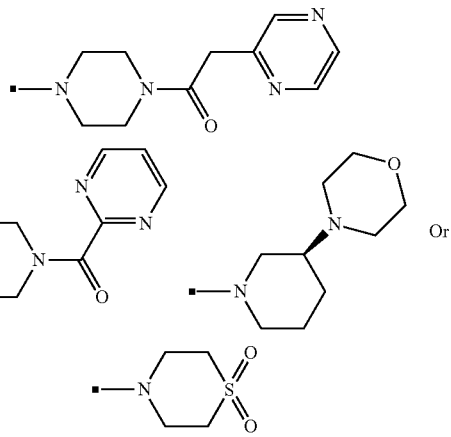

■ represents point of attachment.

Yet another embodiment provides a compound of formula (I) or a pharmaceutically acceptable salt thereof, wherein $R^5$ and $R^6$ are taken together with nitrogen to which they are attached to form spiro or fused ring containing 5-7 carbon atoms, and at least one hetero atom selected from N, S or O, which is exemplified as, but not limited to:

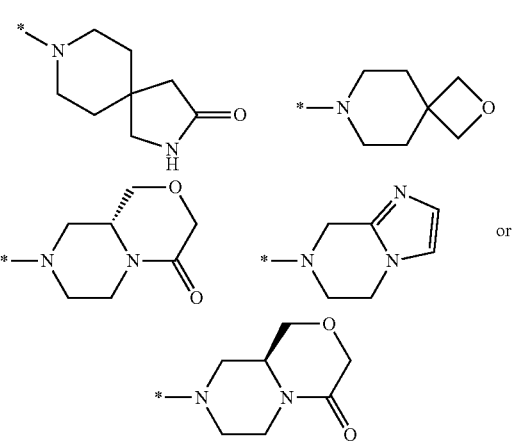

* represents point of attachment.

In a preferred embodiment, —$NR^5R^6$ is selected from:

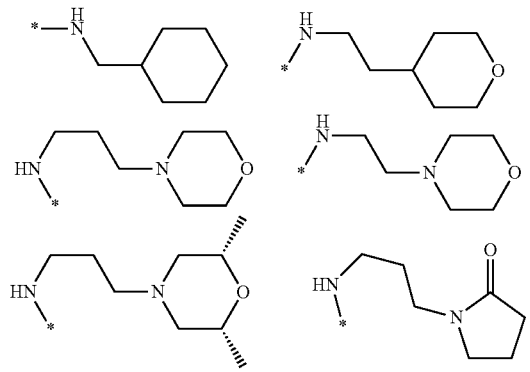

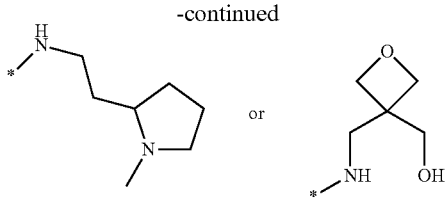

* represents point of attachment.

In another preferred embodiment, —NR⁵R⁶ is selected from:

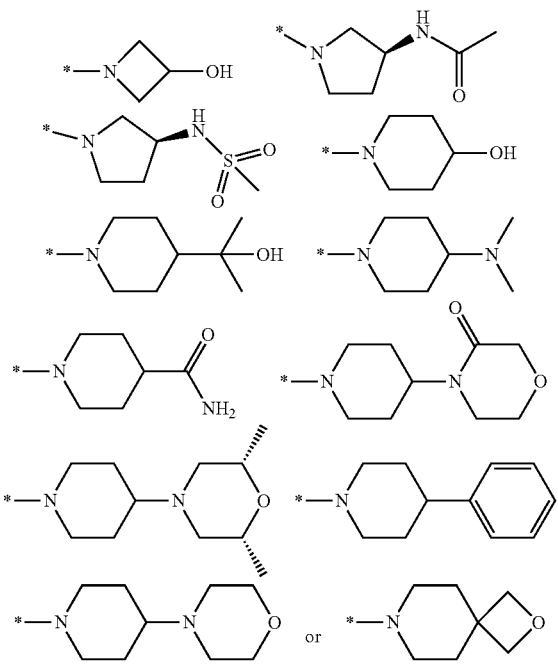

* represents point of attachment.

In yet another preferred embodiment, —NR⁵R⁶ is selected from:

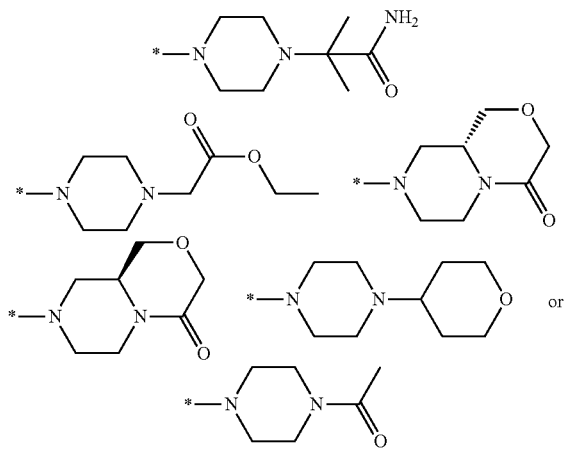

* represents point of attachment.

The compounds of formula (I) and intermediates thereof can be isolated in the form of a pharmaceutically acceptable salt. In the specification, the "pharmaceutically acceptable salt" refers to salts that are chemically and/or physically compatible with other ingredients comprising a formulation, and/or physiologically compatible with the recipient thereof.

Exemplary salts include, but are not limited to: chloride, bromide, iodide, nitrate, sulfate, bisulfate, carbonate, bicarbonate, borate, phosphate, hydrogen phosphate, dihydrogen phosphate, acetate, ascorbate, aspartate, benzoate, besylate, citrate, formate, fumarate, gluconate, glucuronate, glutamate, lactate, malate, maleate, malonate, mesylate, methanesulfonate, ethanesulfonate, benzenesulfonate, p-toluenesulfonate, methylsulphate, nicotinate, oxalate, palmitate, pamoate, stearate, saccharate, succinate, salicylate, tartrate, tosylate, trifluoroacetate; alkali or alkaline earth metal cations such as sodium, lithium, potassium, calcium, magnesium, and the like; ammonium, quaternary ammonium or amine cations such as ammonium, tetramethylammonium, tetraethylammonium, lysine, arginine, benzathine, choline, tromethamine, diolamine, glycine, meglumine, olamine, and the like. Furthermore, the pharmaceutically acceptable salt can have one or more charged atoms and/or one or more counter ions. The salts may exist in different crystalline or polymorphic forms, all of which are intended to be within the scope of the present invention.

The pharmaceutically acceptable salt can be prepared by reacting the compound with a suitable organic or inorganic acid (if the compound is a base) or base (if the compound is an acid) and isolating the salt thus formed. The salts may be precipitated with or without the addition of one or more co-solvents and/or anti-solvents and collected by filtration or the salts may be recovered by evaporation of solvents(s). The pharmaceutically acceptable salt can also be prepared in situ during the isolation and/or purification of a compound.

In the specification, the prodrug refers to a compound that is transformed in vivo to yield the parent compound, wherein the in vivo transformation may occur by various mechanisms such as hydrolysis (gastric acid under the physiological condition) or enzymatic hydrolysis. A prodrug is a compound wherein the amino or hydroxyl group in a compound of formula (I) gets acylated, alkylated, phosphorylated, sulphonated or glycosylated or wherein the carboxyl group is esterified or amidated. A prodrug of a compound of formula (I) may be formed in a conventional manner, for example, if a compound of formula (I) contains a carboxylic acid functional group, a prodrug can be formed by replacement of a hydrogen atom of the acid group with a group such as alkyl or aryl.

In the specification, the hydrate refers to a compound formed by association of one or more water molecules to a compound of formula (I). The water molecule may be bounded or freely available on to the surface of a compound of formula (I). The example includes, but not limited to, monohydrate, dihydrate, trihydrate or tetrahydrate. In certain embodiments, the compound of the present invention can exist in a solvate form, wherein solvate refers to association of solvent molecules with a compound of formula (I).

The compound of formula (I) may contain asymmetric or chiral center(s), and therefore exist in different stereoisomeric form. It is intended that all stereoisomeric forms of the compounds disclosed herein, including but not limited to, diastereomers, enantiomers and atropisomers, as well as mixtures thereof (e.g., racemic mixtures), form part of the present invention. In the specification, R and S are used to denote the absolute configuration of the molecule about its chiral center(s). The compound of formula (I) with asymmetric centers can be synthesized (and/or isolated) as mixtures of enantiomers, individual enantiomers or diastereomers.

The pure enantiomer can be obtained by using methods well known to a person skilled in the art, for example a) by formation of diastereomeric salts which may be separated by crystallization; (b) by formation of diastereomeric derivatives or complexes which may be separated by crystallization, gas-liquid or liquid chromatography; (c) by selective reaction of one enantiomer with an enantiomer specific reagent, for example enzymatic esterification; (d) by using an optically active starting material; (e) by asymmetric synthesis using optically active reagents, substrates, catalysts or solvents; or (f) by converting one stereoisomer into the other by asymmetric transformation or inversion.

The present invention encompasses isotopically labeled compounds of formula (I). All isotopes of any particular atom or element as specified are contemplated within the scope of the present invention. The examples of isotopes that can be incorporated into compounds of the present invention include, but not limited to, isotopes of hydrogen (e.g., $^2$H or $^3$H), carbon (e.g., $^{13}$C or $^{14}$C), nitrogen (e.g., $^{13}$N or $^{15}$N), oxygen (e.g., $^{15}$O, $^{17}$O or $^{18}$O), phosphorous (e.g., $^{32}$P or $^{33}$P), sulphur (e.g., $^{35}$S), halogen (e.g., $^{18}$F, $^{36}$Cl, $^{123}$I or $^{125}$I). In a preferred embodiment, the present invention provides deuterium (D or $^2$H) compounds of the formula (I). Isotopically labeled compounds of formula (I) can be prepared by following the general scheme and methods thereof using isotopically labeled reagents. Isotopically labeled of the present invention may be useful in compound and/or substrate tissue distribution assays. Such applications of isotopically labeled compounds are well known to person skill in the art, and are therefore within the scope of the present invention.

The metabolites of the compound of formula (I) also form a part of the present invention, which refers to the compounds derived from a compound of formula (I) in a cell or organism, preferably mammal. The structure of the metabolites of the compounds can be understood by any person skilled in the art.

The compounds of present invention may be used to treat and/or prevent disease or disorder responsive to the inhibition of PI3Kδ. The literature precedence suggests that orphan disease hyperproliferative, inflammatory and/or autoimmune disease or disorder can be considered when it comes to treatment and/or prevention using such compound.

Accordingly, another object provides a method for treating or lessening the severity of disease or disorder responsive to the inhibition of PI3Kδ in a patient administering to the said patient a therapeutically effective amount of a compound of formula (I), a pharmaceutically acceptable salt thereof, or a pharmaceutical composition thereof.

In the specification, therapeutically effective amount refers to an amount of a compound of formula (I) sufficient to treat or prevent a specific disease or disorder. The amount of a compound which constitutes an effective amount will vary depending on the various factors including for example, the compound being used, the disease state and its severity, the age of the patient to be treated, and the like.

In the specification, patient refers to human and other animal subjects. In this context, the terms "subject", "animal subject", and the like refer to human such as men and women, and non-human vertebrates, for example mammals such as non-human primates, sports and commercial animals, and pets (e.g., canines and felines). Preferably, the patient is human subject.

In the specification, the inflammatory disease refers to inflammation of tissues and organs. The inflammatory diseases or disorders associated with activation of PI3K include, but are not limited to, skin inflammation, skin inflammation due to radiation exposure, allergic asthma, severe asthma, steroid resistant asthma, COPD, allergic inflammation and chronic inflammation.

In the specification, the autoimmune disease refers to a disease which is partially provoked by an immune reaction of the body against own components, for example DNA, lipids, protein, and the like. The autoimmune disease could be organ-specific or non-organ specific. Examples of organic-specific include, but not limited to, insulin-dependent diabetes (Type I), celiac disease, psoriasis, inflammatory bowel disease, chronic active hepatitis, polycystic ovary syndrome, pernicious anemia or ankylosing spondylitis. Examples of non-organ specific include, but not limited to, rheumatoid arthritis, multiple sclerosis, systemic lupus erythmetosus, psoriatic arthritis or myasthenia gravis.

In the specification, the hyperproliferative disease refers to tumor or cancer. The examples include, but not limited to breast cancer, a mantle cell lymphoma, renal cell carcinoma, acute myelogenous leukemia, chronic myelogenous leukemia, rhabdomyosarcoma, ovarian cancer, endometrial cancer, cervical cancer, non-small cell lung carcinoma, small cell lung carcinoma, adenocarcinoma, colon cancer, rectal cancer, gastric carcinoma, hepatocellular carcinoma, melanoma, pancreatic cancer, prostate carcinoma, thyroid carcinoma, anaplastic large cell lymphoma, hemangioma, glioblastoma, solid tumors, lymphoid malignancy or head and neck cancer.

In the specification, orphan disease refers to rare diseases. The examples include, but not limited to, Eosinophilic Gastroenteritis (EGE), and Eosinophilic Gastritis (EG), Eosinophilic Colitis, Hypereosinophilic Syndrome, Eosinophilc Pneumonia, Churg-Strauss Syndrome or mastocytosis.

In certain embodiments, the disease or disorder is selected from, but are not limited to, skin inflammation due to radiation exposure, severe asthma, chronic obstructive pulmonary disease, allergic inflammation, chronic inflammation, allergic disease, rhinitis, sinusitis, food allergy, psoriasis, inflammatory bowel disease, chronic active hepatitis, polycystic ovary syndrome, pernicious anemia, rheumatoid arthritis, multiple sclerosis, systemic lupus erythematous, primary immunodeficiency syndrome (e.g., activated PI3Kδ syndrome), myasthenia gravis or cancer (e.g., breast, ovary, cervix, stomach, lung, melanoma, small cell lung, and the like).

In certain embodiments, the compound of the present invention is more than 50 fold selective in inhibiting PI3Kδ activity over inhibiting PI3Kα, PI3Kβ or PI3Kγ. In one preferred embodiment, the compound of the present invention is more than 100 fold selective in inhibiting PI3Kδ activity over inhibiting PI3Kα, PI3Kβ or PI3Kγ, and even in some cases more than 200 fold. As is evident from the literature that PI3Kδ is integral in the orchestration of both the innate and adaptive immune response including expression and activation of inflammatory mediators, inflammatory cell recruitment, airway remodeling and corticosteroid insensitivity in chronic inflammatory airway disease, hence it can be understood that the compounds of the present invention can preferably be used for the treatment or prevention of inflammatory and/or autoimmune disease or disorder selected from, but not limited to, psoriasis, psoriatic arthritis, rheumatoid arthritis, allergic asthma, severe asthma, steroid resistant asthma or COPD.

In a preferred embodiment, there is provided a method for treating or preventing psoriasis.

In another preferred embodiment, there is provided a method for treating or preventing psoriatic arthritis.

In another preferred embodiment, there is provided a method for treating or preventing rheumatoid arthritis.

In another preferred embodiment, there is provided a method for treating or preventing chronic obstructive pulmonary disease.

In yet another preferred embodiment there is provided a method for treating or preventing allergic asthma.

In yet another preferred embodiment there is provided a method for treating or preventing severe asthma.

Yet another aspect provides a compound of formula (1) or a pharmaceutically acceptable salt thereof for use in treating or lessening the severity of disease or disorder responsive to the inhibition of PI3Kδ.

In yet another embodiment, there is provided a medicament for inhibiting PI3Kδ comprising the compound of formula (1) or a pharmaceutically acceptable salt thereof as an active ingredient.

For therapy a suitable dosage form may be required. Suitable dosage forms will depend upon the use or the route of administration. It should be understood that such dosage forms should allow the compound to reach target cells. Other factors such as toxicity and dosage forms that retard the compound or composition from exerting its effect should also be taken into account. The references for techniques and formulations can be considered, for example, The Science and Practice of Pharmacy, 21st edition, Lippincott, Williams and Wilkins, Philadelphia, Pa., 2005.

Accordingly, another object provides a pharmaceutical composition comprising a compound of formula (I) or a pharmaceutically acceptable salt thereof as its active ingredient and one or more pharmaceutically acceptable excipient(s).

In the specification, excipient refers to any ingredient in the formulation other than the compound of formula (I) or a pharmaceutically acceptable salt thereof. Examples include, but are not limited to, carrier, vehicle, solvent, adjuvant, lubricant, surfactant, binder, buffer, diluent, flavouring agent, coloring agent, disintegrant, emulsifying agent, suspending agent, plasticizer, solubilizer, filler or bulking agent. The choice of excipient(s) will largely depend on factors such as the particular mode of administration, the effect of the excipients on solubility, stability, and release profile, and the nature of the dosage form. The compound of formula (I) or a pharmaceutically acceptable salt thereof may be generally referred to as the active ingredient(s) in a formulation or pharmaceutical composition. A pharmaceutical composition suitable for the delivery of a compound of formula (I) and methods for their preparation will be readily apparent to those skilled in the art. Such compositions and methods for their preparation may be found, for example, in Remington's Pharmaceutical Sciences, 19th ed., (Mack Publishing Company, 1995).

According to the present invention, the preferred administration route is oral, which includes tablet, capsule, pill, powder, sustain or immediate release formulations, solution or suspension. The other preferred administration route may be inhalation. The administration routes such as intravenous, subcutaneous, intramuscular, and the like are also within the scope of the present invention.

The amount of active ingredient(s) and excipient(s) to be present in formulation or pharmaceutical composition can be determined by standard procedures taking into account factors such as the compound $IC_{50}$, the biological half-life of the compound, the age, size, and weight of the patient, and the disease or disorder associated with the patient.

Generally, a dose will be between about 5 mg and 100 mg, bid. Preferably, between 5 mg to 50 mg, bid. More preferably, between 5 mg to 25 mg, bid of the patient being treated. Multiple doses may be used. The person skilled in the art would appreciate that the dose is adjusted in accordance with the methods well known in the therapeutic arts. That is, the maximum tolerable dose can be readily established, and the effective amount providing a detectable therapeutic benefit to the patient may also be determined. Accordingly, while certain dose and administration regimens are exemplified herein, however, these do not in any way limit the dose and administration regimen that may be provided to the patient in practicing the present invention.

In a preferred embodiment, there is provided a pharmaceutical composition comprising a compound of formula (I) or a pharmaceutically acceptable salt thereof for treating or lessening the severity of disease or disorder responsive to the inhibition of PI3Kδ, wherein the disease or disorder is selected from psoriasis, psoriatic arthritis, rheumatoid arthritis, allergic asthma, severe asthma, steroid resistant asthma, COPD, systemic lupus erythematous, primary immunodeficiency syndrome or cancer.

When desired, the compound of formula (I) or a pharmaceutically acceptable salt thereof may be used in combination with one or more β2-agonists, corticosteroids, leukotriene antagonists, anticholinergics, antiallergics, muscarinic receptor antagonists, Treg modulators, checkpoint modulators or anticancer drugs.

In the specification, β2-agonist refers to, but not limited to, albuterol, salbutamol, terbutaline, fenoterol, salmeterol, or formoterol. Corticosteroid refers to, but not limited to, flunisolide, beclomethasone, triamcinolone, budesonide, fluticasone, mometasone, ciclesonide or dexamethasone. Leukotriene antagonist refers to, but not limited to, montelukast, zafirlukast or pranlukast. Anticholinergic refers to, but not limited to, tiotropium bromide, ipratropium bromide or oxitropium bromide. Antiallergic refers to, but not limited to, cetirizine, azelastine, fexofenadine, levocabastine, loratadine, pheniramine, doxylamine, desloratadine or meclizine. Muscarinic receptor antagonists refers to, but not limited to, tolterodine, oxybutynin or atropine. Anticancer refers to, but not limited to, cytotoxic agent (e.g., bendamustine), anti-tumor antibiotic (e.g., bleomycin), microtubule inhibitor (e.g., topotecan), antimetabolite (e.g., methotrexate), DNA linking agent (e.g., cisplatin), biological agent (e.g., imatinib), bisphosphonate (e.g., clodronate) or PI3K inhibitor (e.g., idelalisib).

Next, general schemes and experimental procedures for the preparation of a compound of formula (I) and intermediates thereof will be provided. It should be understood that the procedures set forth below are intended for illustrative purposes and are not to be construed as limiting the scope of the disclosure. Any modification in the procedures described herein, other synthetic procedures and modification thereon can be employed or adapted. All such modifications and alternative procedures are within the spirit and scope of the present application. For the purpose of structural determination of final product and intermediates, the inventors relied on $^1$H NMR, which refers to proton magnetic resonance spectrum and mass spectrum method such as ESI, and various other data such as optical rotation. In the present application, the chemical shift in $^1$H NMR is expressed in ppm (on δ scale) relative to tetramethylsilane as the internal standard, whereas the coupling constant (J) and the peak multiplicity have been referred to as singlet (s); doublet (d);

doublet of doublet (dd); triplet (t); multiplet (m); broad (br), broad singlet (bs), triplet of doublet (td) and quintet (quin). ACD Labs 12.0 (Version 12.5) was used for generating nomenclature of the compounds and intermediates as disclosed herein. Compound of formula (I) is represented by Compound 1 as shown in experimental details below.

EXPERIMENTAL DETAILS

The compound 1 can be produced by various methods known to a person skilled in the art. It should be understood that the present invention is not limited by these examples.

For example, compound 1 (wherein $R^1$ represents H or methyl, $R^2$, $R^3$ and $R^4$ represent H or alkyl) can be produced by amidation of ester compound 1a with an amine compound 1b as shown in Scheme 1.

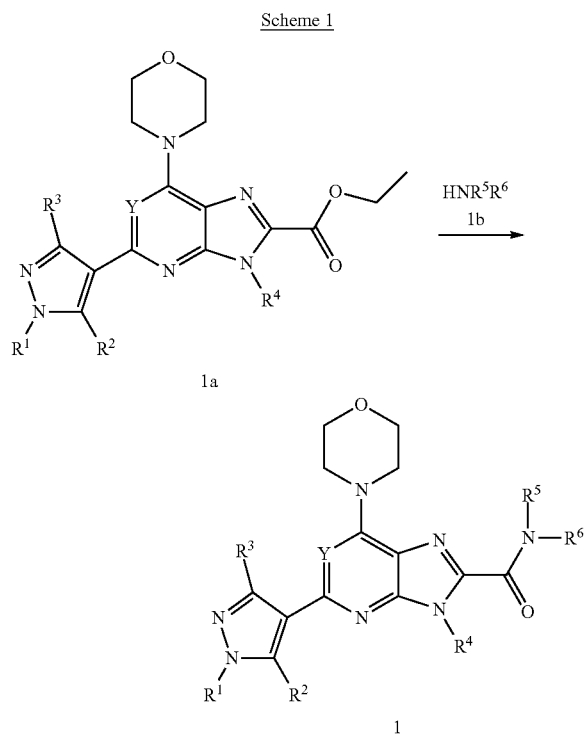

Scheme 1

This reaction can be carried out by method described in Syn. Comm., 1982, 12; Org. Syn., 1979, 59, 49 or by methods equivalent thereto. In certain embodiments, the reaction can be carried out in the presence of aluminium alkyls such as trimethyl aluminium or triisobutyl aluminium in a solvent such as tetrahydrofuran or toluene. The reaction can be carried out at a temperature between 30° C. and 150° C., and preferably between 80° C. and 120° C. More specifically, the reaction was carried out as follows.

Example 1

To a solution of ester compound 1a (1 equiv.) and amine compound 1 b (2 equiv.) in tetrahydrofuran (10 to 100 mL), trimethyl aluminium in toluene (2M, 3 equiv.) was added drop wise at room temperature. After complete addition reaction was vigorously refluxed at about 100° C. for about 18 hours. The reaction mixture was cooled to room temperature, carefully quenched with drop wise addition of methanol, followed by addition of dichloromethane. Water was added and stirred for about 60 minutes. The organic layer was separated. The aqueous layer was extracted using dichloromethane (100 to 300 mL thrice) and the combined organic extracts were dried over anhydrous sodium sulfate and concentrated under vacuum to afford a crude product, which was purified by column chromatography (Combiflash) using methanol and dichloromethane (5 to 15% methanol) as eluent. For example, [2-(1-methyl-1H-pyrazol-4-yl)-6-(morpholin-4-yl)-9H-purin-8-yl](2-oxa-7-azaspiro [3.5]non-7-yl)methanone (Compound No. 3) was prepared using ethyl 2-(1-methyl-1H-pyrazol-4-yl)-6-(morpholin-4-yl)-9H-purine-8-carboxylate (120 mg) and 2-oxa-7-azaspiro [3.5]nonane (122 mg).

$^1$H NMR (400 MHz, DMSO-d6) δ ppm: 13.49 (s, 1H), 8.24 (s, 1H), 7.93 (s, 1H), 4.16-4.40 (m, 8H), 4.02 (brs, 2H), 3.88 (s, 3H), 3.74-3.79 (m, 4H), 3.56-3.64 (m, 2H), 1.86 (d, J=4.27 Hz, 4H). Mass Spectrum (ESI): m/z 438.97 [M+H]

In a similar fashion, compounds listed in Table 1 were prepared using 2-(1-methyl-1H-pyrazol-4-yl)-6-(morpholin-4-yl)-9H-purine-8-carboxylate and amine compound 1b, which is commercially available (Table 1) or synthesized as described hereinafter in this specification.

Alternatively, the ester compound 1a can be converted to the corresponding acid compound by hydrolysis using a base such as lithium hydroxide in a solvent such as tetrahydrofuran, water or combination thereof. The acid compound thus formed can be converted to compound 1 using the procedure known to a person skilled in the art, for example (3-hydroxyazetidin-1-yl)[2-(1-methyl-1H-pyrazol-4-yl)-6-(morpholin-4-yl)-9H-purin-8-yl]methanone (Compound No. 4) was prepared as follows.

Example 2

To a solution of acid compound (200 mg, 0.61 mmole) in dichloromethane (15 mL) was added catalytic amount of dimethylformamide and oxalyl chloride (0.2 mL) at 0° C. Then the reaction mixture was stirred at room temperature for 2-3 hours. The reaction mixture was concentrated under vacuum to dryness and the residue was taken in dichloromethane (10 mL), to it was added triethylamine (0.3 mL) and 3-hydroxy azetidine (200 mg, 1.82 mmole) and was stirred at room temperature for 14 hours. Water was added to the reaction mixture and extracted with dichloromethane (100 mL thrice). The combined organic layer was dried over anhydrous sodium sulfate, concentrated under vacuum. The product was purified by column chromatography using methanol and dichloromethane (10 to 15% methanol) as eluent to obtain 75 mg of desired compound as off white solid.

$^1$H NMR (400 MHz, DMSO-d6) δ ppm: 12.40-14.27 (m, 1H), 8.24 (s, 1H), 7.92 (s, 1H), 5.79 (d, J=6.27 Hz, 1H), 4.76-4.88 (m, 1H), 4.55 (d, J=6.27 Hz, 1H), 4.09-4.48 (m, 6H), 3.88 (s, 3H), 3.79-3.84 (m, 1H), 3.73-3.79 (m, 4H). Mass Spectrum (ESI): m/z 384.89. [M+H]

Similarly [(3S)-3-Hydroxypyrrolidin-1-yl][2-(1-methyl-1H-pyrazol-4-yl)-6-(morpholin-4-yl)-9H-purin-8-yl]methanone (Compound No. 62), (15 mg) was prepared as off white solid.

$^1$H NMR (400 MHz, DMSO-d6) δ ppm: 13.41-13.66 (m, 1H), 8.24 (s, 1H), 7.93 (s, 1H), 4.88-5.08 (m, 1H), 4.09-4.53 (m, 6H), 3.96-4.01 (m, 1H), 3.89 (s, 3H), 3.77 (d, J=4.52 Hz, 4H), 3.47-3.66 (m, 2H), 1.77-2.06 (m, 2H). Mass Spectrum (ESI): m/z 399.18. [M+H]

The compound 1 (wherein $R^4$ represents methyl)) can be prepared by reacting compound 1 (wherein $R^4$ represents H) with alkyl halide such as methyl iodide in presence of a base such as potassium carbonate, sodium carbonate, cesium carbonate in a solvent such as dimethylformamide. More specifically, the reaction was carried out as follows.

Example 3

To a solution of [6-fluoro-7-(morpholin-4-yl)-5-(1-methyl-1H-pyrazol-4-yl)-3H-imidazo[4,5-b]pyridin-2-yl] (2-oxa-7-azaspiro[3.5]non-7-yl)methanone (50 mg, 0.1 mmol) in dimethylformamide (3 mL) were added potassium carbonate (41 mg, 0.27 mmol) followed by methyl iodide (19 mg, 0.13 mmol) and the reaction mixture was stirred at room temperature for 1 hour. To this reaction saturated sodium bicarbonate was added and extracted with dichloromethane (150 mL thrice). The combined organic extracts were dried over anhydrous sodium sulfate, concentrated under vacuum and purified by flash chromatography using methanol and dichloromethane (5% methanol) as eluent to obtain 25 mg of the [6-fluoro-3-methyl-5-(1-methyl-1H-pyrazol-4-yl)-7-(morpholin-4-yl)-3H-imidazo[4,5-b]pyridin-2-yl](2-oxa-7-azaspiro[3.5]non-7-yl)methanone (Compound No. 108).

$^1$H NMR (400 MHz, DMSO-d6) δ ppm: 8.26 (br. s., 1H), 8.00 (br. s., 1H), 4.36 (br. s., 4H), 3.92 (br. s., 4H), 3.79 (br. s., 10H), 3.63 (br. s., 4H), 1.88 (br. s., 4H). Mass Spectrum (ESI): m/z 470.30. [M+H]

In a similar fashion [3-(cyclopropylmethyl)-5-(1,3-dimethyl-1H-pyrazol-4-yl)-6-fluoro-7-(morpholin-4-yl)-3H-imidazo[4,5-b]pyridin-2-yl][4-(morpholin-4-yl)piperidin-1-yl]methanone (Compound No. 83) was prepared using [5-(1,3-dimethyl-1H-pyrazol-4-yl)-6-fluoro-7-(morpholin-4-yl)-3H-imidazo[4,5-b]pyridin-2-yl][4-(morpholin-4-yl) piperidin-1-yl]methanone (200 mg, 0.39 mmol), dimethylformamide (10 mL), potassium carbonate (134 mg, 0.97 mmol) and cyclopropyl methyl bromide (68 mg, 0.50 mmol).

$^1$H NMR (400 MHz, DMSO-d6) δ ppm: 8.06 (s, 1H), 4.49 (d, J=13.64 Hz, 1H), 4.26 (d, J=13.14 Hz, 1H), 4.18 (d, J=7.33 Hz, 1H), 3.78-3.88 (m, 12H), 3.57 (br. s., 6H), 3.19 (t, J=12.00 Hz, 1H), 2.94 (t, J=12.25 Hz, 1H), 2.5 (br.m, 4H), 1.83-1.93 (m, 2H), 1.23 (s, 3H), 0.84-0.92 (m, 2H), 0.47 (d, J=6.82 Hz, 4H). Mass Spectrum (ESI): m/z 567.08. [M+H]

Similarly, the following compounds were prepared.

[5-(1,3-dimethyl-1H-pyrazol-4-yl)-6-fluoro-3-methyl-7-(morpholin-4-yl)-3H-imidazo[4,5-b]pyridin-2-yl][4-(2-hydroxypropan-2-yl)piperidin-1-yl]methanone (Compound No. 107).

$^1$H NMR (400 MHz, DMSO-d6) δ ppm: 8.05 (d, J=4.29 Hz, 1H), 4.57-4.66 (m, 1H), 4.29-4.40 (m, 1H), 4.18 (s, 1H), 3.71-3.90 (m, 14H), 2.99-3.09 (m, 1H), 2.72-2.86 (m, 1H), 2.48-2.54 (s, 3H), 1.82-1.89 (m, 1H), 1.72-1.79 (m, 1H), 1.46-1.58 (m, 1H), 1.15-1.39 (m, 2H), 1.06 (s, 6H). Mass Spectrum (ESI): m/z 500.34. [M+H]

[5-(1,3-Dimethyl-1H-pyrazol-4-yl)-3-methyl-7-(morpholin-4-yl)-3H-imidazo[4,5-b]pyridin-2-yl][4-(morpholin-4-yl)piperidin-1-yl]methanone (Compound No. 104).

$^1$H NMR (400 MHz, DMSO-d6) δ ppm: 8.23 (s, 1H), 6.77 (s, 1H), 4.46-4.52 (m, 1H), 4.22-4.29 (m, 1H), 3.85-3.90 (m, 4H), 3.76-3.81 (m, 11H), 3.51-3.62 (m, 4H), 3.13-3.20 (m, 1H), 2.88-2.95 (m, 1H), 2.45-2.5 (m, 7H), 1.87-1.95 (m, 1H), 1.78-1.85 (m, 1H), 1.38-1.51 (m, 2H). Mass Spectrum (ESI): m/z 509.26. [M+H]

{4-[cis-2,6-dimethylmorpholin-4-yl]piperidin-1-yl}[3-methyl-5-(1-methyl-1H-pyrazol-4-yl)-7-(morpholin-4-yl)-3H-imidazo[4,5-b]pyridin-2-yl]methanone (Compound No. 110).

$^1$H NMR (400 MHz, DMSO-d6) δ ppm: 8.30 (s, 1H), 8.04 (d, J=0.76 Hz, 1H), 6.88 (s, 1H), 4.42-4.62 (m, 1H), 4.16-4.29 (m, 1H), 3.86-3.94 (m, 7H), 3.74-3.82 (m, 7H), 3.47-3.57 (m, 2H), 3.08-3.20 (m, 1H), 2.84-2.97 (m, 1H), 2.70-2.80 (m, 2H), 1.69-2.01 (m, 5H), 1.36-1.52 (m, 2H), 1.04 (dd, J=2.53, 6.32 Hz, 6H). Mass Spectrum (ESI): m/z 523.39. [M+H]

{4-[cis-2,6-Dimethylmorpholin-4-yl]piperidin-1-yl}[5-(1,3-dimethyl-1H-pyrazol-4-yl)-3-methyl-7-(morpholin-4-yl)-3H-imidazo[4,5-b]pyridin-2-yl]methanone (Compound No. 114).

$^1$H NMR (400 MHz, DMSO-d6) δ ppm: 8.24 (s, 1H), 6.77 (s, 1H), 4.43-4.53 (m, 1H), 4.19-4.28 (m, 1H), 3.85-3.90 (m, 4H), 3.75-3.83 (m, 10H), 3.46-3.57 (m, 2H), 3.15 (br. s., 1H), 2.89 (br. s., 1H), 2.74 (d, J=10.54 Hz, 2H), 2.48-2.50 (m, 4H), 1.74-1.94 (m, 4H), 1.35-1.54 (m, 2H), 1.04 (dd, J=2.26, 6.27 Hz, 6H). Mass Spectrum (ESI): m/z 537.44. [M+H]

The compound 1 (wherein $R^1$ represents methyl, $R^2$, $R^3$ and $R^4$ represent H and Y represents N, CH, CF or CCl) can also be prepared by following Scheme 2.

Scheme 2

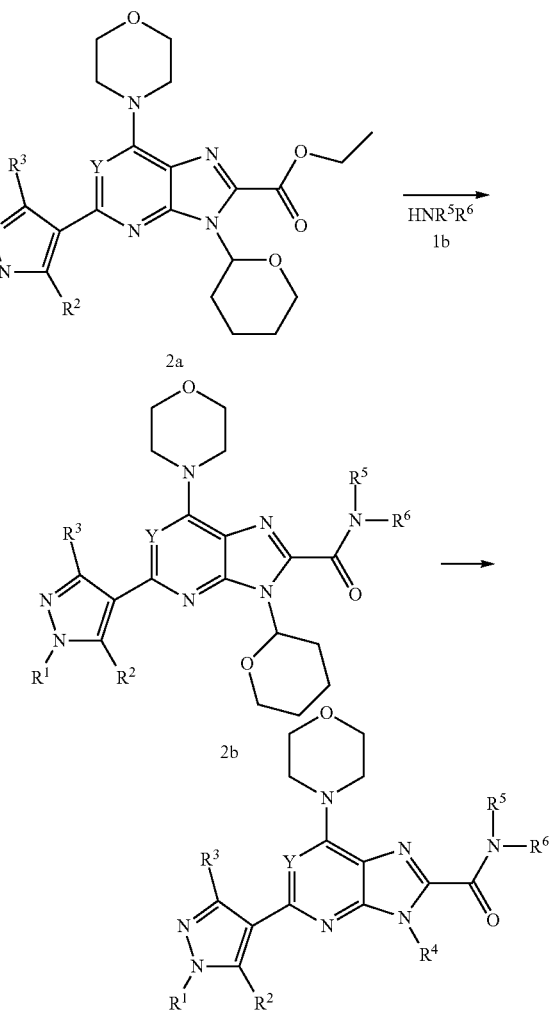

The compound 2b can be prepared via amidation reaction described in Scheme 1, above. Compound 1 can be synthesized by reacting compound 2b with p-toluenesulfonic acid monohydrate (camphorsulphonic acid or catalytic amount of hydrochloric acid can be used) in a suitable solvent such as methanol, ethanol, toluene at a temperature ranging from 50 to 200° C., preferably 70 to 150° C. More specifically, the reaction was carried out as follows.

Example 4

To a solution of a compound 2b (1 equiv.) in ethanol, was added p-toluenesulfonic acid monohydrate (1 equiv.) and refluxed for 14 hours. The reaction mixture was cooled to room temperature, poured over saturated sodium bicarbonate solution and extracted with dichloromethane (250 to 500 mL thrice). The combined organic extracts were dried over anhydrous sodium sulfate and concentrated under vacuum to obtain the crude product, which was then triturated with hexane.

In a similar fashion, 2-(1-methyl-1H-pyrazol-4-yl)-6-(morpholin-4-yl)-N-[2-(pyridin-3-yl)ethyl]-9H-purine-8-carboxamide (Compound No. 1) was prepared using ethyl 2-(1-methyl-1H-pyrazol-4-yl)-6-(morpholin-4-yl)-9-(tetrahydro-2H-pyran-2-yl)-9H-purine-8-carboxylate and 2-(pyridin-3-yl)ethanamine, followed by reaction with p-toluenesulfonic acid monohydrate.

$^1$H NMR (400 MHz, DMSO-d6) δ ppm: 13.61 (s, 1H), 8.77 (s, 1H), 8.37-8.53 (m, 2H), 8.23 (s, 1H), 7.93 (s, 1H), 7.68 (d, J=7.78 Hz, 1H), 7.25-7.39 (m, 1H), 4.29 (br. s., 4H), 3.88 (s, 3H), 3.77 (t, J=4.64 Hz, 4H), 3.55 (d, J=7.03 Hz, 2H), 2.91 (t, J=7.15 Hz, 2H). Mass Spectrum (ESI): m/z 431.10. [M+H]

Similarly compounds listed in Table 1 were prepared using amine compound 1b following the procedure described in Example 4.

Compound 2b (wherein $R^5$ represents alkyl such as methyl or ethyl) can also be prepared by treating compound 2b (wherein $R^5$ is H) with alkyl halide in a suitable solvent such as dimethylformamide. Specifically, the compounds were prepared as follows.

Example 5

To a solution of compound 2b (1 equiv., wherein $R^5$ is H) in dimethylformamide was added sodium hydride (1.5 equiv.) and the reaction mixture was stirred at 0° C. for 30 minutes. Alkyl halide (1.2 equiv., $R^5$I) was added to the reaction mixture, followed by stirring at room temperature for 2 hours. Water was added, extracted with dichloromethane, washed with water, dried over anhydrous sodium sulfate, and concentrated under vacuum to obtain compound 2b (wherein $R^5$ is alkyl), which was purified by column chromatography.

In a similar fashion, N-ethyl-2-(1-methyl-1H-pyrazol-4-yl)-6-(morpholin-4-yl)-N-[2-(morpholin-4-yl)ethyl]-9H-purine-8-carboxamide (Compound No. 59) was prepared using ethyl 2-(1-methyl-1H-pyrazol-4-yl)-6-(morpholin-4-yl)-9-(tetrahydro-2H-pyran-2-yl)-9H-purine-8-carboxylate and 2-(morpholin-4-yl)ethanamine, followed by treatment with ethyl iodide, and p-toluenesulfonic acid monohydrate.

$^1$H NMR (400 MHz, DMSO-d6) δ ppm: 13.46 (br. s., 1H), 8.23 (s, 1H), 7.93 (s, 1H), 4.24 (br. s., 4H), 4.02 (t, J=6.27 Hz, 1H), 3.84-3.93 (m, 4H), 3.75 (t, J=4.02 Hz, 4H), 3.53-3.62 (m, 6H), 2.51-2.59 (m, 1H), 2.45 (br. s., 2H), 2.30 (br. s., 2H), 1.13-1.28 (m, 4H). Mass Spectrum (ESI): m/z 470.20. [M+H]

Similarly the following compounds were prepared.

N-methyl-2-(1-methyl-1H-pyrazol-4-yl)-6-(morpholin-4-yl)-N-[2-(morpholin-4-yl)ethyl]-9H-purine-8-carboxamide (Compound No. 60), $^1$H NMR (400 MHz, DMSO-d6) δ ppm: 13.46 (br. s., 1H), 8.23 (s, 1H), 7.93 (s, 1H), 4.24 (br. s., 4H), 4.02 (t, J=6.27 Hz, 1H), 3.84-3.93 (m, 4H), 3.75 (t, J=4.02 Hz, 4H), 3.53-3.62 (m, 6H), 2.51-2.59 (m, 1H), 2.45 (br. s., 2H), 2.30 (br. s., 2H), 1.13-1.28 (m, 4H). Mass Spectrum (ESI): m/z 456.10 [M+H].

N-ethyl-2-(1-methyl-1H-pyrazol-4-yl)-6-(morpholin-4-yl)-N-[3-(morpholin-4-yl)propyl]-9H-purine-8-carboxamide (Compound No. 69), $^1$H NMR (400 MHz, DMSO-d6) δ ppm: 8.11 (br. s., 1H), 7.99 (br. s., 1H), 4.36 (br. s., 4H), 4.01-4.21 (m, 2H), 3.77-3.99 (m, 8H), 3.72 (br. s., 2H), 3.59 (br. s., 2H), 2.47 (br. s., 6H), 1.82-2.08 (m, 2H), 1.29 (d, J=1.26 Hz, 2H), 1.25 (s, 3H). Mass Spectrum (ESI): m/z 484.30 [M+H].

Compound 1 (wherein Y is CF) can be prepared by following Scheme 2. More specifically, the reaction was carried out as follows.

Example 6

To a solution of compound 2a (1 equiv.) and amine compound 1b (4 equiv.) in tetrahydrofuran (10 to 50 mL) was added trimethyl aluminium (4 equiv.) at 0° C., stirred at room temperature and then refluxed for 24 hours. The reaction mixture was cooled, and partitioned between saturated sodium bicarbonate and dichloromethane (100 to 300 mL thrice). The combined organic extracts were dried over anhydrous sodium sulfate, concentrated under vacuum, and purified by flash chromatography using methanol and dichloromethane (5 to 15% methanol) as eluent to obtain compound 2b. To a solution of compound 2b (1 equiv.) in ethanol (10 to 100 mL) was added para-toluene sulfonic acid (1 equiv.) and the reaction mixture was stirred for 15 minutes at 140° C. under microwave condition. The reaction mixture was partitioned between saturated sodium bicarbonate and dichloromethane (200 to 500 mL). The organic layer was separated, dried over anhydrous sodium sulfate, concentrated under vacuum and purified by flash chromatography using methanol and dichloromethane (5 to 15% methanol; some cases 1% ammonia was used) as eluent.

In a similar fashion, (9aR)-8-{[6-fluoro-5-(1-methyl-1H-pyrazol-4-yl)-7-(morpholin-4-yl)-3H-imidazo[4,5-b]pyridin-2-yl]carbonyl}hexahydropyrazino[2,1-c][1,4]oxazin-4(3H)-one (Compound No. 80) was prepared using methyl 6-fluoro-5-(1-methyl-1H-pyrazol-4-yl)-3-(tetrahydro-2H-pyran-2-yl)-3H-imidazo[4,5-b]pyridine-2-carboxylate (120 mg) and (9aR)-hexahydropyrazino[2,1-c][1,4]oxazin-4(3H)-one (95.21 mg).

1H NMR (400 MHz, DMSO-d6) δ ppm: 13.53 (br. s., 1H), 8.20 (br. s., 1H), 7.93 (br. s., 1H), 5.22-5.42 (m, 1H), 4.50 (d, J=13.05 Hz, 2H), 4.09 (br. s., 2H), 3.92 (s., 3H), 3.92 (m, 1H), 3.81 (d, J=8.53 Hz, 8H), 3.65 (d, J=8.78 Hz, 2H), 3.09-3.28 (m, 1H), 2.74-2.98 (m, 2H). Mass Spectrum (ESI): m/z 484.99. [M+H]

Similarly compounds listed in Table 1 were prepared following the procedure described in Example 6.

The compound 1 (wherein Y represents CH, CF or N) can also be produced by reacting compound 3a with boronate ester 3b as shown in Scheme 3.

Scheme 3

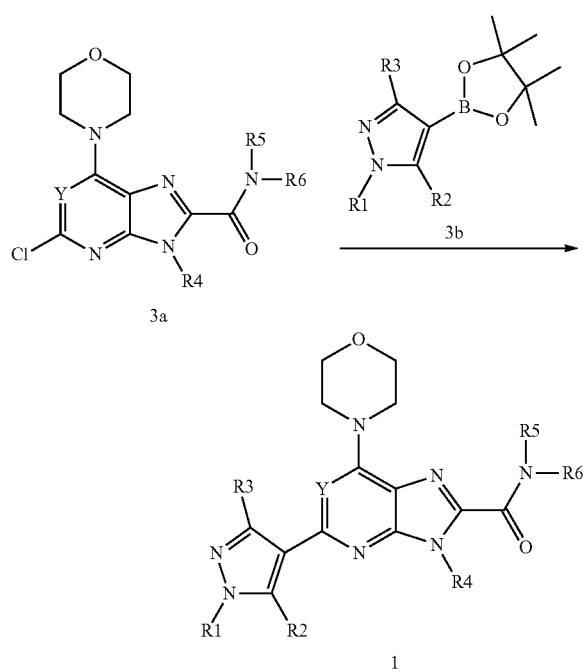

The Suzuki coupling reaction can be carried out following the procedure known to a person skilled in the art. In particular, the reaction can be carried out in the presence of palladium catalyst such as tetrakis(triphenylphosphine)palladium(0) or [1,1'-bis(diphenylphosphino)ferrocene]dichloropalladium(II), base such as potassium carbonate, cesium carbonate, sodium carbonate or sodium bicarbonate, in a solvent such as dichloroethane, dimethylformamide, dimethylsulfoxide, toluene, n-propanol, dioxane, acetonitrile, water or combination thereof. The reaction can be carried out at a temperature between 80 and 150° C., and preferably between 100 and 150° C. More specifically, the reaction was carried out as follows.

Example 7

To a solution of compound 3a (1 equiv.) in 1,2-dichloroethane (10 to 50 mL), were added compound 3b (1.4 equiv.; commercially available, Table 2), cesium carbonate (2.5 equiv.). And purged the reaction mixture using argon for 15 minutes and then tetrakis(triphenylphosphine)palladium (0) (0.1 equiv.) was added. After 15 minutes argon was removed and reaction was allowed to reflux at 110° C. for 4 hours. The reaction mixture was cooled to room temperature; water was added (40 to 250 mL) and extracted using dichloromethane (100 to 500 mL thrice). The combined organic extracts were dried over anhydrous sodium sulfate and concentrated under vacuum to afford crude. The crude product was purified by column chromatography using 50% ethyl acetate in hexane to pure ethyl acetate system. The purest fractions were collected and concentrated under vacuum to afford desired compounds. Alternatively, the reaction was carried out using a compound 3a (1 equiv.), n-propanol and water (9:1, 20 mL), compound 3b (1.3 equiv.), sodium bicarbonate (3 equiv.), tetrakis(triphenylphosphine)palladium(0) (0.1 equiv.) at 140° C. under microwave condition for 1 to 4 hours. Sodium carbonate in acetonitrile and water can also be used.

In a similar fashion, N,N-dimethyl-2-(1-methyl-1H-pyrazol-4-yl)-6-(morpholin-4-yl)-9H-purine-8-carboxamide (Compound No. 48) was prepared by reacting 2-chloro-N,N-dimethyl-6-(morpholin-4-yl)-9H-purine-8-carboxamide (80 mg) and 1-methyl 4-pyrazole boronic acid pinacol ester (85 mg).

$^1$H NMR (400 MHz, DMSO-d6) δ ppm: 13.39-13.59 (m, 1H), 8.21-8.27 (m, 1H), 7.89-7.94 (m, 1H), 4.13-4.38 (m, 4H), 3.88 (s, 3H), 3.76 (d, J=4.27 Hz, 4H), 3.45 (s, 3H), 3.05 (s, 3H). Mass Spectrum (ESI): m/z 357.14 [M+H]

Similarly compounds listed in Table 2 were prepared following the procedure described in Example 7.

The compound 1 (wherein Y represents CF or CCl) can be produced by reacting compound 4a with boronate ester 3b as shown in Scheme 4.

Scheme 4

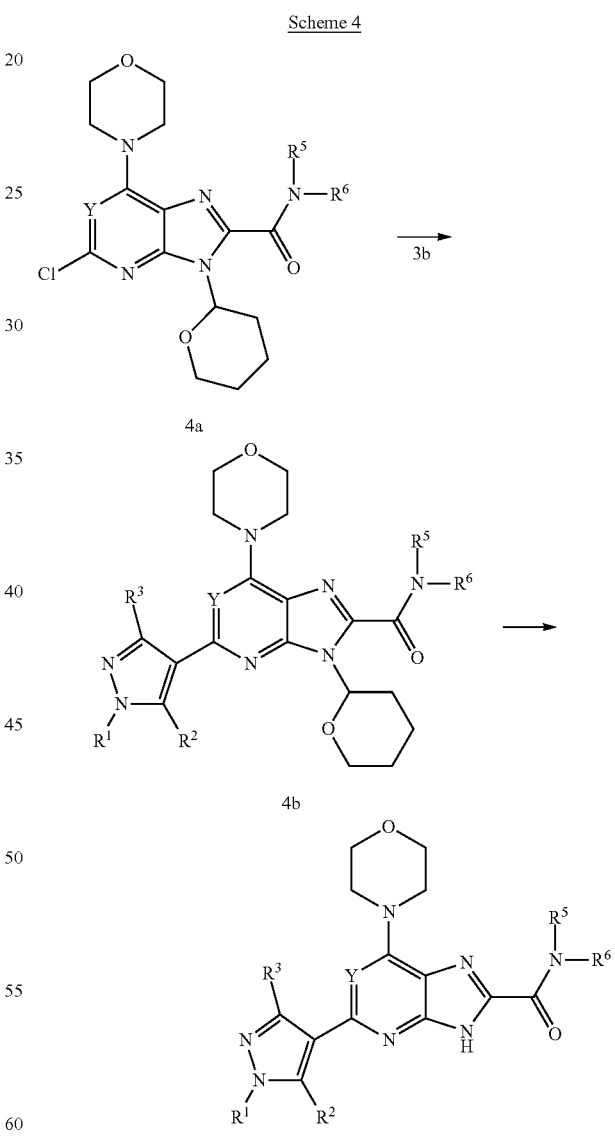

The Suzuki coupling can be carried out following the procedure described in scheme 3 above. The compound 4b can be converted to compound 1 according to the synthetic procedure known to a person skilled in the art, for example the process described in Scheme 2, above. More specifically, the reactions were carried out as follows.

Example 8

To a solution of compound 4a (1 equiv.) in n-propanol and water (9:1, 20 mL), was added boronate ester 3b (1.4 equiv.) and sodium bicarbonate (3 equiv.) and the reaction mixture was purged with Argon for 10 minutes. tetrakis(triphenylphosphine)palladium(0) (0.1 equiv.) was added and the mixture was heated for 1 hour under microwave condition at 140° C. The reaction mixture was filtered through celite bed; filtrate was evaporated under vacuum to dryness. The residue was purified by flash chromatography using methanol and dichloromethane (5 to 15% methanol) as eluent to obtain compound 4b. To a solution of compound 4b (1 equiv.) in ethanol (10 to 100 mL) was added para-toluenesulfonic acid (1 equiv.) and the reaction mixture was stirred for 15 minutes at 140° C. under microwave condition. The reaction mixture was partitioned between saturated sodium bicarbonate and dichloromethane (100 to 500 mL). The organic layer was separated, dried over anhydrous sodium sulfate, concentrated under vacuum and purified by flash chromatography using methanol and dichloromethane (5 to 15% methanol) as eluent.

In a similar fashion 6-fluoro-7-(morpholin-4-yl)-5-(1,3,5-trimethyl-1H-pyrazol-4-yl)-3H-imidazo[4,5-b]pyridin-2-yl] [4-(morpholin-4-yl)piperidin-1-yl]methanone (Compound No. 93) was prepared using [6-fluoro-7-(morpholin-4-yl)-3-(tetrahydro-2H-pyran-2-yl)-5-(1,3,5-trimethyl-1H-pyrazol-4-yl)-3H-imidazo[4,5-b]pyridin-2-yl][4-(morpholin-4-yl) piperidin-1-yl]methanone (95 mg)

$^1$H NMR (400 MHz, DMSO-d6) δ ppm: 13.42 (s, 1H), 4.94-5.05 (m, 1H), 4.43-4.53 (m, 1H), 3.66-3.86 (m, 11H), 3.57 (t, J=4.39 Hz, 4H), 3.17-3.27 (m, 1H), 2.84-2.94 (m, 1H), 2.47 (d, J=4.77 Hz, 5H), 2.19 (d, J=0.75 Hz, 3H), 2.09 (s, 3H), 1.89 (br. s., 2H), 1.30-1.54 (m, 2H). Mass Spectrum (ESI): m/z 527.15 (M+1). [M+H]

Similar compounds listed in Table 2 were prepared following the procedure described in Example 8.

The compound 1 can also be produced by coupling acid compound 5a with an amine compound 1b as shown in Scheme 5.

Scheme 5

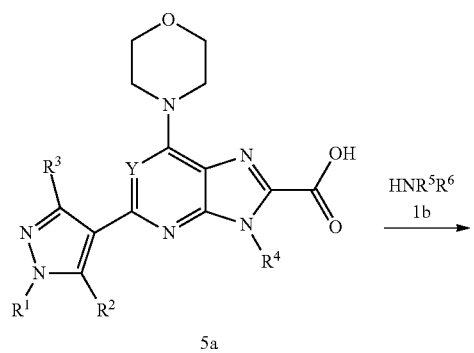

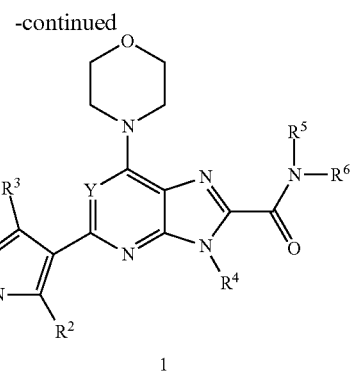

This coupling reaction can be carried out in a solvent such as dimethylformamide, in the presence of a coupling agent such as (benzotriazol-1-yl-oxytripyrrolidinophosphonium hexafluorophosphate) and a base such as N,N-diisopropylethylamine. More specifically, the reaction was carried out as follows:

Example 9

To a solution of compound 5a (1 equiv.; Reference Example 4) in dimethylformamide (10 mL) was added amine compound 1b (1.5 equiv.) and N,N-diisopropylethylamine (1.5 equiv.) and the reaction mixture was stirred for minutes at room temperature. (Benzotriazol-1-yl-oxytripyrrolidinophosphonium hexafluorophosphate) (1.5 equiv.) was added to the reaction mixture, stirred at room temperature for 12 hours. Water was added to it and extracted with dichloromethane. The organic layer was washed with water, dried over sodium sulphate, concentrated under vacuum. The crude mixture was purified by flash chromatography eluting the product with 5-15% methanol in dichloromethane.

In a similar fashion, the following compounds were prepared using appropriate acid compound and amine compound.

{3-[(2R,6S)-2,6-dimethylmorpholin-4-yl]azetidin-1-yl} [5-(1-methyl-1H-pyrazol-4-yl)-7-(morpholin-4-yl)-3H-imidazo[4,5-b]pyridin-2-yl]methanone (Compound No. 119).

$^1$H NMR (400 MHz, DMSO-d$_6$) δ ppm: 13.33 (s, 1H), 8.23 (s, 1H), 7.97 (s, 1H), 6.83 (s, 1H), 4.60-4.70 (m, 1H), 4.36-4.44 (m, 1H), 4.04-4.13 (m, 1H), 3.90-3.99 (m, 5H), 3.88 (s, 3H), 3.80 (d, J=3.79 Hz, 4H), 3.52-3.61 (m, 2H), 3.17-3.24 (m, 1H), 2.68-2.83 (m, 2H), 1.57 (d, J=6.32 Hz, 2H), 1.07 (d, J=6.32 Hz, 6H). Mass Spectrum (ESI): m/z 418.03 [M+H]

N-Methyl-5-(1-methyl-1H-pyrazol-4-yl)-7-(morpholin-4-yl)-N-[1-(tetrahydro-2H-pyran-4-yl)piperidin-4-yl]-3H-imidazo[4,5-b]pyridine-2-carboxamide (Compound No. 121).

$^1$H NMR (400 MHz, DMSO-d$_6$) δ ppm: 13.40-13.58 (m, 1H), 8.24 (s, 1H), 7.93 (s, 1H), 4.84-4.95 (m, 1H), 4.07-4.48 (m, 4H), 3.89 (s, 5H), 3.76 (d, J=4.02 Hz, 4H), 3.30 (m, 4H), 2.92 (s, 5H), 2.00-2.13 (m, 2H), 1.57-1.90 (m, 6H), 1.35-1.52 (m, 2H). Mass Spectrum (ESI): m/z 510.05 [M+H].

4-(1-{[5-(1-Methyl-1H-pyrazol-4-yl)-7-(morpholin-4-yl)-3H-imidazo[4,5-b]pyridin-2-yl]carbonyl}azetidin-3-yl) piperazin-2-one (Compound No. 128).

$^1$H NMR (400 MHz, DMSO-d$_6$) δ ppm: 13.20-13.47 (m, 1H), 8.20-8.25 (m, 1H), 7.95-8.00 (m, 1H), 7.76-7.82 (m, 1H), 6.80-6.87 (m, 1H), 4.64-4.74 (m, 1H), 4.38-4.47 (m, 1H), 4.09-4.17 (m, 1H), 3.92-4.01 (m, 5H), 3.88 (s, 3H), 3.77-3.82 (m, 4H), 3.71-3.76 (m, 1H), 3.17-3.21 (m, 2H), 2.95-2.98 (m, 2H), 2.55-2.60 (m, 2H). Mass Spectrum (ESI): m/z 465.91 [M+H].

1-Methyl-4-(1-{[5-(1-methyl-1H-pyrazol-4-yl)-7-(morpholin-4-yl)-3H-imidazo[4,5-b]pyridin-2-yl]carbonyl}azetidin-3-yl)piperazin-2-one (Compound No. 129).

$^1$H NMR (400 MHz, DMSO-$d_6$) δ ppm: 13.33-13.34 (m, 1H), 8.22 (s, 1H), 7.97 (s, 1H), 6.83 (s, 1H), 4.61-4.75 (m, 1H), 4.38-4.47 (m, 1H), 4.05-4.17 (m, 1H), 3.94 (br. s., 4H), 3.88 (s, 3H), 3.80 (d, J=5.02 Hz, 4H), 3.15-3.18 (m, 1H), 3.03 (d, J=4.27 Hz, 2H), 2.83 (s, 3H), 2.63-2.70 (m, 2H). Mass Spectrum (ESI): m/z 479.98 [M+H].

1-Methyl-4-(1-{[2-(1-methyl-1H-pyrazol-4-yl)-6-(morpholin-4-yl)-9H-purin-8-yl]carbonyl}azetidin-3-yl)piperazin-2-one (Compound No. 130).

$^1$H NMR (400 MHz, DMSO-$d_6$) δ ppm: 13.58-13.67 (m, 1H), 8.24 (s, 1H), 7.92 (s, 1H), 4.63-4.73 (m, 1H), 4.38-4.47 (m, 1H), 4.16-4.38 (m, 2H), 4.08-4.16 (m, 1H), 3.93-4.00 (m, 1H), 3.88 (s, 3H), 3.76 (br. s., 4H), 3.25-3.30 (m, 2H), 3.03 (s, 2H), 2.83 (s, 3H), 2.61-2.71 (m, 2H). Mass Spectrum (ESI): m/z 480.98 [M+H].

N-Methyl-5-(1-methyl-1H-pyrazol-4-yl)-7-(morpholin-4-yl)-N-[1-(oxetan-3-yl)piperidin-4-yl]-3H-imidazo[4,5-b]pyridine-2-carboxamide (Compound No. 131).

$^1$H NMR (400 MHz, DMSO-$d_6$) δ ppm: 13.13-13.31 (m, 1H), 8.23 (s, 1H), 7.98 (s, 1H), 6.84 (s, 1H), 4.92-5.14 (m, 1H), 4.49-4.60 (m, 2H), 4.35-4.46 (m, 2H), 3.91 (br. s., 4H), 3.88 (s, 3H), 3.79 (d, J=5.02 Hz, 4H), 2.94 (s, 2H), 2.77-2.83 (m, 2H), 1.67-1.91 (m, 6H). Mass Spectrum (ESI): m/z 480.97 [M+H].

Alternatively, the coupling agent such as 1-ethyl-3-(3-dimethylaminopropyl)carbodiimide and hydroxybenzotriazole can be used. For example, [2-(1-methyl-1H-pyrazol-4-yl)-6-(morpholin-4-yl)-9H-purin-8-yl][4-(morpholin-4-yl)piperidin-1-yl]methanone (Compound No. 58) was prepared as follows.

Example 10

To a solution of compound 5a (150 mg, 455.4 mmol; Reference Example 4) in dimethylformamide (3 mL), triethylamine (0.13 mL, 910.8 mmol), 1-ethyl-3-(3-dimethylaminopropyl)carbodiimide (173 mg, 910.8 mmol), hydroxybenzotriazole (123 mg, 910.8 mmol) and morpholine piperidine (116 mg, 683.2 mmol; AK Scientific)) was added and reaction mixture was stirred at room temperature for overnight. Water was added to the reaction mixture and extracted with dichloromethane (150 mL×2). The combined organic extracts were washed with brine (10 mL), dried and concentrated under reduced pressure. The crude product was purified by flash chromatography eluting the product with 5-10% methanol in dichloromethane to obtain [2-(1-methyl-1H-pyrazol-4-yl)-6-(morpholin-4-yl)-9H-purin-8-yl][4-(morpholin-4-yl)piperidin-1-yl]methanone (152 mg).

The compound 1 (wherein R$^1$ is methyl, R$^2$, R$^3$ and R$^4$ are hydrogen) can also be produced following the reaction Scheme 6 as shown below.

Scheme 6

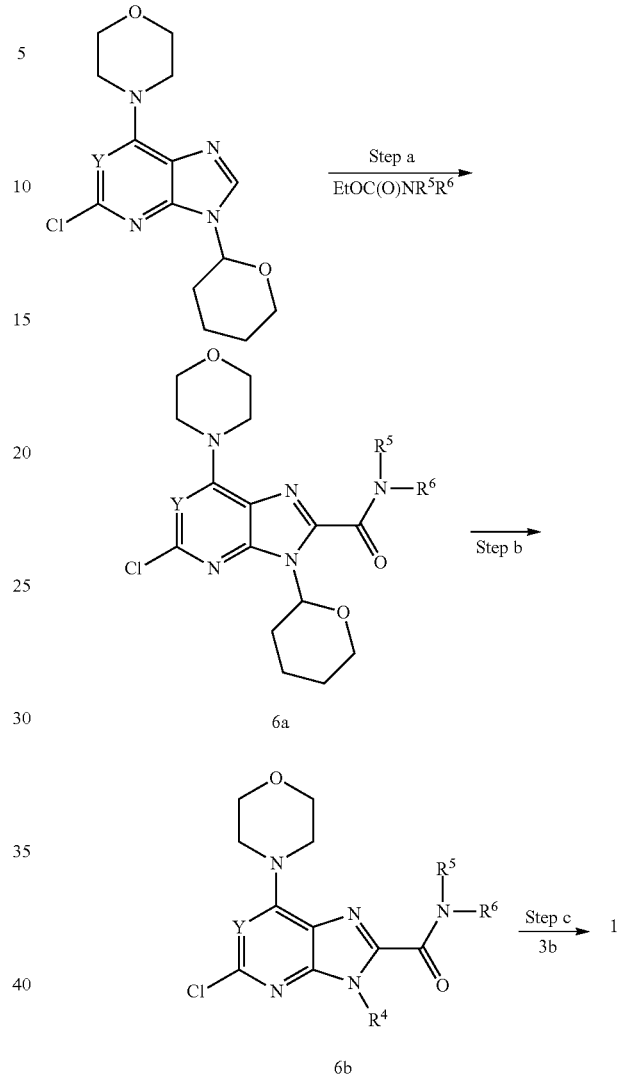

Following Scheme 6, compounds of the present invention, particularly when Y represents N, can be prepared. For example, [2-(1-methyl-1H-pyrazol-4-yl)-6-(morpholin-4-yl)-9H-purin-8-yl][4-(morpholin-4-yl)piperidin-1-yl]methanone (Compound No. 58) was prepared as follows:

Step a: Synthesis of 6a (Wherein, —NR$^5$R$^6$ is Morpholine Piperidinyl)

To a solution of 2-chloro-6-(morpholin-4-yl)-9-(tetrahydro-2H-pyran-2-yl)-9H-purine (1 g, 3.09 mmol) and carbamate (2.2 g, 9.28 mmol; Reference Example 23) in tetrahydrofuran (70 mL) was added lithium diisopropylamide (2 M) in tetrahydrofuran (4.6 mL, 9.28 mmol) drop wise at −78° C. and then stirred at same temperature for 30 minutes and allowed the reaction mixture to come at room temperature over a period of 90 minutes. The reaction mixture was poured into saturated ammonium chloride solution (100 mL), and extracted using ethyl acetate (150 mL×2). The combined organic extracts were dried over anhydrous sodium sulphate and concentrated under vacuum to dryness. The crude product was purified by flash chromatography using 2-5% methanol in dichloromethane as gradient system to obtain compound 6a (1.07 g) as off white solid.

$^1$H NMR (400 MHz, CHCl$_3$-d) δ ppm: 5.67-5.84 (m, 1H), 4.57-4.85 (m, 1H), 3.95-4.55 (m, 5H), 3.80 (t, J=3.76 Hz, 4H), 3.52-3.77 (m, 7H), 2.80-3.18 (m, 2H), 2.48-2.64 (m, 5H), 2.45 (td, J=3.45, 7.15 Hz, 1H), 1.98 (br. s., 4H), 1.96 (m, 4H).

Step b: Synthesis of 6b

To a solution of compound 6a (400 mg, 0.7692 mmol) in ethanol (15 mL) was added p-toluenesulfonic acid monohydrate (146 mg, 0.7692 mmol) and refluxed for 2 hours at 100° C. The thin layer chromatography was checked and it showed starting material still unreacted hence again p-toluenesulfonic acid monohydrate (43 mg, 0.230 mmol) was added and reflux for 1 hour. The reaction mixture was cooled to room temperature, poured over saturated sodium bicarbonate solution (100 mL) and extracted with dichloromethane (150 mL×2). The combined organic extract was dried over anhydrous sodium sulphate and concentrated under vacuum. The residue was triturated in hexane and filtered over Buchner funnel, dried under vacuum to obtain compound 6b (290 mg).

$^1$H NMR (400 MHz, DMSO-d$_6$) δ ppm: 13.57-14.14 (m, 1H), 4.88 (d, J=14.15 Hz, 1H), 4.46 (d, J=13.39 Hz, 1H), 4.01 (br s, 5H), 3.73 (t, J=4.55 Hz, 4H), 3.49-3.63 (m, 4H), 3.23 (t, J=11.62 Hz, 1H), 2.84-2.95 (m, 1H), 2.41-2.49 (m, 4H), 1.75-1.96 (m, 2H), 1.24-1.51 (m, 2H).

Step c: Synthesis of [2-(1-methyl-1H-pyrazol-4-yl)-6-(morpholin-4-yl)-9H-purin-8-yl][4-(morpholin-4-yl)piperidin-1-yl]methanone To a solution of compound 6b (200 mg, 0.4587 mmol) in acetonitrile (4 mL) was added compound 3b (1-methyl 4-pyrazole boronic acid pinacol ester; 143.11 g, 0.688 mmol), aqueous solution of sodium carbonate (121.55 mg, 1.146 mmol) in water and (2 mL), [1,1'-bis(diphenylphosphino)ferrocene]palladium(II) dichloride (18.714 mg, 0.022 mmol) and purged the reaction mixture using argon for 15 minutes. After 15 minutes argon was removed and reaction was allowed to reflux at 140° C. for 8-10 hours. The reaction mixture was cooled to room temperature, water was added (80 mL) and extracted using 10% methanol-dichloromethane (100 mL×2). The combined organic extract was dried over anhydrous sodium sulphate and concentrated under vacuum. The residue was purified using flash chromatography and eluting the product in 8-20% methanol in dichloromethane to obtain [2-(1-methyl-1H-pyrazol-4-yl)-6-(morpholin-4-yl)-9H-purin-8-yl][4-(morpholin-4-yl)piperidin-1-yl]methanone (183 mg).

Synthesis of Ester Compound 1a and 5a

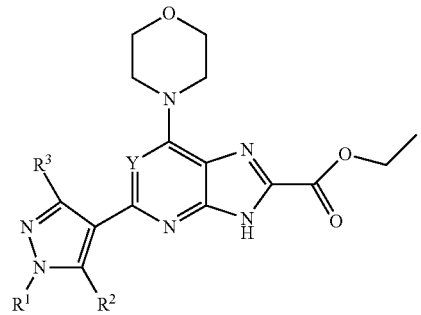

1a

[Reference Example 1] Synthesis of ethyl 2-(1-methyl-1H-pyrazol-4-yl)-6-(morpholin-4-yl)-9H-purine-8-carboxylate

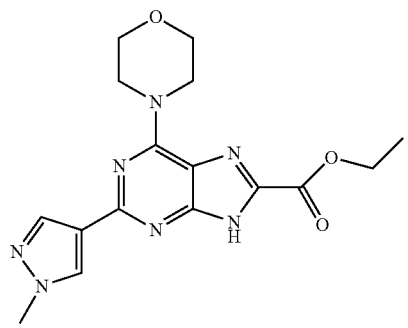 [SMILES: CCOC(=O)c1nc2c(N3CCOCC3)nc(-c3cnn(C)c3)nc2[nH]1]

Step a: Synthesis of 2,6-dichloro-9-(tetrahydro-2H-pyran-2-yl)-9H-purine

To a solution of 2,6-dichloro-9H-purine (50 g, 264.55 mmol) in ethyl acetate (500 mL), were added p-toluenesulfonic acid monohydrate (1.36 g, 7.92 mmol) followed by 3,4 dihydro-2H-pyran (55.36 g, 661.37 mmol) via dropping funnel and heated at 70 to 80° C. for 4 hours. The reaction mixture was cooled to room temperature and ammonia (15 mL) was added, stirred for 15 minutes. Water (400 mL) was added and extracted with ethyl acetate (300 mL thrice). The combined organic extracts were dried over anhydrous sodium sulfate and concentrated under vacuum to dryness. The residue was triturated in hexane (500 mL), filtered and dried under vacuum to obtain 70 g of 2,6-dichloro-9-(tetrahydro-2H-pyran-2-yl)-9H-purine.

$^1$H NMR (400 MHz, DMSO-d$_6$) δ ppm: 8.96 (s, 1H), 5.75 (dd, J=2.01, 10.79 Hz, 1H), 3.99-4.12 (m, 1H), 3.69-3.83 (m, 1H), 2.20-2.34 (m, 1H), 1.93-2.07 (m, 2H), 1.69-1.84 (m, 1H), 1.39-1.67 (m, 2H).

Step b: Synthesis of 2-chloro-6-(morpholin-4-yl)-9-(tetrahydro-2H-pyran-2-yl)-9H-purine

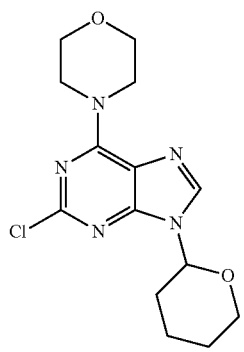 [SMILES: Clc1nc(N2CCOCC2)c2ncn(C3CCCCO3)c2n1]

To a solution of 2,6-dichloro-9-(tetrahydro-2H-pyran-2-yl)-9H-purine (17 g, 62.24 mmol) in methanol (300 mL), was added morpholine (11.92 g, 136.92 mmol) at 0° C. The reaction mixture was stirred at room temperature for 3 hours. The solvent was removed under vacuum; water (300 mL) was added and extracted with dichloromethane (500 mL thrice). The combined organic extracts were dried over anhydrous sodium sulfate and concentrated under vacuum to dryness to obtain 20 g of 2-chloro-6-(morpholin-4-yl)-9-(tetrahydro-2H-pyran-2-yl)-9H-purine.

$^1$H NMR (400 MHz, DMSO-d$_6$) δ ppm: 8.42 (s, 1H), 5.60 (dd, J=2.13, 10.92 Hz, 1H), 4.01 (dd, J=1.76, 10.79 Hz, 2H), 3.64-3.77 (m, 7H), 2.51 (td, J=1.76, 3.51 Hz, 1H), 2.11-2.25 (m, 1H), 1.90-2.01 (m, 2H), 1.69-1.81 (m, 1H), 1.53-1.62 (m, 2H).

Step c: Synthesis of ethyl 2-chloro-6-(morpholin-4-yl)-9-(tetrahydro-2H-pyran-2-yl)-9H-purine-8-carboxylate

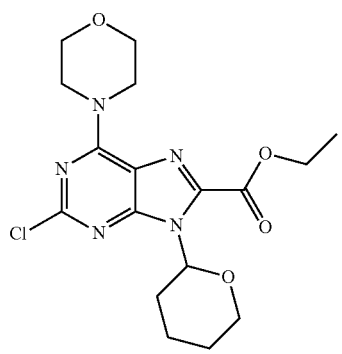 [SMILES: CCOC(=O)c1nc2c(N3CCOCC3)nc(Cl)nc2n1C1CCCCO1]

To a solution of 2-chloro-6-(morpholin-4-yl)-9-(tetrahydro-2H-pyran-2-yl)-9H-purine (10 g, 30.88 mmol) in dry tetrahydrofuran (200 mL) was added N,N,N,N tetra methylethylenediamine (5.383 g, 46.32 mmol) at room temperature and cooled to −78° C. To the reaction mixture, n-butyl lithium (1.6M, 29 mL, 46.32 mmol) was added drop wise and allowed to warm at −50° C. for 1 hour. The reaction mixture was again cooled to −78° C. and stirred for 5 minutes. In a round bottom flask, ethyl chloroformate (14.7 mL, 154.43 mmol) was taken in dry tetrahydrofuran (100 mL) and cooled to −78° C. The reaction mixture was directly poured in to the solution of ethyl chloroformate via liquid funnel and stirred for 2 minutes. The reaction mixture was poured into saturated ammonium chloride solution (400 mL), and extracted with ethyl acetate (500 mL thrice). The combined organic extracts were dried over anhydrous sodium sulfate and concentrated under vacuum to dryness, which was purified by column chromatography on silica gel (100-200 mesh) using ethyl acetate and hexane (15-30%) as gradient system. The purest fractions were collected and concentrated under vacuum to obtain 7.5 g of ethyl 2-chloro-6-(morpholin-4-yl)-9-(tetrahydro-2H-pyran-2-yl)-9H-purine-8-carboxylate.

$^1$H NMR (400 MHz, DMSO-d$_6$) δ ppm: 6.02-6.14 (m, 1H), 4.36-4.45 (m, 2H), 3.99-4.07 (m, 2H), 3.69-3.78 (m, 4H), 3.58-3.67 (m, 1H), 2.69-2.78 (m, 1H), 1.81-2.02 (m, 2H), 1.42-1.70 (m, 4H), 1.35 (t, 3H), 1.21-1.30 (m, 2H).

Step d: Synthesis of ethyl 2-(1-methyl-1H-pyrazol-4-yl)-6-(morpholin-4-yl)-9-(tetrahydro-2H-pyran-2-yl)-9H-purine-8-carboxylate

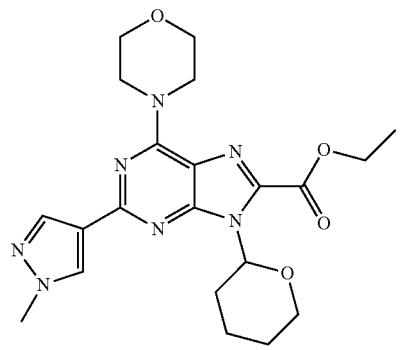 [SMILES: CCOC(=O)c1nc2c(N3CCOCC3)nc(-c3cnn(C)c3)nc2n1C1CCCCO1]

To a solution of ethyl 2-chloro-6-(morpholin-4-yl)-9-(tetrahydro-2H-pyran-2-yl)-9H-purine-8-carboxylate (14 g, 35.36 mmol) in 1,2-dichloroethane (210 mL) were added 1-methyl 4-pyrazole boronic acid pinacol ester (9.595 g, 45.97 mmol), cesium carbonate (28.751 g, 88.41 mmol), tetrakis(triphenylphosphine)palladium(0) (4.086 g, 3.53 mmol) and purged the reaction mixture using argon for 15 minutes. After 15 minutes argon was removed and reaction was allowed to reflux at 110° C. for 4 hours. The reaction mixture was cooled to room temperature; water (400 mL) was added and extracted with dichloromethane (500 mL twice). The combined organic extracts were dried over anhydrous sodium sulfate and concentrated under vacuum to obtain the crude product, which was purified by column chromatography using ethyl acetate and hexane (50% ethyl acetate-hexane to pure ethyl acetate system) as gradient system. The purest fractions were collected and concentrated under vacuum to obtain 13.5 g of ethyl 2-(1-methyl-1H-pyrazol-4-yl)-6-(morpholin-4-yl)-9-(tetrahydro-2H-pyran-2-yl)-9H-purine-8-carboxylate.

$^1$H NMR (400 MHz, DMSO-d$_6$) δ ppm: 8.30 (s, 1H), 7.99 (s, 1H), 6.11-6.23 (m, 1H), 4.40 (dd, J=1.25, 7.03 Hz, 3H), 4.16-4.35 (m, 3H), 4.00-4.10 (m, 1H), 3.90 (s, 3H), 3.72-3.81 (m, 4H), 3.58-3.69 (m, 1H), 3.02-3.15 (m, 1H), 1.94-2.06 (m, 1H), 1.82-1.92 (m, 1H), 1.52-1.71 (m, 3H), 1.35 (t, J=7.03 Hz, 3H).

Step e: Synthesis of ethyl 2-(1-methyl-1H-pyrazol-4-yl)-6-(morpholin-4-yl)-9H-purine-8-carboxylate To a solution of ethyl 2-(1-methyl-1H-pyrazol-4-yl)-6-(morpholin-4-yl)-9-(tetrahydro-2H-pyran-2-yl)-9H-purine-8-carboxylate (10 g, 22.67 mmole) in ethanol (200 mL) was added p-toluene sulfonic acid monohydrate (4.31 g, 22.67 mmole) and refluxed for 14 hours. The reaction mixture was cooled to room temperature, poured over saturated sodium bicarbonate solution and extracted with dichloromethane (500 mL thrice). The combined organic extracts were dried over anhydrous sodium sulfate and concentrated under vacuum to obtain the crude product, which was then purified by triturated with hexane (200 mL) to obtain 5.1 g of pure ethyl 2-(1-methyl-1H-pyrazol-4-yl)-6-(morpholin-4-yl)-9H-purine-8-carboxylate.

$^1$H NMR (400 MHz, DMSO-$d_6$) δ ppm: 13.67-14.03 (m, 1H), 8.26 (s, 1H), 7.95 (s, 1H), 4.38 (d, J=7.07 Hz, 3H), 4.18-4.34 (m, 2H), 3.89 (s, 3H), 3.77 (t, J=4.67 Hz, 4H), 1.34 (t, J=7.07 Hz, 3H).

Ethyl 2-(1-methyl-1H-pyrazol-4-yl)-6-(morpholin-4-yl)-9H-purine-8-carboxylate was also prepared as follows.

Step a: Synthesis of 2-chloro-6-(morpholin-4-yl)-9-(tetrahydro-2H-pyran-2-yl)-9H-purine-8-carbaldehyde

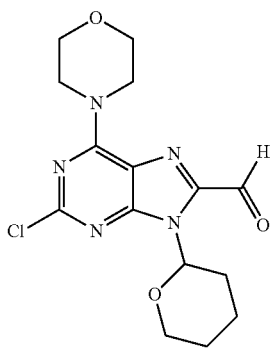 [SMILES: O=Cc1nc2c(N3CCOCC3)nc(Cl)nc2n1C1CCCCO1]

To a mixture of diisopropylamine (18.76 g, 185 mmole) in tetrahydrofuran (100 ml) was added n-butyl lithium (1.6M in hexane, 110 mL, 185 mmole) at −78° C. and stirred for 30 minutes at 0° C. To this freshly prepared lithium diisopropylamide was added a solution of 2-chloro-6-(morpholin-4-yl)-9-(tetrahydro-2H-pyran-2-yl)-9H-purine (20 g, 61.9 mmole) in tetrahydrofuran (100 mL) drop wise at −78° C., and stirred for 30 minutes. Dimethylformamide (13.5 g, 185 mmole) was added at −78° C., stirred at same temperature for 2 hours. Saturated solution of ammonium chloride (250 mL) was added to the reaction mixture, extracted with ethyl acetate (500 mL thrice). The combined organic layer was dried over anhydrous sodium sulfate and concentrated under vacuum to obtain 19 g of the title compound.

$^1$H NMR (400 MHz, DMSO-$d_6$) δ ppm: 9.93 (s, 1H), 5.57-5.63 (m, 1H), 4.03 (d, J=7.03 Hz, 2H), 3.67-3.75 (m, 8H), 1.57 (d, J=5.02 Hz, 4H), 0.81-0.96 (m, 2H).

Step b: Synthesis of 2-chloro-6-(morpholin-4-yl)-9H-purine-8-carboxylic acid

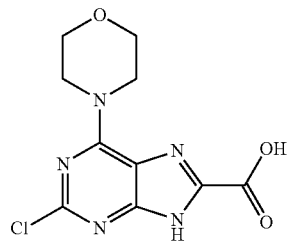 [SMILES: O=C(O)c1nc2c(N3CCOCC3)nc(Cl)nc2[nH]1]

To a solution of 2-chloro-6-(morpholin-4-yl)-9-(tetrahydro-2H-pyran-2-yl)-9H-purine-8-carbaldehyde (8 g, 22.7 mmole) in ethanol (30 mL) was added silver nitrate (4.86 g, 28.65 mmole) and sodium hydroxide solution (1.5N, 70 mL), followed by stirring at room temperature for 12 hours. The reaction mixture was filtered over celite pad, the filtrate was concentrated and the residue was taken in water and basified by adding sodium hydroxide (1N), then extracted with dichloromethane (200 mL twice), the aqueous layer was acidified with concentrated hydrochloric acid, the volume was reduced to half by evaporation under vacuum to form the precipitate which was filtered and dried to obtain 7 g of 2-chloro-6-(morpholin-4-yl)-9H-purine-8-carboxylic acid.

$^1$H NMR (400 MHz, DMSO-$d_6$) δ ppm: 13.71-14.31 (m, 1H), 4.40-4.74 (m, 1H), 3.67-4.00 (m, 4H), 3.34 (br. s., 4H).

Step c: Synthesis of ethyl 2-chloro-6-(morpholin-4-yl)-9H-purine-8-carboxylate

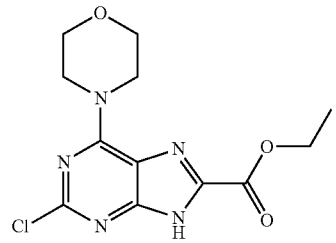 [SMILES: CCOC(=O)c1nc2c(N3CCOCC3)nc(Cl)nc2[nH]1]

To a solution of 2-chloro-6-(morpholin-4-yl)-9H-purine-8-carboxylic acid (4 g, 14.1 mmole) in ethanol (200 mL) was added thionyl chloride (20 mL) at 0° C. and the reaction mixture was refluxed for 12 hours. The reaction mixture was concentrated under vacuum, and the residue was taken in water, extracted with dichloromethane (300 mL twice). The combined organic layer was washed with brine, dried over anhydrous sodium sulfate and concentrated under vacuum. The residue was purified by column chromatography using methanol and dichloromethane (5% methanol) as eluent to obtain 3 g of ethyl 2-chloro-6-(morpholin-4-yl)-9H-purine-8-carboxylate.

Ethyl 2-chloro-6-(morpholin-4-yl)-9H-purine-8-carboxylate was also prepared as follows. To a solution of ethyl 2-chloro-6-(morpholin-4-yl)-9-(tetrahydro-2H-pyran-2-yl)-9H-purine-8-carboxylate (10 g, 25.44 mmole) in ethanol (200 mL), was added para-toluene sulfonic acid monohydrate (4.84 g, 25.44 mmole) and refluxed for 14 hours. The reaction mixture was cooled to room temperature, poured over saturated sodium bicarbonate solution and extracted with dichloromethane (500 mL thrice). The combined organic extracts were dried over anhydrous sodium sulfate and concentrated under vacuum to obtain crude product, triturated with hexane to obtain 7.4 g of the title compound as light yellow solid.

$^1$H NMR (400 MHz, DMSO-d$_6$) δ ppm: 13.37-15.08 (m, 1H), 4.32-4.43 (q, J=7.07 Hz, 2H), 3.99-4.31 (m, 4H), 3.69-3.81 (m, 4H), 1.34 (t, J=7.07 Hz, 3H).

Step d: Synthesis of ethyl 2-(1-methyl-1H-pyrazol-4-yl)-6-(morpholin-4-yl)-9H-purine-8-carboxylate To a solution of ethyl 2-chloro-6-(morpholin-4-yl)-9H-purine-8-carboxylate (3 g, 9.6 mmol) in dimethylformamide (30 mL) were added 1-methyl 4-pyrazole boronic acid pinacol ester (2.82 g, 13.5 mmol), cesium carbonate (7.8 g, 24 mmol) and tetrakis(triphenylphosphine)palladium(0) (1.1 g, 0.96 mmol), purged the reaction mixture using argon for 15 minutes. Argon was removed and reaction was allowed to reflux at 110° C. for 4 hours. The reaction mixture was cooled to room temperature; water (100 mL) was added and then extracted with dichloromethane (300 mL twice). The combined organic extracts were dried over anhydrous sodium sulfate and concentrated under vacuum to obtain the crude material, which was purified by column chromatography using methanol and dichloromethane (5% methanol) as gradient system to obtain 1.8 g of the title compound.

$^1$H NMR (400 MHz, DMSO-d$_6$) δ ppm: 13.67-14.03 (m, 1H), 8.26 (s, 1H), 7.95 (s, 1H), 4.38 (d, J=7.07 Hz, 3H), 4.18-4.34 (m, 2H), 3.89 (s, 3H), 3.77 (t, J=4.67 Hz, 4H), 1.34 (t, J=7.07 Hz, 3H).

[Reference Example 2] Synthesis of ethyl 6-fluoro-5-(1-methyl-1H-pyrazol-4-yl)-7-(morpholin-4-yl)-3H-imidazo[4,5-b]pyridine-2-carboxylate

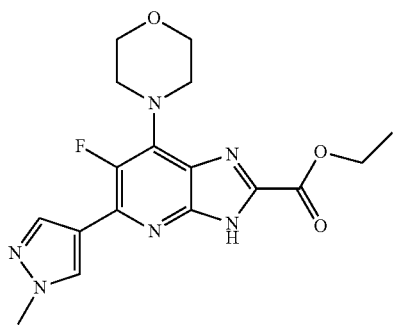 [SMILES: CCOC(=O)c1nc2c(N3CCOCC3)c(F)c(-c3cnn(C)c3)nc2[nH]1]

To a solution of ethyl 6-fluoro-5-(1-methyl-1H-pyrazol-4-yl)-7-(morpholin-4-yl)-3-(tetrahydro-2H-pyran-2-yl)-3H-imidazo[4,5-b]pyridine-2-carboxylate (700 mg, 1.52 mmol) in ethanol (10 mL) was added p-toluene sulfonic acid (290 mg, 1.52 mmol) and the reaction mixture was refluxed for 2 hours at 100° C. The reaction was cooled to room temperature; saturated sodium bicarbonate (50 mL) was added and extracted with dichloromethane (250 mL twice). The combined organic extracts were dried over anhydrous sodium sulfate, concentrated under vacuum, hexanes (50 mL) added and stirred for 5 minutes, filtered, dried under vacuum to obtain 500 mg of the title compound.

[Reference Example 3] Synthesis of ethyl 5-(1-methyl-1H-pyrazol-4-yl)-7-(morpholin-4-yl)-3H-imidazo[4,5-b]pyridine-2-carboxylate

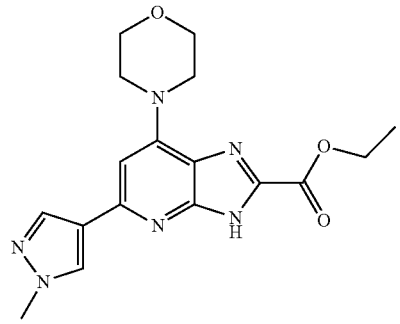 [SMILES: CCOC(=O)c1nc2c(N3CCOCC3)cc(-c3cnn(C)c3)nc2[nH]1]

To a solution of ethyl 5-(1-methyl-1H-pyrazol-4-yl)-7-(morpholin-4-yl)-3-(tetrahydro-2H-pyran-2-yl)-3H-imidazo[4,5-b]pyridine-2-carboxylate (450 mg, 1.025 mmole) in ethanol (5 mL) was added p-toluene sulfonic acid (194 mg, 1.025 mmole) and the reaction mixture was refluxed for 14 hours. The reaction mixture was cooled to room temperature and saturated sodium bicarbonate (50 mL) was added, extracted with dichloromethane (250 mL thrice). The combined organic extracts were dried over anhydrous sodium sulfate, concentrated under vacuum to afford crude which was triturated using hexanes (50 mL) and filtered, dried under vacuum to obtain 210 mg of the title compound as yellow solid.

$^1$H NMR (400 MHz, DMSO-d$_6$) δ ppm: 13.68 (br. s., 1H), 8.27 (s, 1H), 8.01 (s, 1H), 6.85 (s, 1H), 4.37 (q, J=7.03 Hz, 2H), 3.96 (br. s., 4H), 3.76-3.92 (m, 8H), 1.34 (t, J=7.03 Hz, 3H).

[Reference Example 4] Synthesis of 2-(1-methyl-1H-pyrazol-4-yl)-6-(morpholin-4-yl)-9H-purine-8-carboxylic acid

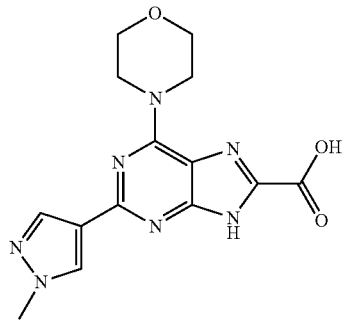 [SMILES: Cn1cc(-c2nc(N3CCOCC3)c3nc(C(=O)O)[nH]c3n2)cn1]

To a solution of ethyl 2-(1-methyl-1H-pyrazol-4-yl)-6-(morpholin-4-yl)-9-(tetrahydro-2H-pyran-2-yl)-9H-purine-8-carboxylate. (5 g, 11.32 mmole; Reference Example 1) in tetrahydrofuran and water (8:2, 60 mL) was added lithium hydroxide (1.42 g, 33.97 mmole) and the reaction mixture was stirred at room temperature for 12 hours. The reaction mixture was evaporated to dryness, water (15 mL) was added, washed with ethyl acetate (100 mL twice). The aqueous layer was acidified using concentrated hydrochloric acid (pH2). The precipitate formed was filtered and the residue was washed with hexane and dried to get title compound (2.5 g).

$^1$H NMR (400 MHz, DMSO-d6) δ ppm: 12.42-13.44 (m, 1H), 8.16-8.23 (m, 1H), 7.86-7.94 (m, 1H), 4.17-4.40 (m, 4H), 3.88 (s, 3H), 3.75 (br. s., 4H). Mass Spectrum (ESI): m/z 330.7.

Synthesis of Ester Compound 2a

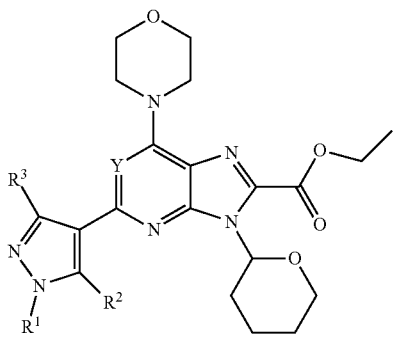

General Method of Synthesis of Ester Compound 2a

To a solution of ethyl 5-chloro-6-fluoro-7-(morpholin-4-yl)-3-(tetrahydro-2H-pyran-2-yl)-3H-imidazo[4,5-b]pyridine-2-carboxylate (1 equiv.) in 1,2-dichloroethane (10 mL), was added boronate ester 3b (1.25 equiv.) and cesium carbonate (2.5 equiv.) and the reaction mixture was purged with Argon for 10 minutes, tetrakis(triphenylphosphine)palladium(0) (0.075 equiv.) was added and the mixture was heated for 1 hour under microwave condition at 140° C. The reaction mixture was filtered through celite bed; filtrate was evaporated under vacuum to dryness. The residue was purified by flash chromatography using methanol and dichloromethane (5 to 15% methanol) as eluting system to obtain ester compound 2a.

[Reference Example 5] Synthesis of ethyl 5-(1-methyl-1H-pyrazol-4-yl)-7-(morpholin-4-yl)-3-(tetrahydro-2H-pyran-2-yl)-3H-imidazo[4,5-b]pyridine-2-carboxylate

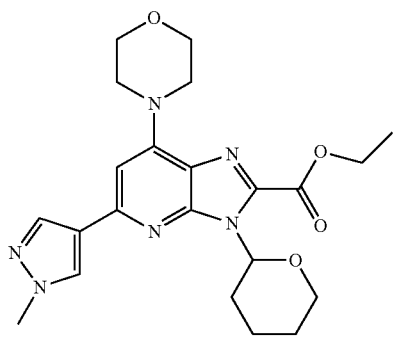 [SMILES: CCOC(=O)c1nc2c(N3CCOCC3)cc(-c3cnn(C)c3)nc2n1C1CCCCO1]

To a solution of ethyl 5-chloro-7-(morpholin-4-yl)-3-(tetrahydro-2H-pyran-2-yl)-3H-imidazo[4,5-b]pyridine-2-carboxylate (1 g, 2.53 mmole) in 1,2-dichloroethane (10 mL) was added boronate ester (791 mg, 3.8 mmole, combiblocks) and potassium phosphate (1.34 g, 6.34 mmole, acros) and the reaction mixture was purged with Argon for 30 minutes, tetrakis(triphenylphosphine)palladium(0) (293 mg, 0.25 mmole) was added and the mixture was stirred for 1 hour under microwave condition at 140° C. The reaction mixture was filtered through celite pad, evaporated under vacuum to dryness. The residue was dissolved in dichloromethane (300 mL) and washed with water (100 mL), brine (100 mL) and dried over anhydrous sodium sulfate, concentrated under vacuum and purified by column chromatography using methanol and dichloromethane (5% methanol) as eluent to obtain 1.2 g of the title compound as white solid.

$^1$H NMR (400 MHz, DMSO-d$_6$) δ ppm: 8.30 (s, 1H), 8.05 (s, 1H), 6.91 (s, 1H), 6.17-6.22 (m, 1H), 4.40 (dd, J=2.53, 7.07 Hz, 2H), 4.00-4.07 (m, 1H), 3.88-3.95 (m, 7H), 3.77-3.84 (m, 4H), 3.59-3.68 (m, 1H), 3.08-3.15 (m, 1H), 1.98-2.05 (m, 1H), 1.82-1.90 (m, 1H), 1.62-1.71 (m, 2H), 1.53-1.60 (m, 1H), 1.36 (t, J=7.07 Hz, 3H).

[Reference Example 6] Synthesis of ethyl 5-(1,3-dimethyl-1H-pyrazol-4-yl)-7-(morpholin-4-yl)-3-(tetrahydro-2H-pyran-2-yl)-3H-imidazo[4,5-b]pyridine-2-carboxylate

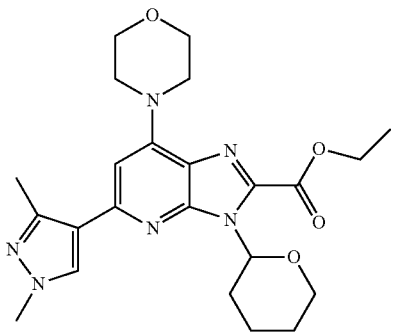 [SMILES: CCOC(=O)c1nc2c(N3CCOCC3)cc(-c3cn(C)nc3C)nc2n1C1CCCCO1]

To a solution of ethyl 5-chloro-7-(morpholin-4-yl)-3-(tetrahydro-2H-pyran-2-yl)-3H-imidazo[4,5-b]pyridine-2-carboxylate (1 g, 2.53 mmol) in 1,2-dichloroethane (15 mL) were added 1,3-dimethyl 4-pyrazole boronic acid pinacol ester (729 mg, 3.28 mmol), cesium carbonate (2.053 g, 6.31 mmol), tetrakis(triphenylphosphine)palladium(0) (292 mg, 0.25 mmol) and purged the reaction mixture using argon for 15 minutes. After 15 minutes argon was removed and reaction was allowed to reflux at 110° C. for 4 hours. The reaction mixture cooled to room temperature, water (400 mL) was added and extracted with dichloromethane (500 mL twice). The combined organic extracts were dried over anhydrous sodium sulfate and concentrated under vacuum to obtain crude product, which on purification by column chromatography using 50% ethyl acetate-hexane to pure ethyl acetate system gave 1.4 g of the title compound.

Synthesis of Amide Compound 3a

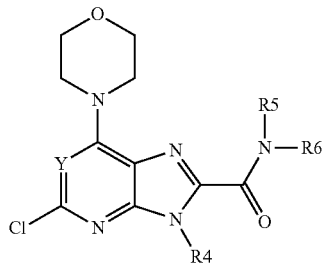

General Method of Synthesis of Amide Compound 3a

Step a: Synthesis of Amide Compound of Formula

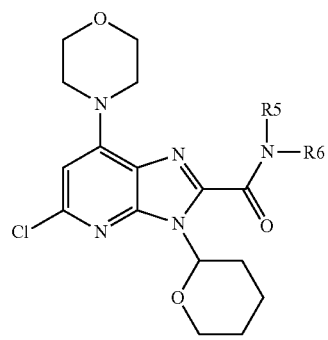

To a solution of ethyl 5-chloro-7-(morpholin-4-yl)-3-(tetrahydro-2H-pyran-2-yl)-3H-imidazo[4,5-b]pyridine-2-carboxylate (1 equiv.) and amine compound 1b (3 equiv.) in tetrahydrofuran (20 mL) was added trimethyl aluminium (4 equiv.) at room temperature and the reaction mixture was refluxed for 20 hours. The reaction mixture was cooled to room temperature and saturated solution of ammonium chloride (50 to 200 mL) was added, partitioned with dichloromethane (300 to 800 mL). The organic layer was separated, dried over anhydrous sodium sulfate, concentrated under vacuum and purified by flash chromatography using methanol and dichloromethane (5 to 10% methanol) as eluent to obtain the desired compounds.

Step b: Synthesis of Amide Compound of Formula

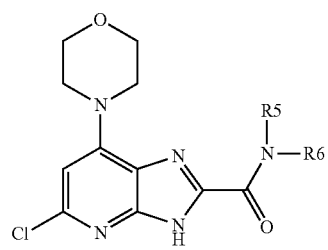

To a solution of compound (1 equiv., Step a) in ethanol (10 mL) was added p-toluene sulfonic acid (1 equiv.) and the reaction mixture was refluxed for 18 hours. The reaction was cooled to room temperature and partitioned between saturated sodium bicarbonate (50 to 200 mL) and dichloromethane (300 to 800 mL). The organic layer was separated, dried over anhydrous sodium sulfate, concentrated under vacuum and purified by flash chromatography using methanol and dichloromethane (5 to 15% methanol) as eluent to obtain the desired compounds.

Step c: Synthesis of Amide Compound of Formula

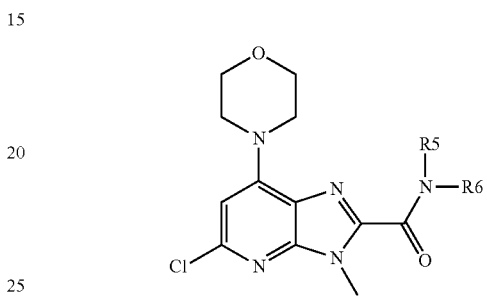

To a solution of amide compound (1 equiv., Step b) in dimethylformamide (12 mL) was added potassium carbonate (2.5 equiv.) followed by methyl iodide (1.5 equiv.) at 0° C. and allowed to warm at room temperature for 2 hours. Water (20 to 100 mL) was added and extracted with ethyl acetate (100 to 400 mL thrice). The combined organic extracts were dried over anhydrous sodium sulfate, concentrated under vacuum and purified by flash chromatography using methanol and dichloromethane (5 to 15% methanol) as eluent to obtain the desired compound.

Step d: Synthesis of Amide Compound of Formula

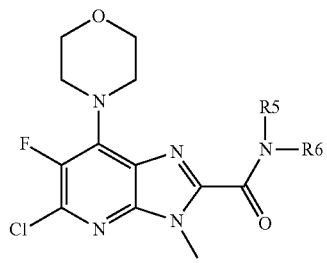

To a solution of compound (1 equiv., Step c) in acetonitrile (110 mL) was added accuflor (2.3 equiv.) at 0° C. and allowed to warm at room temperature for 2.5 hours. Saturated ammonium chloride (50 to 200 mL) was added and extracted with dichloromethane (200 to 500 mL thrice). The combined organic extracts were dried over anhydrous sodium sulfate, concentrated under vacuum and purified by flash chromatography using methanol and dichloromethane (5 to 15% methanol) as eluent to obtain the desired compound.

The compound 3a can also be prepared by coupling 2-chloro-6-(morpholin-4-yl)-9H-purine-8-carbonyl chloride (intermediate not isolated) with an amine compound 1b as shown below:

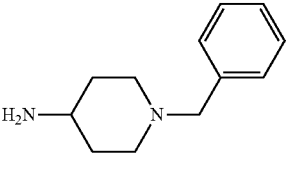

| Compound 1b (mg) (Source) |
|---|
| HN(CH₃)₂ (190) (Aldrich) |
| 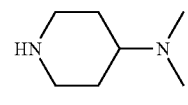 (935) (Aldrich) |
| H₂N(CH₃)₂OCH₃ (159) (Aldrich) |
| 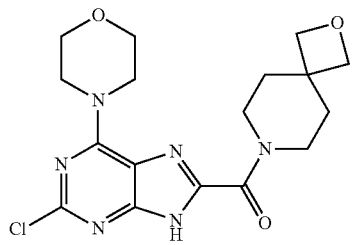 [SMILES: O=C(c1nc2c(N3CCOCC3)nc(Cl)nc2[nH]1)N1CCC2(CC1)COC2] (900) (Alfa aiser) |

To a solution of 2-chloro-6-(morpholin-4-yl)-9H-purine-8-carboxylic acid (1 equiv.) was added thionylchloride (2.5 mL) and catalytic amount of dimethylformamide, heated to 60-70° C. for 2 hours. The reaction mixture was evaporated under vacuum to give the residue. To the residue dichloromethane (20 mL) was added to which amine compound 1b shown above (2 equiv.) and triethylamine (6 equiv.) were added at 0° C., the reaction mixture was stirred at room temperature for 2 hours. The reaction mixture was diluted with dichloromethane (300 to 900 mL) and washed with water (100 to 300 mL). The organic layer was dried over anhydrous sodium sulfate and concentrated under vacuum, followed by purification by column chromatography using methanol and dichloromethane (5 to 15% methanol) as eluent.

Reference Example 7

Following the above procedure, [5-chloro-7-(morpholin-4-yl)-3H-imidazo[4,5-b]pyridin-2-yl][4-(morpholin-4-yl)piperidin-1-yl]methanone (2 g) was prepared using 5-chloro-7-(morpholin-4-yl)-3H-imidazo[4,5-b]pyridine-2-carboxylic acid (3.4 g, 12 mmole), thionyl chloride (17 mL), dichloromethane (100 mL) 4-morpholinopiperidine (4.08 g, 24 mmole) and triethylamine (6.55 mL, 48.05 mmole).

[Reference Example 8] Synthesis of [2-chloro-6-(morpholin-4-yl)-9H-purin-8-yl](2-oxa-7-azaspiro[3.5]non-7-yl)methanone To a solution of ethyl 2-chloro-6-(morpholin-4-yl)-9H-purine-8-carboxylate (240 mg, 0.77 mmole) and 2-oxa-7-azaspiro[3.5]nonane (195.96 mg, 1.54 mmole) in tetrahydrofuran (10 mL), trimethyl aluminium (2M) in toluene (0.96 mL, 1.93 mmole) was added drop wise at room temperature. During the addition internal temperature of reaction gets increased. After complete addition reaction was vigorously refluxed at 110° C. for 2-3 hours. The reaction mixture was cooled to room temperature, and carefully quenched using drop wise addition of methanol, followed by addition of dichloromethane (100 mL). Water (50 mL) was added and stirred for 10 minutes, organic layer was separated. Aqueous layer was extracted using dichloromethane (200 mL thrice). The combined organic extracts were dried over anhydrous sodium sulfate and concentrated under vacuum to obtain crude product, which upon purification by column chromatography (Combiflash) using methanol and dichloromethane (5% methanol) as gradient system gave 170 mg of the title compound.

¹H NMR (400 MHz, DMSO-d₆) δ ppm: 13.69-13.94 (m, 1H), 4.35 (s, 4H), 3.99 (br. s., 2H), 3.69-3.80 (m, 4H), 3.59-4.5 (br. s., 4H), 3.59 (br. s., 2H), 1.86 (d, J=5.52 Hz, 4H).

In a similar fashion, the following compounds were prepared.

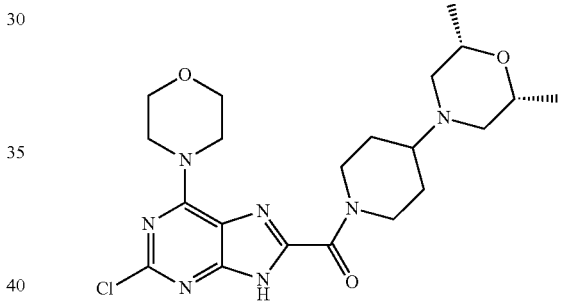

¹H NMR (400 MHz, DMSO-d₆) δ ppm: 13.69-14.07 (m, 1H), 4.88 (d, J=13.05 Hz, 1H), 4.47 (d, J=13.55 Hz, 1H), 3.82-4.35 (m, 4H), 3.73 (t, J=4.39 Hz, 5H), 3.45-3.57 (m, 2H), 3.21 (t, 1H), 2.82-2.92 (m, 1H), 2.74 (d, J=10.54 Hz, 2H), 1.75-1.91 (m, 4H), 1.31-1.50 (m, 2H), 1.04 (d, J=6.27 Hz, 6H).

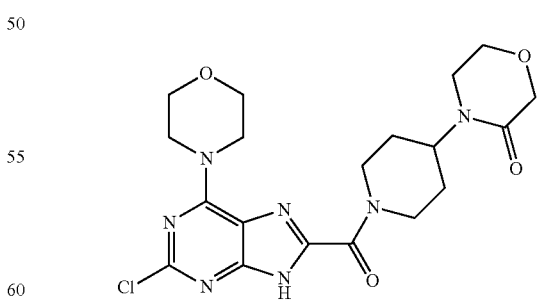

¹H NMR (400 MHz, DMSO-d₆) δ ppm: 13.74-14.06 (m, 1H), 4.89-5.21 (m, 1H), 4.51-4.67 (m, 2H), 4.11-4.47 (m, 4H), 4.04 (s, 2H), 3.80 (t, J=5.02 Hz, 2H), 3.73 (t, J=4.52 Hz, 4H), 3.25 (d, J=4.52 Hz, 3H), 2.83-2.98 (m, 1H), 1.69 (br. s., 4H).

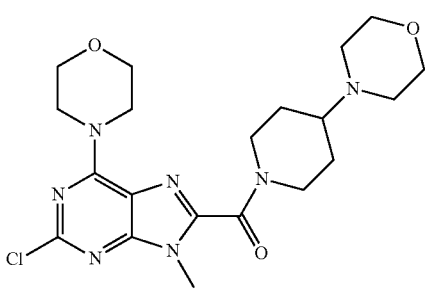 [SMILES: Cn1c(C(=O)N2CCC(N3CCOCC3)CC2)nc2c(N3CCOCC3)nc(Cl)nc21]

¹H NMR (400 MHz, DMSO-d₆) δ ppm: 4.41-4.49 (m, 1H), 4.20-4.41 (m, 2H), 4.07-4.16 (m, 1H), 3.79-4.05 (m, 2H), 3.71-3.76 (m, 5H), 3.70 (s, 3H), 3.51-3.60 (m, 4H), 3.10-3.21 (m, 1H), 2.86-2.98 (m, 1H), 2.42-2.49 (m, 4H), 1.75-1.98 (m, 2H), 1.34-1.49 (m, 2H).

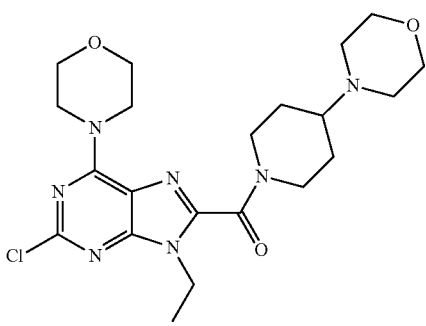 [SMILES: CCn1c(C(=O)N2CCC(N3CCOCC3)CC2)nc2c(N3CCOCC3)nc(Cl)nc21]

¹H NMR (400 MHz, DMSO-d₆) δ ppm: 4.41-4.49 (m, 1H), 4.40-4.52 (t, 2H), 4.20-4.41 (m, 2H), 4.07-4.16 (m, 1H), 3.79-4.05 (m, 2H), 3.71-3.76 (m, 5H), 3.51-3.60 (m, 4H), 3.10-3.21 (m, 1H), 2.86-2.98 (m, 1H), 2.42-2.49 (m, 4H), 1.75-1.98 (m, 2H), 1.34-1.49 (m, 2H), 1.32 (q, 2H).

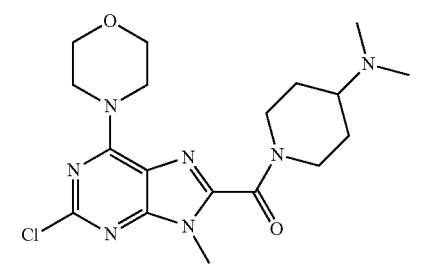 [SMILES: CN(C)C1CCN(C(=O)c2nc3c(N4CCOCC4)nc(Cl)nc3n2C)CC1]

¹H NMR (400 MHz, DMSO-d₆) δ ppm: 4.41-4.47 (m, 1H), 4.22-4.38 (m, 2H), 4.07-4.14 (m, 1H), 3.77-4.02 (m, 2H), 3.71-3.75 (m, 4H), 3.71 (s, 3H), 3.10-3.21 (m, 1H), 2.84-2.97 (m, 1H), 2.34-2.46 (m, 1H), 2.19 (s, 6H), 1.84-1.94 (m, 1H), 1.71-1.81 (m, 1H), 1.28-1.48 (m, 2H).

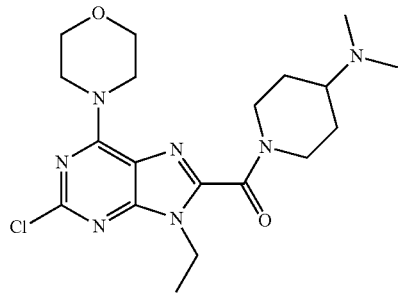 [SMILES: CCn1c(C(=O)N2CCC(N(C)C)CC2)nc2c(N3CCOCC3)nc(Cl)nc21]

¹H NMR (400 MHz, DMSO-d₆) δ ppm: 4.41-4.49 (m, 1H), 4.27-4.40 (m, 2H), 4.19 (d, J=7.28 Hz, 2H), 4.00-4.07 (m, 2H), 3.78-4.00 (m, 1H), 3.73 (t, J=4.39 Hz, 4H), 3.09-3.21 (m, 1H), 2.89-3.00 (m, 1H), 2.33-2.45 (m, 1H), 2.18 (s, 6H), 1.83-1.94 (m, 1H), 1.71-1.81 (m, 1H), 1.34-1.42 (m, 2H), 1.32 (t, J=7.03 Hz, 3H).

[Reference Example 9] Synthesis of [5-chloro-3-methyl-7-(morpholin-4-yl)-3H-imidazo[4,5-b]pyridin-2-yl][4-(morpholin-4-yl)piperidin-1-yl]methanone

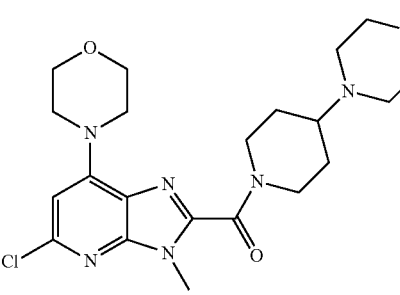

To a solution of [5-chloro-7-(morpholin-4-yl)-3H-imidazo[4,5-b]pyridin-2-yl][4-(morpholin-4-yl)piperidin-1-yl]methanone (800 mg, 1.7 mmole) in dimethylformamide (30 mL) was added methyl iodide (289.68 mg, 2.04 mmole, spectrochem) at 0° C. The reaction mixture was stirred at room temperature for 4 hours; water (50 mL) was added, extracted with dichloromethane (250 mL thrice). The combined organic layer was washed with water (200 mL thrice), dried over anhydrous sodium sulfate, and concentrated under vacuum, followed by purification by column chromatographic using dichloromethane and methanol (5% methanol) as eluent to obtain 400 mg of the title compound as white solid.

[Reference Example 10] Synthesis of [5-chloro-3-methyl-7-(morpholin-4-yl)-3H-imidazo[4,5-b]pyridin-2-yl][4-(dimethylamino)piperidin-1-yl]methanone

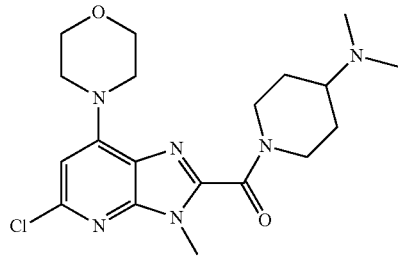 [SMILES: CN(C)C1CCN(C(=O)c2nc3c(N4CCOCC4)cc(Cl)nc3n2C)CC1]

Step a: Synthesis of ethyl 5-chloro-7-(morpholin-4-yl)-3H-imidazo[4,5-b]pyridine-2-carboxylate

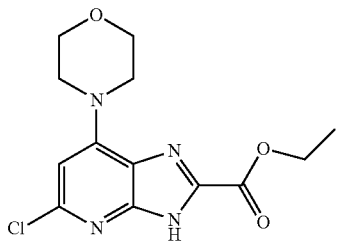 [SMILES: CCOC(=O)c1nc2c(N3CCOCC3)cc(Cl)nc2[nH]1]

To a solution of ethyl 5-chloro-7-(morpholin-4-yl)-3-(tetrahydro-2H-pyran-2-yl)-3H-imidazo[4,5-b]pyridine-2-carboxylate (1.4 g, 3.54 mmole) in ethanol (14 mL) was added p-toluene sulfonic acid (670 mg, 3.54 mmole) and the reaction mixture was stirred for 15 minutes at 140° C. under microwave condition. Saturated sodium bicarbonate (50 mL) was added, extracted with ethyl acetate (250 mL thrice). The combined organic extracts were dried over anhydrous sodium sulfate, concentrated under vacuum to obtain 980 mg of the title compound.

$^1$H NMR (400 MHz, DMSO-$d_6$) δ ppm: 13.82-14.11 (m, 1H), 6.58 (s, 1H), 4.39 (d, J=7.07 Hz, 2H), 3.95 (br. s., 4H), 3.73-3.79 (m, 4H), 1.34 (t, J=7.07 Hz, 3H).

Step b: Synthesis of ethyl 5-chloro-3-methyl-7-(morpholin-4-yl)-3H-imidazo[4,5-b]pyridine-2-carboxylate

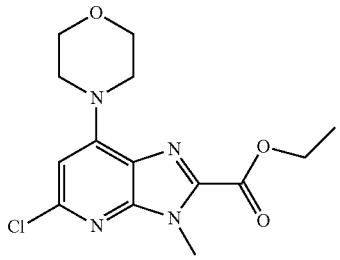 [SMILES: CCOC(=O)c1nc2c(N3CCOCC3)cc(Cl)nc2n1C]

To a solution of ethyl 5-chloro-7-(morpholin-4-yl)-3H-imidazo[4,5-b]pyridine-2-carboxylate (960 mg, 3.1 mmole) in acetone (16 mL) was added methyl iodide (886 mg, 6.2 mmole) and potassium carbonate (855 mg, 6.2 mmole). The reaction mixture was stirred for overnight at room temperature. The reaction mixture was filtered and concentrated to dryness and purified by column chromatography (50% ethyl acetate in hexane to pure ethyl acetate) to obtain 820 mg of the title compound.

$^1$H NMR (400 MHz, DMSO-$d_6$) δ ppm: 6.65 (s, 1H), 4.35-4.46 (m, 2H), 3.93-4.01 (m, 7H), 3.76 (d, J=4.55 Hz, 4H), 1.34 (s, 3H).

Step c: Synthesis of [5-chloro-3-methyl-7-(morpholin-4-yl)-3H-imidazo[4,5-b]pyridin-2-yl][4-(dimethylamino)piperidin-1-yl]methanone To a solution of ethyl 5-chloro-3-methyl-7-(morpholin-4-yl)-3H-imidazo[4,5-b]pyridine-2-carboxylate (380 mg, 1.17 mmole) and 4-N,N-dimethyl piperidine (300 mg, 2.34 mmole) in tetrahydrofuran (10 mL) was added trimethyl aluminium (1.2 mL, 2.34 mmole) at 0° C. and the reaction mixture refluxed at 80° C. for 18 hours. The reaction mixture was cooled, methanol (5 mL) was added, concentrated under vacuum to dryness, and purified by column chromatography using methanol and dichloromethane (5% methanol) to obtain 410 mg of the title compound.

[Reference Example 11] Synthesis of 2-chloro-9-methyl-6-(morpholin-4-yl)-9H-purine-8-carboxylic acid

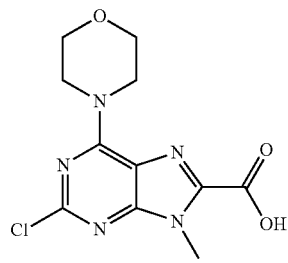 [SMILES: Cn1c(C(=O)O)nc2c(N3CCOCC3)nc(Cl)nc21]

Step a: Synthesis of 2-chloro-6-(morpholin-4-yl)-9H-purine

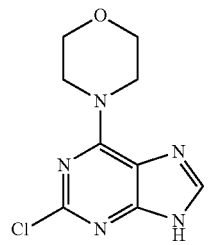 [SMILES: Clc1nc(N2CCOCC2)c2nc[nH]c2n1]

To a solution of 2,6-dichloro-9H-purine (20 g, 105.82 mmole) in ethanol (200 mL), was added morpholine (20.49 g, 232.80 mmole) at room temperature and refluxed for 1 hour at 80° C. The reaction mixture was cooled to room temperature, solvent was removed under vacuum, and water (300 mL) was added and extracted with dichloromethane (300 mL×3). The combined organic extracts (900 mL) were dried over anhydrous sodium sulfate, and concentrated under vacuum to dryness to obtain 23 g of 2-chloro-6-(morpholin-4-yl)-9H-purine.

Step b: Synthesis of 2-chloro-9-methyl-6-(morpholin-4-yl)-9H-purine

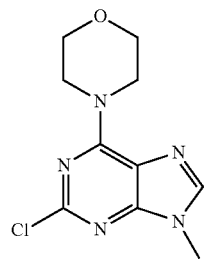 [SMILES: Cn1cnc2c(N3CCOCC3)nc(Cl)nc21]

To a solution of 2-chloro-6-(morpholin-4-yl)-9H-purine (4 g, 16.73 mmole) in acetone (60 mL) was added methyl iodide (2.14 mL, 33.47 mmole) at 0° C. and reflux for overnight. The reaction mixture was cooled to room temperature and filtered. The residue was washed with hexane (100 mL) and dried under vacuum to obtain 3.9 g of the title compound.

$^1$H NMR (400 MHz, DMSO-d$_6$) δ ppm: 8.17 (s, 1H), 3.85-4.94 (m, 4H), 3.60-3.82 (m, 4H), 3.60-3.82 (s, 3H).

Similarly, 2-chloro-9-ethyl-6-(morpholin-4-yl)-9H-purine was prepared.

$^1$H NMR (400 MHz, DMSO-d$_6$) δ ppm: 8.24 (s, 1H), 4.15 (d, J=7.28 Hz, 2H), 3.75-4.15- (m, 4H) 3.64-3.78 (m, 4H), 1.37 (t, J=7.28 Hz, 3H).

Step c: Synthesis of 2-chloro-9-methyl-6-(morpholin-4-yl)-9H-purine-8-carbaldehyde

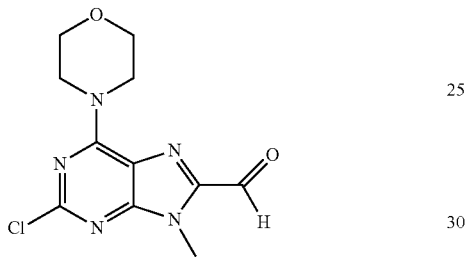

To a mixture of 2-chloro-9-methyl-6-(morpholin-4-yl)-9H-purine (3.3 g, 13.04 mmole) in tetrahydrofuran (80 mL) was added tetramethylethylenediamine (4.3 mL, 26.08 mmole) at room temperature and cooled to −78° C. After attaining the temperature, n-butyl lithium (2.5M, 13 mL, 32.60 mmol) was added drop wise, stirred for 60 minutes, followed by addition of dimethylformamide (2 mL, 26.08 mmole) at −78° C. and stirring was continued at same temperature for 2 hours. To the reaction mixture saturated ammonium chloride (100 mL) was added, extracted with ethyl acetate (300 mL thrice). The combined organic layer was dried over anhydrous sodium sulfate and concentrated under vacuum to obtain 3.1 g of the title compound.

$^1$H NMR (400 MHz, DMSO-d$_6$) δ ppm: 9.87 (s, 1H), 4.40-4.74 (m, 2H), 3.91-3.71 (m, 2H), 3.91 (s, 3H), 3.77 (br. s., 4H).

Similarly, 2-chloro-9-ethyl-6-(morpholin-4-yl)-9H-purine-8-carbaldehyde was prepared.

$^1$H NMR (400 MHz, DMSO-d$_6$) δ ppm: 9.86 (s, 1H), 4.52-4.72 (m, 2H), 4.45 (d, J=7.28 Hz, 2H), 3.82-3.99 (m, 2H), 3.77 (br. s., 4H), 1.31 (t, J=7.15 Hz, 3H).

Step d: Synthesis of 2-chloro-9-methyl-6-(morpholin-4-yl)-9H-purine-8-carboxylic acid To a solution of 2-chloro-9-methyl-6-(morpholin-4-yl)-9H-purine-8-carbaldehyde (3.3 g, 11.74 mmole) in ethanol (30 mL) was added silver nitrate (2.5 g, 14.79 mmole) and sodium hydroxide solution (1.5N, 40 mL) and the reaction mixture was stirred at room temperature for 12 hours. The reaction mixture was filtered over celite pad, concentrated and the residue was taken in water and basified by adding sodium hydroxide (1N), extracted with dichloromethane (60 mL twice), the aqueous layer was acidified with concentrated hydrochloric acid, the volume was reduced to half by evaporation under vacuum to form the precipitate which was filtered and dried to obtain 2 g of the title compound.

$^1$H NMR (400 MHz, DMSO-d$_6$) δ ppm: 12.70-15.36 (m, 1H), 3.93-4.85 (m, 4H), 3.89 (s, 3H), 3.74 (br. s., 4H).

Similarly, 2-chloro-9-ethyl-6-(morpholin-4-yl)-9H-purine-8-carboxylic acid was prepared.

$^1$H NMR (400 MHz, DMSO-d$_6$) δ ppm: 12.70-15.36 (m, 1H), 4.53-4.71 (m, 2H), 4.40-4.52 (t, 2H), 3.82-4.07 (m, 2H), 3.74 (br. s., 4H), 1.32 (q, 2H).

Following the procedure described above, 2-chloro-9-methyl-6-(morpholin-4-yl)-9H-purine-8-carboxylic acid was converted into amide compound 3a using thionyl chloride (17 mL), dimethylformamide (catalytic amount), amine compound 1b (2 equiv.) and triethylamine (6 equiv.)

Synthesis of Amide Compound 4a

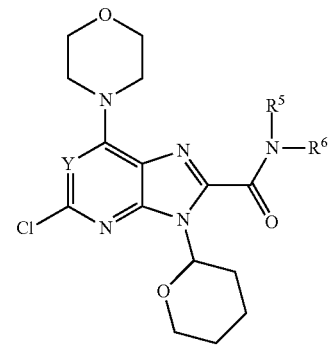

4a

Step a: Synthesis of N-oxide of 3H-imidazo[4,5-b]pyridine

To a solution of 1-deazapurine (50 g, 420 mmol) in ethyl acetate (450 mL) was added m-chloroperoxybenzoic acid (55%, 171 g, 546 mmol) portion wise at 0° C. and the reaction mixture was stirred at room temperature for 24 hours. The reaction mixture was diluted with hexane (500 mL) and filtered. The solid formed was dried under vacuum to obtain 75.86 g of the title compound.

$^1$H NMR (400 MHz, DMSO-d$_6$) δ ppm: 8.43 (s, 1H), 8.21 (d, J=6.27 Hz, 1H), 7.63 (d, J=8.03 Hz, 1H), 7.23 (dd, J=6.27, 8.28 Hz, 1H).

Step b: Synthesis of
7-chloro-3H-imidazo[4,5-b]pyridine

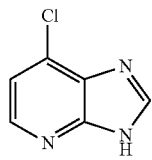

To a stirring phosphoryl chloride (350 mL, 3.76 mole) in round bottom flask was added N-oxide of 3H-imidazo[4,5-b]pyridine (47 g, 348 mmol) portion wise at 0° C. and the reaction mixture was heated at 115° C. for 24 hours. The reaction mixture was cooled to room temperature and solvent was evaporated under reduced pressure to dryness. The residue was poured over crushed ice and was neutralized with saturated solution of sodium bicarbonate and extracted with ethyl acetate (1 L twice), washed with water (500 mL), brine (500 mL) and dried over anhydrous sodium sulfate, and concentrated under vacuum to obtain 31.5 g of the title compound.

$^1$H NMR (400 MHz, DMSO-d$_6$) δ ppm: 8.52 (d, J=11.29 Hz, 2H), 8.30 (d, J=5.02 Hz, 1H), 8.08 (d, J=8.28 Hz, 1H), 7.40 (d, J=5.27 Hz, 1H), 7.31 (d, J=8.28 Hz, 1H).

Step c: Synthesis of N-oxide of
7-chloro-3H-imidazo[4,5-b]pyridine

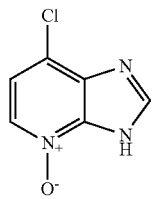 [SMILES: [O-][n+]1ccc(Cl)c2nc[nH]c21]

To a solution of 7-chloro-3H-imidazo[4,5-b]pyridine (31.3 g, 204 mmol) in ethyl acetate (450 mL) was added m-chloroperoxybenzoic acid (55%, 89.5 g, 286 mmol) portion wise at 0° C. and the reaction mixture was stirred at room temperature for 7 hours. The reaction mixture was diluted with hexane (500 mL) and filtered. The solid formed was dried under vacuum to obtain 48.3 g of the title compound.

$^1$H NMR (400 MHz, DMSO-d$_6$) δ ppm: 8.52 (s, 1H), 8.23 (d, J=6.78 Hz, 1H), 7.87-7.93 (m, 2H), 7.68-7.75 (m, 1H), 7.52-7.59 (m, 1H), 7.40 (d, J=6.78 Hz, 1H).

Step c: Synthesis of
5,7-dichloro-3H-imidazo[4,5-b]pyridine

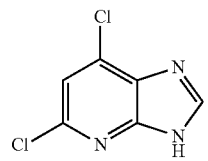 [SMILES: Clc1cc(Cl)c2nc[nH]c2n1]

To a stirring phosphoryl chloride (240 mL, 262 mmol) in round bottom flask was added N-oxide of 7-chloro-3H-imidazo[4,5-b]pyridine (48 g, 284 mmol) portion wise at 0° C. and the reaction mixture was heated at 115° C. for 24 hours. The reaction mixture was cooled to room temperature. The solvent was evaporated under reduced pressure to dryness. The residue was poured over crushed ice and was neutralized with saturated solution of sodium bicarbonate and extracted with ethyl acetate (1 L twice), washed with water (500 mL), brine (500 mL) and dried over anhydrous sodium sulfate, filtered, concentrated under vacuum, and purified by silica gel column chromatography (100-200 mesh) using methanol and dichloromethane (5% methanol) as eluent to obtain 22.8 g of the title compound.

$^1$H NMR (400 MHz, DMSO-d$_6$) δ ppm: 8.59 (s, 1H), 7.90 (d, J=2.01 Hz, 1H), 7.59 (s, 1H).

Step d: Synthesis of 5-chloro-7-(morpholin-4-yl)-
3H-imidazo[4,5-b]pyridine

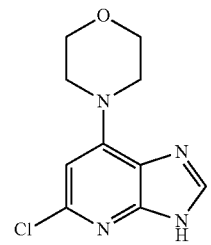 [SMILES: Clc1cc(N2CCOCC2)c2nc[nH]c2n1]

To a solution of 5,7-dichloro-3H-imidazo[4,5-b]pyridine (17.75 g, 94.4 mmol) in ethanol (180 mL) was added morpholine (82.1 g, 944 mmol) and the reaction mixture was heated at 140° C. for 18 hours in steel bomb. The reaction mixture was cooled to room temperature, poured in water and the precipitate formed were filtered and dried under vacuum to 16.2 g of the title compound.

$^1$H NMR (400 MHz, DMSO-d$_6$) δ ppm: 12.72-13.12 (m, 1H), 8.11 (s, 1H), 6.50 (s, 1H), 3.88 (d, J=4.52 Hz, 4H), 3.70-3.76 (m, 4H).

Step e: Synthesis of 5-chloro-6-fluoro-7-(morpholin-4-yl)-3H-imidazo[4,5-b]pyridine

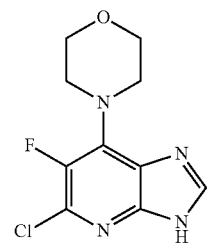 [SMILES: Fc1c(Cl)nc2[nH]cnc2c1N1CCOCC1]

To a solution of 5-chloro-7-(morpholin-4-yl)-3H-imidazo[4,5-b]pyridine (4 g, 16.74 mmol) in acetonitrile and water (9:1, 60 mL) was added selectfluor (14.8 g, 41.84 mmol), heated at 150° C. under microwave for 10 minutes. The reaction mixture was poured in saturated sodium bicarbonate (30 mL), extracted with ethyl acetate (100 mL twice), washed with water (50 mL), brine (50 mL) and dried over anhydrous sodium sulfate, concentrated under vacuum, and purified by column chromatography using methanol and dichloromethane (6% methanol) as eluent to obtain 1.15 g of the title compound (as crude compound).

Step f: Synthesis of 5-chloro-6-fluoro-7-(morpholin-4-yl)-3-(tetrahydro-2H-pyran-2-yl)-3H-imidazo[4,5-b]pyridine

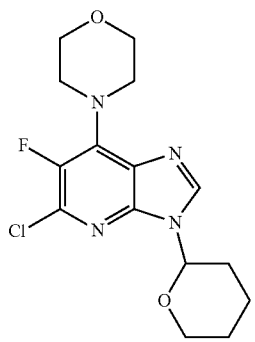 [SMILES: Fc1c(Cl)nc2c(ncn2C2CCCCO2)c1N1CCOCC1]

To a solution of compound (1.13 g, 4.40 mmol, step e) in ethyl acetate (15 mL), was added p-toluene sulfonic acid (170 mg, 0.88 mmol) and 3,4-dihydro-2H-pyran (923 mg, 10.99 mmol) and the reaction mixture was refluxed for 12 hours. The reaction mixture was cooled to room temperature, diluted with ethyl acetate (300 mL) washed with saturated sodium bicarbonate (100 mL), water (100 mL), brine (100 mL) and dried over anhydrous sodium sulfate and concentrated under vacuum. The residue was purified by column chromatography using methanol and dichloromethane (1% methanol) as eluent to obtain 650 mg of crude mixture (F:Cl:H).

Step g: Synthesis of ethyl 5-chloro-6-fluoro-7-(morpholin-4-yl)-3-(tetrahydro-2H-pyran-2-yl)-3H-imidazo[4,5-b]pyridine-2-carboxylate

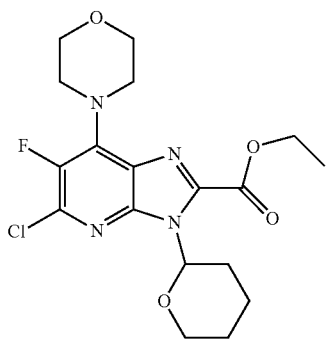 [SMILES: CCOC(=O)c1nc2c(N3CCOCC3)c(F)c(Cl)nc2n1C1CCCCO1]

To a solution of 5-chloro-6-fluoro-7-(morpholin-4-yl)-3-(tetrahydro-2H-pyran-2-yl)-3H-imidazo[4,5-b]pyridine (5.4 g, 15.81 mmol) in tetrahydrofuran (150 mL) was added n-butyl lithium (1.6 M, 14.85 mL, 23.76 mmol) at −78° C. and the reaction mixture was stirred for 1 hour at same temperature and further stirred for 1 hour at −40° C. The reaction mixture was poured into the solution of ethyl chloroformate (13.68 g, 126.72 mmol) in tetrahydrofuran at −78° C. and the reaction mixture was stirred for 10 minutes. Then it was poured into the saturated ammonium chloride (75 mL) and extracted with ethyl acetate (400 mL thrice), washed with water (200 mL), brine (200 mL), dried over anhydrous sodium sulfate, and concentrated under vacuum. The compound was purified by column chromatography using ethyl acetate and hexane (1:1) as eluent to obtain 1.9 g of the title compound and ethyl 5-chloro-6-chloro-7-(morpholin-4-yl)-3-(tetrahydro-2H-pyran-2-yl)-3H-imidazo[4,5-b]pyridine-2-carboxylate (0.91 g).

Step h: Synthesis of Compound 4a (Wherein Y is CF and CCl)

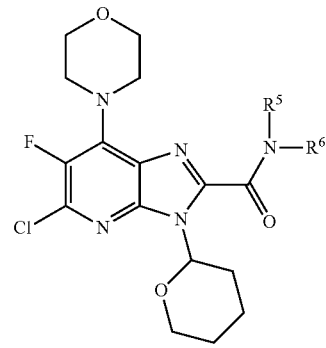

To a solution of compound 1b (2.5 equiv.) in tetrahydrofuran (10 to 70 mL) was added aluminium trimethyl (2.5 equiv.) at −10° C. and the reaction mixture was stirred at room temperature for 30 minutes. Then this solution was added to a solution of ethyl 5-chloro-6-fluoro-7-(morpholin-4-yl)-3-(tetrahydro-2H-pyran-2-yl)-3H-imidazo[4,5-b]pyridine-2-carboxylate in tetrahydrofuran (1 equiv in 10 to 70 mL) and the reaction mixture was refluxed at 100° C. for 20 hours. The reaction mixture was cooled to room temperature and diluted with ethyl acetate (50 to 200 mL) and methanol (5 to 25 mL). It was then partitioned between water (30 to 150 mL) and ethyl acetate (200 to 600 mL). The organic layer was separated, dried over anhydrous sodium sulfate, concentrated under vacuum, and purified by flash chromatography using methanol and dichloromethane (5 to 15% methanol) as eluent to obtain the title compounds.

[Reference Example 12] Synthesis of [5,6-dichloro-7-(morpholin-4-yl)-3-(tetrahydro-2H-pyran-2-yl)-3H-imidazo[4,5-b]pyridin-2-yl][4-(morpholin-4-yl)piperidin-1-yl]methanone

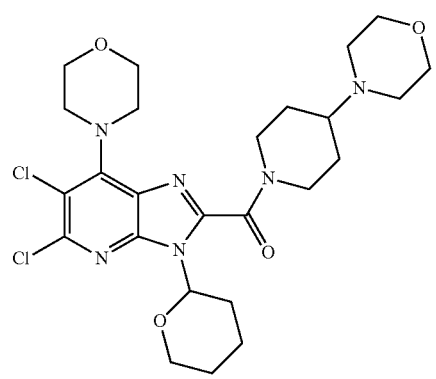 [SMILES: O=C(c1nc2c(N3CCOCC3)c(Cl)c(Cl)nc2n1C1CCCCO1)N1CCC(N2CCOCC2)CC1]

To a solution of 4-morpholino piperidine (2.5 equiv.) in tetrahydrofuran (8 mL), was added trimethyl aluminium (2.5 equiv.) at −10° C. and the reaction mixture was stirred at room temperature for 30 minutes. Then this solution was added to a solution of ethyl 5,6-dichloro-7-(morpholin-4-yl)-3-(tetrahydro-2H-pyran-2-yl)-3H-imidazo[4,5-b]pyridine-2-carboxylate in tetrahydrofuran (1 equiv., 8 mL) and the reaction mixture was refluxed at 100° C. for 20 hours. The reaction mixture was cooled to room temperature and diluted with ethyl acetate (50 mL) and methanol (5 mL). It was then partitioned between water and ethyl acetate. The organic layer was separated, dried over anhydrous sodium sulfate, concentrated under vacuum and purified by flash chromatography using methanol and dichloromethane as eluent to obtain the title compound.

$^1$H NMR (400 MHz, DMSO-d$_6$) □ 5.58-5.74 (m, 1H), 4.36-4.53 (m, 1H), 3.94-4.06 (m, 1H), 3.72-3.78 (m, 4H), 3.64-3.69 (m, 4H), 3.56 (br. s., 5H), 2.85-3.14 (m, 2H), 2.46 (d, J=3.76 Hz, 6H), 1.80-1.97 (m, 3H), 1.61-1.76 (m, 2H), 1.29-1.58 (m, 4H).

[Reference Example 13] Synthesis of [5-chloro-6-methyl-7-(morpholin-4-yl)-3-(tetrahydro-2H-pyran-2-yl)-3H-imidazo[4,5-b]pyridin-2-yl][4-(morpholin-4-yl)piperidin-1-yl]methanone

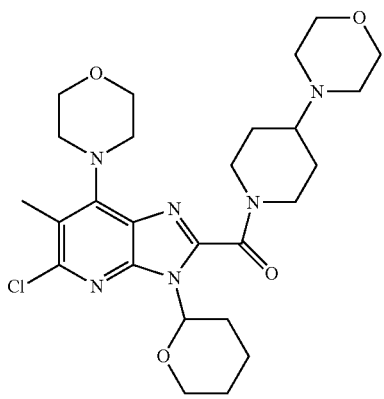 [SMILES: Cc1c(Cl)nc2c(nc(C(=O)N3CCC(N4CCOCC4)CC3)n2C2CCCCO2)c1N1CCOCC1]

Step a: Synthesis of ethyl 6-bromo-5-chloro-7-(morpholin-4-yl)-3-(tetrahydro-2H-pyran-2-yl)-3H-imidazo[4,5-b]pyridine-2-carboxylate

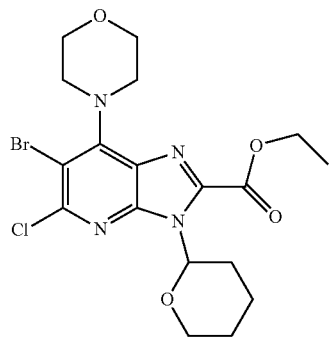

To a solution of ethyl 5-chloro-7-(morpholin-4-yl)-3-(tetrahydro-2H-pyran-2-yl)-3H-imidazo[4,5-b]pyridine-2-carboxylate (2.75 g, 6.96 mmol) in dimethylformamide (22 mL), was added N-bromosuccinimide (1.24 g, 6.96 mmol) in dimethylformamide (8 mL) drop wise at 0° C. and allowed to stir at room temperature for 90 minutes. Water (50 mL) was added and extracted with ethyl acetate (250 mL thrice). The combined organic extracts were dried over anhydrous sodium sulfate, concentrated under vacuum and purified by flash chromatography using ethyl acetate and hexane (1:1) as eluent to obtain 2.65 g of the title compound.

$^1$H NMR (400 MHz, CDCl$_3$) δ ppm: 6.22 (m, 1H), 4.42-4.56 (m, 2H), 4.15 (m, 1H), 3.85-3.95 (m, 4H), 3.66-3.82 (m, 5H), 2.90-3.02 (m, 1H), 2.02-2.11 (m, 1H), 1.92 (m, 1H), 1.67-1.85 (m, 2H), 1.57 (m, 2H), 1.47 (m, 3H). Mass Spectrum (ESI): m/z 472.95 (M+H) and 474.93 (M+2H).

Step b: Synthesis of ethyl 5-chloro-6-methyl-7-(morpholin-4-yl)-3-(tetrahydro-2H-pyran-2-yl)-3H-imidazo[4,5-b]pyridine-2-carboxylate

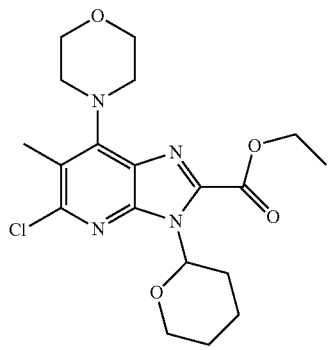 [SMILES: CCOC(=O)c1nc2c(N3CCOCC3)c(C)c(Cl)nc2n1C1CCCCO1]

To a solution of ethyl 6-bromo-5-chloro-7-(morpholin-4-yl)-3-(tetrahydro-2H-pyran-2-yl)-3H-imidazo[4,5-b]pyridine-2-carboxylate (250 mg, 0.52 mmol) in 1,2-dichloroethane (5 mL), was added methyl boronic acid (126 mg, 2.1 mmol) and cesium carbonate (514 mg, 1.58 mmol) and the reaction mixture was purged with Argon for 10 minutes. Then tetrakis(triphenylphosphine)palladium(0) (61 mg, 0.05 mmol) was added and the mixture was heated at 140° C. for 90 minutes. The reaction mixture was cooled, diluted with dichloromethane (50 mL), and concentrated under vacuum to dryness. The residue was purified by flash chromatography using methanol and dichloromethane (5% methanol) as eluent to obtain 110 mg of the title compound.

$^1$H NMR (400 MHz, CDCl$_3$) δ ppm: 6.20-6.27 (m, 1H), 4.48 (m, 2H), 4.10-4.18 (m, 1H), 3.83-3.92 (m, 4H), 3.67-3.76 (m, 1H), 3.54-3.63 (m, 4H), 2.95-3.08 (m, 1H), 2.36 (s, 3H), 2.02-2.11 (m, 1H), 1.87-1.95 (m, 1H), 1.67-1.85 (m, 2H), 1.57-1.61 (m, 1H), 1.47 (m, 3H). Mass Spectrum (ESI): m/z 409.08 (M+H) and 411.06 (M+2H).

Step c: Synthesis of [5-chloro-6-methyl-7-(morpholin-4-yl)-3-(tetrahydro-2H-pyran-2-yl)-3H-imidazo[4,5-b]pyridin-2-yl][4-(morpholin-4-yl)piperidin-1-yl]methanone To a solution of 4-morpholino piperidine (1.06 g, 6.23 mmol) in tetrahydrofuran (10 mL), was added aluminium trimethyl (3.1 mL, 6.23 mmol) at −10° C. and the reaction mixture was stirred at room temperature for 30 minutes. Then this solution was added to a solution of ethyl 5-chloro-6-methyl-7-(morpholin-4-yl)-3-(tetrahydro-2H-pyran-2-yl)-

3H-imidazo[4,5-b]pyridine-2-carboxylate (850 mg, 2.08 mmol) in tetrahydrofuran (5 mL) and the reaction mixture was refluxed at 100° C. for 20 hours. The reaction mixture was cooled to room temperature and diluted with ethyl acetate (50 mL) and methanol (5 mL). It was then partitioned between water (50 mL) and ethyl acetate (400 mL). The organic layer was separated, dried over anhydrous sodium sulfate, concentrated under vacuum, and purified by flash chromatography using methanol and dichloromethane (5% methanol) as eluent to obtain 750 mg of the title compound as off white solid.

$^1$H NMR (400 MHz, CDCl$_3$) δ ppm: 5.76-5.90 (m, 1H), 4.62-4.81 (m, 1H), 4.02-4.13 (m, 1H), 3.85 (m, 4H), 3.64-3.77 (m, 6H), 3.46-3.59 (m, 4H), 2.82-3.13 (m, 2H), 2.61-2.74 (m, 1H), 2.55 (br. s., 4H), 2.41-2.49 (m, 1H), 2.36 (s, 3H), 1.93-2.06 (m, 3H), 1.63-1.82 (m, 3H), 1.45-1.55 (m, 3H). Mass Spectrum (ESI): m/z 533.18 (M+H) and 535.11 (M+2H).

Synthesis of Amine Compound 1b

[Reference Example 15] Synthesis of 2-oxa-7-azaspiro[3.5]nonane

Step a: Synthesis of Compound 15b

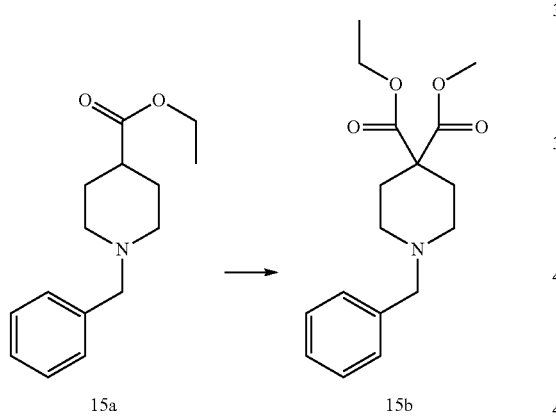

15a → 15b

To a solution of diisopropylamine (1.63 g, 16.18 mmol) in tetrahydrofuran (20 mL) was added n-butyllithium (1.6 M in hexane, 10 mL, 16.18 mmol) at 0° C. and stirred for 30 minutes at room temperature, followed by cooling at 0° C. This freshly prepared lithium diisopropylamide was added in a solution of compound 15a (2 g, 8.097 mmol) in tetrahydrofuran (40 mL) drop wise at −78° C. and stirred at −40° C. for 1 hour. The reaction mixture was cooled to −78° C.; methyl chloroformate (0.841 g, 8.90 mmole) was added. Stirring was continued at same temperature for 2 hours and at room temperature for 3-4 hours. Saturated ammonium chloride (100 mL) was added and extracted with ethyl acetate (100 mL thrice). The combined organic layer was dried over anhydrous sodium sulfate and concentrated under vacuum to obtain 2.1 g of compound 15b.

$^1$H NMR (400 MHz, DMSO-d$_6$) δ ppm: 7.06-7.45 (m, 5H), 4.13 (q, 2H), 3.63-3.69 (s, 3H), 3.41 (s, 2H), 2.33 (br. s., 4H), 1.99 (t, J=5.40 Hz, 4H), 1.02-1.35 (t, 3H).

Step b: Synthesis of Compound 15c

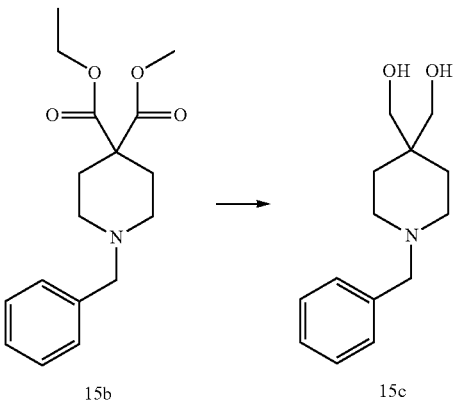 [SMILES: CCOC(=O)C1(C(=O)OC)CCN(Cc2ccccc2)CC1 ; OCC1(CO)CCN(Cc2ccccc2)CC1]

15b → 15c

To a solution of compound 15b (2.2 g, 7.189 mmol) in tetrahydrofuran (50 mL) was added lithium aluminum hydride (0.683 g, 17.97 mmol) in portion wise at 0° C. and stirred for 2-3 hours at room temperature. Then to this was added saturated sodium sulfate (100 mL) at 0° C. drop wise. The reaction mixture was filter over celite and filtrate was concentrated under vacuum to obtain 1.3 g of compound 15c.

$^1$H NMR (400 MHz, DMSO-d$_6$) δ ppm: 6.89-7.43 (m, 5H), 4.30 (br. s., 2H), 3.42 (br. s., 2H), 3.33 (br. s., 2H), 2.28 (br. s., 4H), 1.35 (br. s., 4H).

Step c: Synthesis of Compound 15d

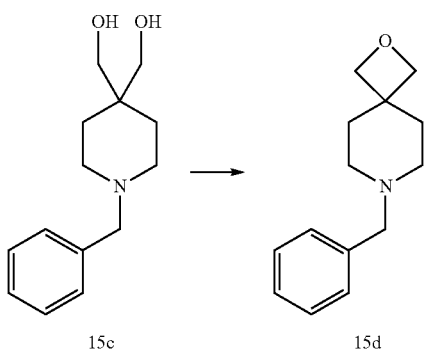 [SMILES: OCC1(CO)CCN(Cc2ccccc2)CC1 ; c1ccc(CN2CCC3(CC2)COC3)cc1]

15c → 15d

To a solution of compound 15c (2.8 g, 11.91 mmol) in tetrahydrofuran (60 mL) was added n-butyl lithium (1.6 M in hexane, 7.4 mL, 11.91 mmol) at 0° C. and stirred at same temperature for 30 minutes. To this was added a solution of p-toluene sulphonyl chloride (2.26 g, 11.91 mmol) in tetrahydrofuran (10 mL) drop wise and stirring was continued at 0° C. for 1-2 hours. Then to it was added n-butyl lithium (1.6 M in hexane, 7.4 mL, 11.91 mmol) and stirred for 30 minutes at same temperature and then stirred at 70° C. for 1 hour. The reaction mixture was cooled to room temperature and saturated ammonium chloride (100 mL) was added and extracted with ethyl acetate (100 mL twice). The combined organic layer was dried over anhydrous sodium sulfate and concentrated under vacuum to obtain 1.8 g of compound 15d.

¹H NMR (400 MHz, CDCl₃) δ ppm: 7.01-7.56 (m, 5H), 4.40 (s, 4H), 3.44 (s, 2H), 2.31 (br. s., 4H), 1.86 (t, J=5.14 Hz, 4H).

Step d: Synthesis of 2-oxa-7-azaspiro[3.5]nonane

To a solution of compound 15d (1.8 g, 8.29 mmol) in methanol (50 mL) was added palladium carbon (0.5 g) and stirred under hydrogen atmosphere (balloon pressure) at room temperature for 18-22 hours. The reaction mixture was filtered and filtrate was concentrated under vacuum to obtain 1 g of 2-oxa-7-azaspiro[3.5]nonane.

¹H NMR (400 MHz, CDCl₃) δ ppm: 4.26-4.59 (s, 4H), 2.63-2.88 (m, 4H), 1.73-1.96 (m, 4H).

[Reference Example 16] Synthesis of N-(piperidin-4-yl)acetamide

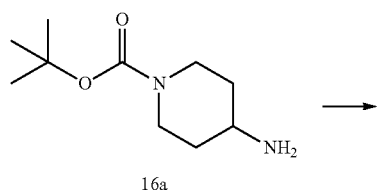

16a

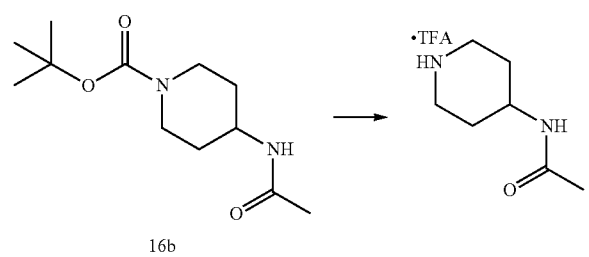

16b

To a solution of compound 16a (1 g, 5 mmol) in dichloromethane (15 mL), was added acetyl chloride (0.3 mL, 5.5 mmol) at 0° C. and allowed to stir at room temperature for overnight. The volatiles were removed under vacuum and water (30 mL) was added followed by saturated sodium bicarbonate (30 mL) and then extracted with ethyl acetate (250 mL thrice). The combined organic extracts were washed with brine (100 mL), separated dried over sodium sulphate and concentrated under vacuum to obtain 460 mg of compound 16b. To a solution of compound 16b (460 mg) in dichloromethane (10 mL) was added trifluoro acetic acid (1 mL) at room temperature and stirred for overnight. The volatiles were removed under vacuum and triturated using diethyl ether (50 mL). The precipitates were filtered and dried under vacuum to obtain 380 mg of N-(piperidin-4-yl) acetamide.

[Reference Example 17] Synthesis of N-(piperidin-4-yl)methanesulfonamide

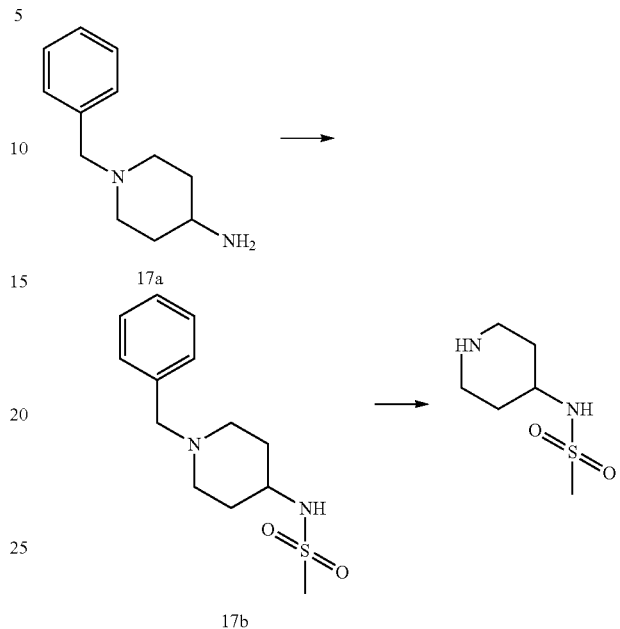

To a solution of compound 17a (1 g, 5.263 mmol) in dichloromethane (10 mL) was added triethylamine (1.07 mL, 7.81 mmol) at 0° C. followed by methane sulfonyl chloride (0.81 mL, 6.315 mmol) and allowed to stir at room temperature for overnight. The volatiles were removed under vacuum and water (30 mL) was added, and then extracted with dichloromethane (150 mL thrice). The combined organic extracts were washed with brine (75 mL), separated dried over sodium sulphate and concentrated under vacuum to obtain 430 mg of compound 17b. To a solution of this compound (430 mg) in methanol (15 mL) was added palladium carbon (250 mg) and stirred under hydrogen atmosphere (balloon pressure) at room temperature for overnight. The reaction mixture was filtered and filtrate was concentrated under vacuum to obtain 200 mg of N-(piperidin-4-yl)methanesulfonamide.

[Reference Example 18] Synthesis of 1-(methylsulfonyl)piperazine

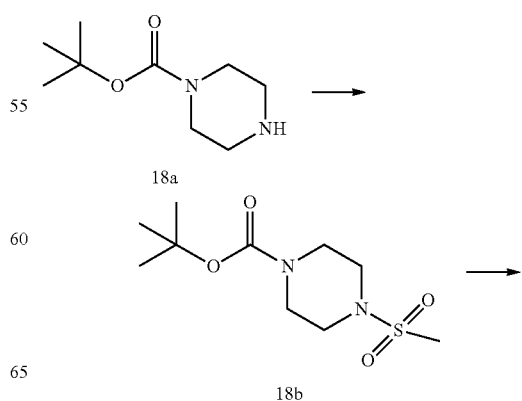

-continued

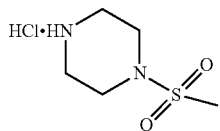

To a solution of compound 18a (2 g, 10.80 mmol) in dichloromethane (40 mL) was added triethylamine (3 mL, 21.60 mmol) at 0° C. followed by methane sulfonyl chloride (1 mL, 12.96 mmol) and allowed to stir at room temperature for overnight. The volatiles were removed under vacuum and water (50 mL) was added, followed by extraction with dichloromethane (300 mL thrice). The combined organic extracts were washed with brine (200 mL), separated dried over sodium sulphate and concentrated under vacuum to obtain 430 mg of compound 18b. To a solution of this compound (2 g, 7.56 mmol) in 1,4-dioxane (15 mL) was added 1,4-dioxane hydrochloric acid at 0° C. and allowed to stir at room temperature for overnight. The volatiles were removed under vacuum and triturated with diethyl ether (50 mL). The precipitates were filtered and dried under vacuum to obtain 1.7 g of 1-(methylsulfonyl)piperazine.

[Reference Example 19] Synthesis of 2-(piperidin-4-yl)propan-2-ol

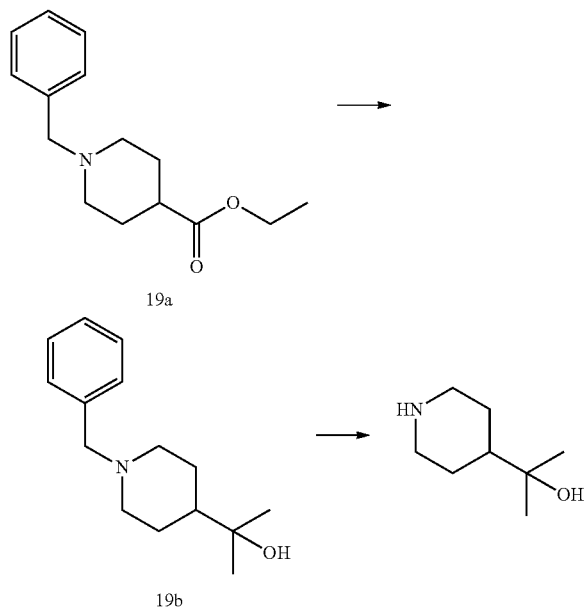

To a solution of compound 19a (10 g, 40.6 mmol) in tetrahydrofuran (100 mL) was added methyl magnesium bromide (54 mL, 162.4 mmol) drop wise at 0° C. and allowed to stir at room temperature for overnight. Saturated ammonium chloride (150 ml) was added to reaction mixture and extracted with ethyl acetate (300 mL thrice). The combined organic extracts dried over sodium sulphate and concentrated under vacuum to obtain 7.5 g of compound 19b. To a solution of this compound (7.5 g) in methanol (150 mL) was added palladium carbon (2 g) and stirred under hydrogen atmosphere (balloon pressure) at room temperature for overnight. The reaction mixture was filtered and filtrate was concentrated under vacuum to obtain 5.3 g of 2-(piperidin-4-yl)propan-2-ol.

[Reference Example 20] Synthesis of 1-(tetrahydro-2H-pyran-4-yl)piperazine

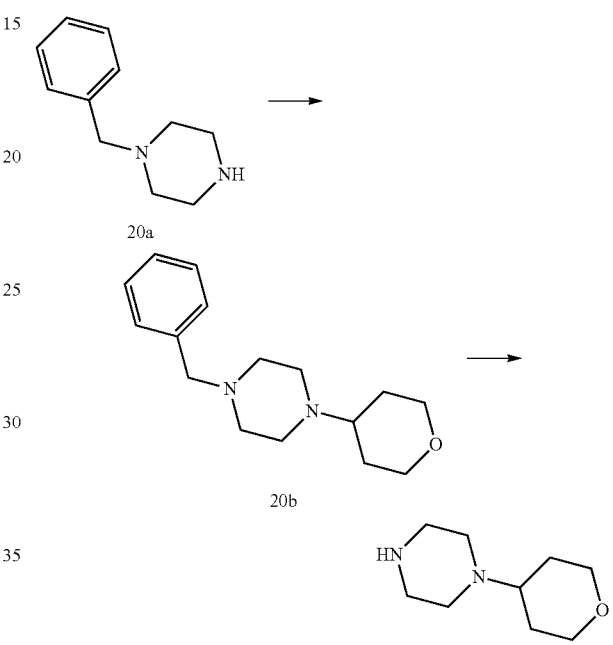

To a solution of compound 20a (12 g, 68.08 mmol) in tetrahydrofuran (200 mL), were added 4-tetrahydropyranone (13.632 g, 136.16 mmol) and p-toluene sulfonic acid (389 mg, 2.04 mmol), followed by addition of acetic acid (6 mL). Sodium triacetoxy borohydride (28.9 g, 136.16 mmol) was added portion wise at 0° C. and reaction mixture was allowed to stir at room temperature for 16 h. Saturated sodium bicarbonate (150 mL) was added and extracted with dichloromethane (300 mL thrice). The combined organic extracts were dried over anhydrous sodium sulfate and concentrated under vacuum to obtain the crude product, which upon purification by flash chromatography (5% methanol in dichloromethane as eluent) gave 12.5 g of compound 20b. To a solution of this compound (15 g) in methanol (200 mL) was added palladium carbon (3 g) and allowed to shake in Parr apparatus at hydrogen pressure (50 psi) for 6 hours at room temperature. The reaction mixture was filtered and washed with methanol. Filtrate was concentrated under vacuum to obtain 10 g of 1-(tetrahydro-2H-pyran-4-yl)piperazine. In a similar fashion, cis-2,6-dimethyl-4-(piperidin-4-yl)morpholine and 4-(piperidin-3-yl)morpholine were prepared.

[Reference Example 21] Synthesis of 2-methyl-2-(piperazin-1-yl)propanamide

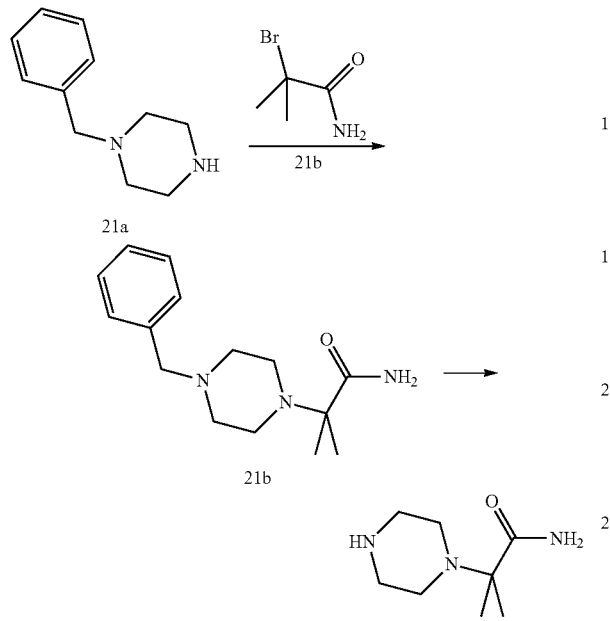

A solution of compound 21a (2.5 g, 14.2 mmol), compound 21b (4.72 g, 28.41 mmol) and cesium carbonate (9.3 g, 28.41 mmol) in acetonitrile (40 mL) was heated at 100° C. for 18 hours. Water (25 mL) was added and extracted with ethyl acetate (150 mL thrice). The combined organic extracts were dried over anhydrous sodium sulfate and concentrated under vacuum to obtain the crude product, which upon purification using by flash chromatography (3% methanol in dichloromethane as eluent) gave 3.05 g of compound 21c. To a solution of this compound (3 g) in methanol (60 mL) was added palladium carbon (1 g) and stirred under hydrogen atmosphere (balloon pressure) at room temperature for overnight. The reaction mixture was filtered and filtrate was concentrated under vacuum to obtain 2.25 g of 2-methyl-2-(piperazin-1-yl)propanamide.

[Reference Example 22] Synthesis of (9aR)-hexahydropyrazino[2,1-c][1,4]oxazin-4(3H)-one

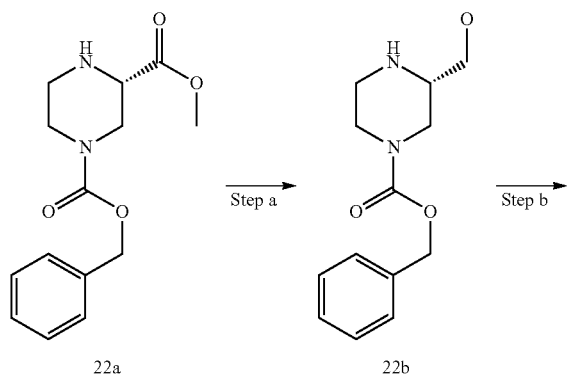

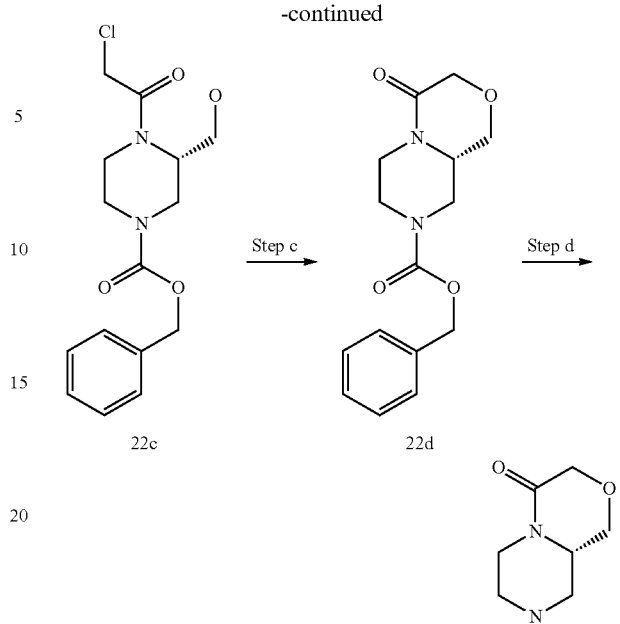

Step a: To a solution of compound 22a (10 g, 36.1 mmol) in dry tetrahydrofuran (100 mL) was added lithium borohydride (1.13 g, 54.51 mmol) portion wise at 0° C. The reaction mixture was allowed to stir at room temperature for 18 hours. Ethyl acetate (200 mL) was added drop wise followed by addition of water (50 mL), and then extracted with ethyl acetate (250 ml thrice). The combined organic extracts were dried over anhydrous sodium sulfate and concentrated under vacuum to obtain the crude product. Silica gel column chromatography (100-200 mesh) using 5% methanol in dichloromethane as eluent yielded 8.5 g of compound 22b.

Step b: To a solution of compound 22b (4.4 g, 17.6 mmol) in dichloromethane (50 mL) were added triethylamine (5.9 mL, 52.8 mmol) and chloroacetyl chloride (2 mL, 17.6 mmol) drop wise at 0° C. The reaction mixture was allowed to stir at room temperature for 90 minutes. Water (30 mL) was added and extracted with ethyl acetate (150 ml thrice). The combined organic extracts were dried over anhydrous sodium sulfate and concentrated under vacuum to obtain 4.8 g of compound 22c.

Step c: To a solution of compound 22c (4.8 g, 14.81 mmol) in dry tetrahydrofuran (45 mL) was added potassium tertiarybutoxide (2.48 g, 22.2 mmol) portion wise at 0° C. The reaction mixture was allowed to stir at room temperature for 18 hours. Water (30 mL) was added and extracted with ethyl acetate (150 mL thrice). The combined organic extracts were dried over anhydrous sodium sulfate and concentrated under vacuum to obtain crude product, which upon purification by column chromatography (100-200 mesh) using 5% methanol in dichloromethane as eluent yielded 2.5 g of compound 22d.

Step d: To a solution of compound 22d (2.5 g, 8.68 mmol) in methanol (20 mL) was added palladium carbon (500 mg) and stirred under hydrogen atmosphere (balloon pressure) at room temperature for overnight. The reaction mixture was filtered and filtrate was concentrated under vacuum to obtain 1.3 g of (9aR)-hexahydropyrazino[2,1-c][1,4]oxazin-4(3H)-one.

[Reference Example 23] Synthesis of ethyl 4-(morpholin-4-yl)piperidine-1-carboxylate

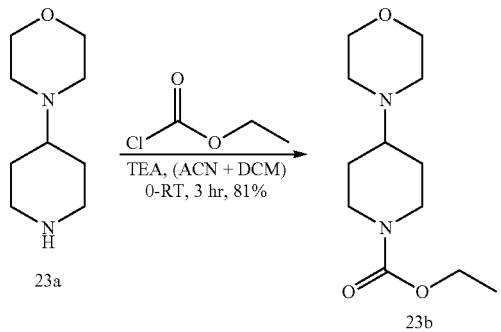

To a solution of morpholine piperidine 23a (5 g, 29.23 mmol; AK Scientific) in acetonitrile dichloromethane (100:20 mL) was added triethylamine (5.90 g, 58.47 mmol) at room temperature and cooled to 0° C. After attaining temperature, ethyl chloroformate (3.798 g, 35.076 mmol) was added and stirred for 10 minutes at same temperature followed by stirring for 2-3 hours at room temperature. The reaction mixture was filtered, water (400 mL) was added to filtrate and extracted with dichloromethane (500 mL×2). The combined organic extract was dried over anhydrous sodium sulphate, concentrated under vacuum to obtain ethyl 4-(morpholin-4-yl)piperidine-1-carboxylate (5.8 g).

$^1$H NMR (400 MHz, DMSO-d$_6$) δ ppm: 3.86-4.09 (q, 2H), 3.86-4.09 (bs, 2H), 3.50-3.62 (m, 4H), 2.76 (br. s., 2H), 2.36-2.46 (m, 4H), 2.30 (tt, J=3.54, 11.01 Hz, 1H), 1.65-1.82 (m, 2H), 1.05-1.35 (m, 2H), 1.05-1.35 (t, 3H).

[Reference Example 24] Synthesis of 4-(azetidin-3-yl)-1-methylpiperazin-2-one

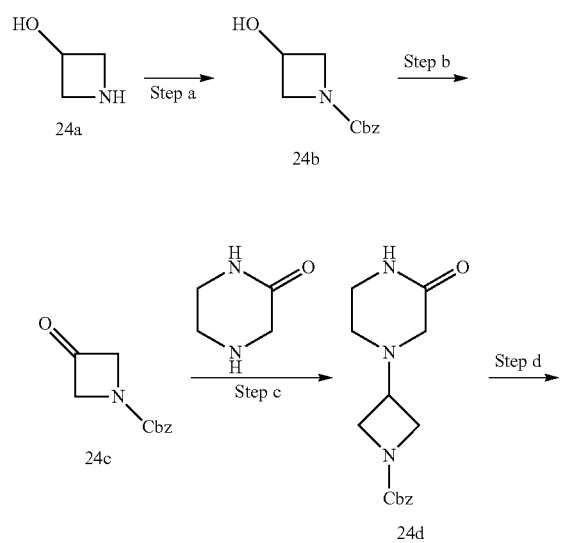

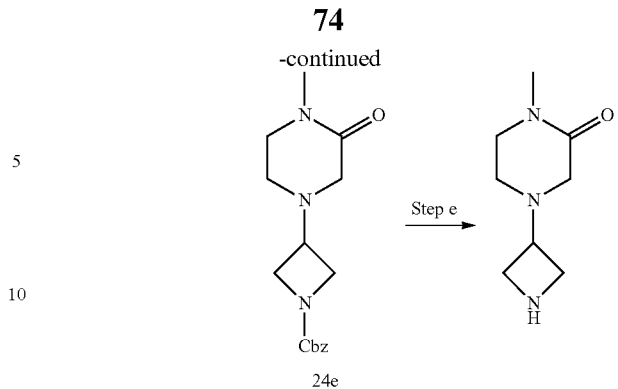

Step a: To a solution of compound 24a (12 g, 109.5 mmole; Spectrochem) in tetrahydrofuran (500 mL) was added potassium carbonate (45.417 g, 328.617 mmole) and the reaction mixture was stirred at room temperature for 1 hour. To the above reaction mixture was added benzyl chloroformate (52.35 mL, 153.35 mmole) drop wise at 0° C. and the reaction mixture was stirred at room temperature for 12 hours, then water (250 mL) was added, extracted with ethyl acetate (500×3 mL), washed with brine (250 mL), dried over anhydrous sodium sulphate, concentrated under vacuum and purified by silica gel column chromatography using 0-5% methanol in dichloromethane as eluent to obtain compound 24b (52.9%; 18 g).

Step b: To a solution of compound 24b (9 g, 43.47 mmole) in dichloromethane (500 mL) was added Dess-Martin periodinane (36.86 g, 86.95 mmole) and the reaction mixture was stirred at room temperature for 15 hours and then filtered through sintered funnel. The filtrate was washed with water (200 mL), brine (200 mL), dried over anhydrous sodium sulphate and concentrated under vacuum to obtain compound 24c (95.4%; 8.5 g).

Step c: To a solution of compound 24c (6.15 g, 30 mmole) in tetrahydrofuran (100 mL) was added piperazin-2-one (2 g, 20 mmole; Spectrochem) and glacial acetic acid (1.8 g, 30 mmole), p-toluenesulfonic acid (344 mg, 2 mmole) and the reaction mixture was stirred at room temperature for 2 hours. Sodium triacetoxyborohydride (7.42 g, 35 mmole) was added and reaction mixture was stirred at room temperature for 12 hours, The reaction mixture was neutralized with saturated solution of sodium bicarbonate, extracted with ethyl acetated (200×3 mL), washed with brine (150 mL), dried over anhydrous sodium sulphate, concentrated under vacuum and purified by column chromatography using 0-5% methanol in dichloromethane as eluent to obtain compound 24d (3.5 g).

Step d: To a solution of compound 24d (2 g, 6.9 mmole) in dimethylformamide (50 mL) was added sodium hydride (414 mg, 10.35 mmole) at 0° C. and the reaction mixture was stirred for 30 minutes, methyliodide (1.175 g, 8.28 mmole) was added, stirred for 4 hours at room temperature. Water (100 mL) was added to the reaction mixture and extracted with ethyl acetate (250×3 mL), washed with water (300 mL), brine (300 mL), dried over anhydrous sodium sulphate and concentrated under vacuum to obtain compound 24e (1.5 g).

Step e: To a solution of compound 24e (1.5 g, 4.95 mmole) in methanol (50 mL) was added palladium on carbon (400 mg) and the reaction mixture was stirred at 50 psi hydrogen in parr apparatus for 2 hours, then filtered through celite and the filtrate was concentrated under vacuum to obtain 4-(azetidin-3-yl)-1-methylpiperazin-2-one (800 mg,).

$^1$H NMR (400 MHz, DMSO-d$_6$) δ ppm: 7.91-7.97 (m, 1H), 3.30-3.38 (m, 4H), 3.21-3.27 (m, 2H), 2.84 (br. s., 3H), 2.80-2.82 (m, 5H).

In a similar fashion, 4-(azetidin-3-yl)piperazin-2-one was prepared using compound 24d.

$^1$H NMR (400 MHz, DMSO-d$_6$) δ ppm: 8.48 (s, 1H), 7.75 (br. s., 1H), 3.42 (quin, J=7.59 Hz, 4H), 3.12-3.15 (m, 3H), 2.80 (s, 2H), 2.38-2.46 (m, 2H).

Similarly 4-(azetidin-3-yl)morpholine (3.0 g) and (2R, 6S)-4-(azetidin-3-yl)-2,6-dimethylmorpholine (2.0 g) were prepared.

[Reference Example 25] Synthesis of N-methyl-1-(tetrahydro-2H-pyran-4-yl)piperidin-4-amine

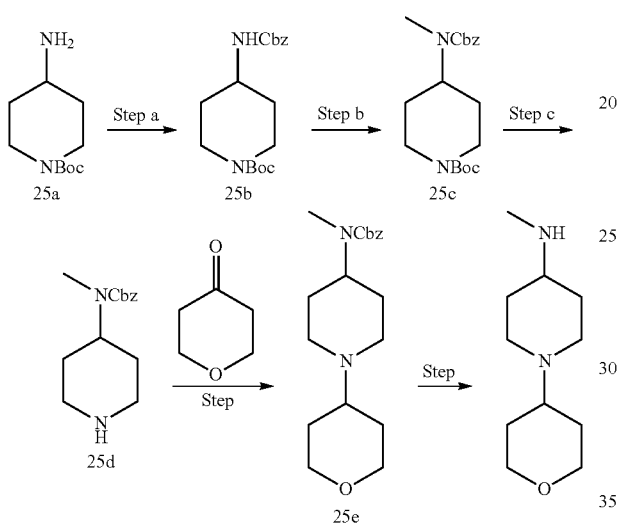

Step a: To a solution of compound 25a (10 g, 50 mmole) in dichloromethane (200 mL) was added triethylamine (10.1 g, 100 mmole) and the reaction mixture was stirred at room temperature for 1 hour. To the above reaction mixture was added benzyl chloroformate (17 mL, 60 mmole) drop wise at 0° C. and the reaction mixture was stirred at room temperature for 12 hours. It was then diluted with dichloromethane, washed with water (250 mL), brine (250 mL), dried over anhydrous sodium sulphate, concentrated under vacuum, and purified by silica gel column chromatography using 50-60% ethyl acetate in hexane as eluent to obtain compound 25b (8 g).

Step b: To a solution of compound 25b (8 g, 23.95 mmole) in tetrahydrofuran (150 mL) was added sodium hydride (1.24 g, 31.13 mmole) at 0° C. and the reaction mixture was stirred for 30 minutes. To the reaction mixture was added methyl iodide (5.099 g, 35.92 mmole) and was stirred for 12 hours at room temperature. Water (100 mL was added, extracted with ethyl acetate (250×3 mL), washed with brine (300 mL), dried over anhydrous sodium sulphate and concentrated under vacuum to obtain compound 25c (8 g).

Step c: To a solution of compound 25c (4 g, 11.49 mmole) in dichloromethane (50 mL) was added hydrochloric acid (4M) in dioxane (11 mL, 44 mmole) and the reaction mixture was stirred for 12 hours at room temperature. It was concentrated under vacuum, triturated with diethyl ether, neutralized with saturated solution of sodium bicarbonate, extracted with dichloromethane, dried over anhydrous sodium sulphate and concentrated under vacuum to obtain compound 25d (2 g).

Step d: To a solution of compound 25d (2 g, 8.6 mmole) in tetrahydrofuran (50 mL) was added compound tetrahydro-4H-pyran-4-one (1.6 g, 17.2 mmole) and glacial acetic acid (1 g, 17.2 mmole), p-toluenesulfonic acid (172 mg, 1 mmole) and the reaction mixture was stirred at room temperature for 2 hours. To it was added sodium triacetoxyborohydride (3.4 g, 17.2 mmole) and the reaction mixture was stirred at room temperature for 12 hours. Then it was neutralized with saturated solution of sodium bicarbonate, extracted with ethyl acetated (200×3 mL), washed with brine (150 mL), dried over anhydrous sodium sulphate, concentrated under vacuum and purified by column chromatography using 0-5% methanol in dichlormethane as eluent to obtain compound 25e (1.5 g).

Step e: To a solution of compound 25e (1.5 g, 4.5 mmole) in methanol (50 mL) was added palladium on carbon (400 mg) and the reaction mixture was stirred at 50 psi hydrogen in parr apparatus for 2 hours. It was then filtered through celite and the filtrate was concentrated under vacuum to obtain the title compound (800 mg).

$^1$H NMR (400 MHz, CHCl3-d) δ ppm: 4.02 (dd, J=4.52, 11.29 Hz, 2H), 3.37 (dt, J=2.01, 11.80 Hz, 2H), 2.87-2.98 (m, 2H), 2.44-2.51 (m, 1H), 2.43 (s, 3H), 2.29-2.40 (m, 1H), 2.19 (dt, J=2.26, 11.54 Hz, 2H), 1.70-1.96 (m, 4H), 1.59 (dq, J=4.52, 12.21 Hz, 2H), 1.28-1.43 (m, 2H).

In a similar fashion, N-methyl-1-(oxetan-3-yl)piperidin-4-amine was prepared using oxetan-3-one (1.23 g, 17.2 mmole) in Step d above.

$^1$H NMR (400 MHz, CHCl$_3$-d) δ ppm: 4.56-4.67 (m, 4H), 3.40-3.50 (m, 2H), 2.67-2.74 (m, 2H), 2.44 (s, 3H), 2.38-2.43 (m, 2H), 1.83-1.96 (m, 4H).

[Reference Example 26] Synthesis of 2,8-diazaspiro[4.5]decan-3-one

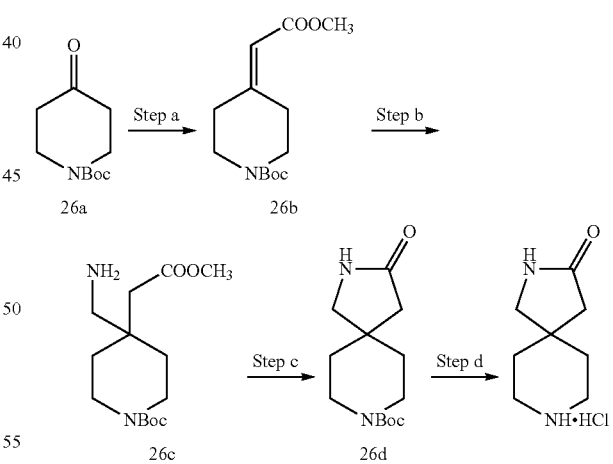

Step a: To a solution of sodium hydride (1.2 g, 30.15 mmole) in dimethylformamide (30 mL) was added trimethylphosphenoacetate drop wise at 0° C. and the reaction mixture was stirred for 30 minutes. A solution of compound 26a (5 g, 25.12 mmole) in dimethylformamide (20 mL) was added drop wise at 0° C. and the reaction mixture was stirred for 6 hours at room temperature. Then water was added and extracted with ethyl acetate (300×3 mL), washed with water (200 mL), brine (200 mL), dried over anhydrous sodium sulphate, concentrated under vacuum and purified by column chromatography using 40-50% ethyl acetate in hexane as eluent to obtain compound 26b (3 g).

Step b: To a solution of compound 26b (8 g, 31.37 mmole) in acetonitrile (100 mL) was added 1,8-diazabicyclo[5.4.0]undec-7-ene (6.2 mg, 40.78 mmole) and nitromethane (2.48 g, 40.78 mmole) and the reaction mixture was refluxed for 4 hours. Solvent was then evaporated under vacuum, the residue was diluted with ethyl acetate (800 mL) and washed with water (300×2 mL), brine (300 mL), dried over anhydrous sodium sulphate and concentrated under vacuum to obtain compound 26c (4.5 g).

Step c: To a solution of compound 26c (4.5 g, 14.15 mmole) in methanol (50 mL) was added palladium on carbon (1 g) and the reaction mixture was stirred at 50 psi hydrogen at parr apparatus for 2 hours. It was then filtered through celite and the filtrate was concentrated under vacuum to obtain compound 26d (3.5 g).

Step d: To a solution of compound 26d (3.5 g, 13.8 mmole) in dichloromethane (50 mL) was added hydrochloric acid (4M) in dioxane (14 mL, 56 mmole) and the reaction mixture was stirred for 12 hours at room temperature. It was concentrated under vacuum and triturated with diethyl ether to obtain 2,8-diazaspiro[4.5]decan-3-one (2 g).

$^1$H NMR (400 MHz, DMSO-$d_6$) δ ppm: 3.08-3.19 (m, 2H), 2.97-3.01 (m, 2H), 2.56-2.65 (m, 2H), 1.97-2.02 (m, 2H), 1.38-1.45 (m, 4H).

[Reference Example 27] Synthesis of (2R,6S)-2,6-dimethyl-4-(piperidin-4-yl)morpholine

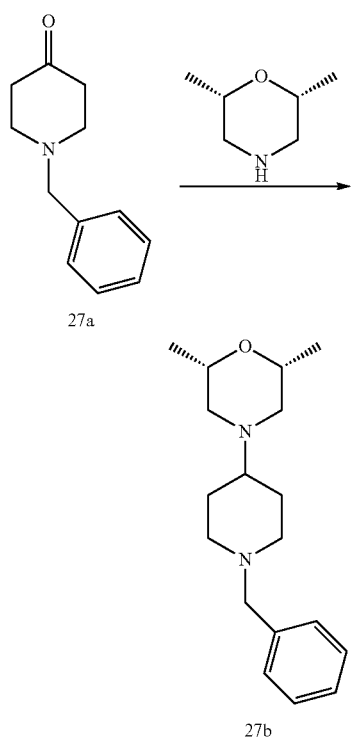

Step a: To a solution of compound 27a (6 g, 33.89 mmol) in tetrahydrofuran (90 mL), were added cis-2,6 dimethyl morpholine (4.596 g, 40.67 mmole) and p-toluenesulfonic acid (645 mg, 3.38 mmol) followed by acetic acid (5 mL, 67.79 mmole). After 5 minutes, sodium triacetoxy borohydride (14.305 g, 67.79 mmole) was added portion wise at 0° C. and reaction was allowed to stir at room temperature for overnight. Saturated solution of sodium bicarbonate was added and extracted using dichloromethane. The organic extract was dried over anhydrous sodium sulphate and concentrated under vacuum to obtain the crude product, which upon purification by flash chromatography (silica gel) using 0-5% methanol in dichloromethane to obtain compound 27b (7 g).

Step b: To a solution of compound 27b (7 g) in methanol (100 mL), was added palladium carbon (2 g) and stirred under hydrogen atmosphere (balloon pressure) at room temperature for overnight. The reaction mixture was filtered and filtrate was concentrated under vacuum to obtain (2R, 6S)-2,6-dimethyl-4-(piperidin-4-yl)morpholine (4.1 g).

In a similar fashion, 4-(piperidin-3-yl)morpholine (3.0 g) was prepared using 1-benzylpiperidin-3-one (5 g, 26.45 mmol) and morpholine (4.6 mL, 52.9 mmol).

$^1$H NMR (400 MHz, DMSO-$d_6$) δ ppm: 3.48-3.58 (m, 4H), 3.05 (d, J=11.54 Hz, 1H), 2.71-2.95 (m, 2H), 2.36-2.48 (m, 6H), 2.14-2.25 (m, 1H), 1.84 (d, J=2.01 Hz, 1H), 1.59-1.69 (m, 1H), 1.24-1.37 (m, 2H).

[Reference Example 28] Synthesis of 4-(piperidin-4-yl)morpholin-3-one

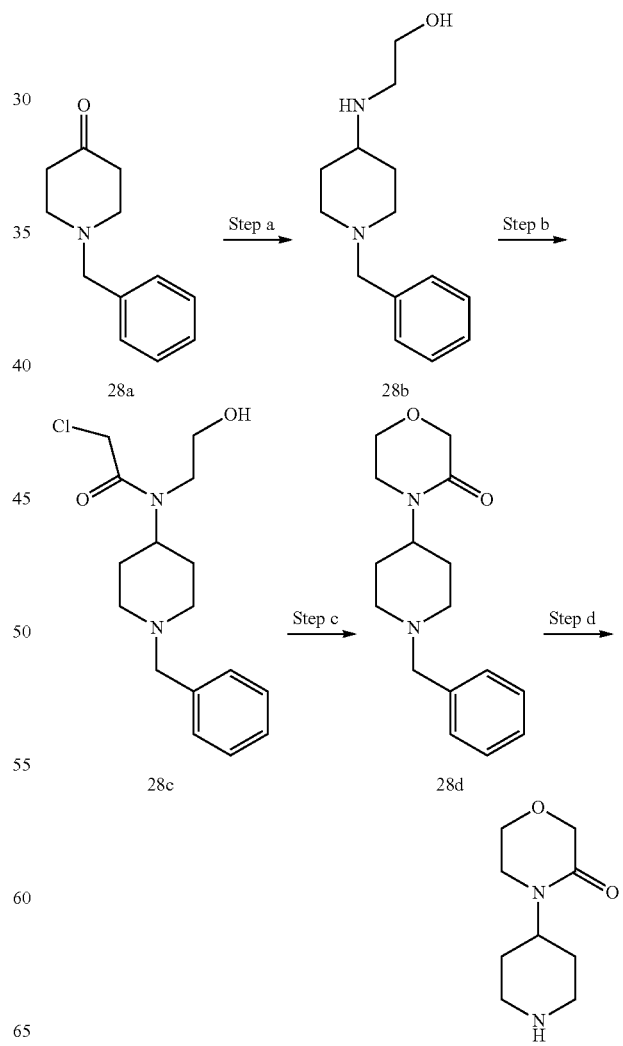

Step a: To a solution of compound 28a (3 g, 15.85 mmol) in 1,2-dichloroethane (60 mL), was added 2-amino ethanol (0.96 g, 15.85 mmol) and acetic acid (1.14 g, 19.2 mmol) at room temperature. After 5 minutes sodium triacetoxy borohydride (10.05 g, 66.12 mmol) was added portion wise and reaction was allowed to stir at room temperature for 18 hours. Saturated solution of sodium bicarbonate was added and extracted with ethyl acetate. The organic extract was dried over anhydrous sodium sulphate and concentrated under vacuum to obtain compound 28b (3.5 g).

Step b: To a solution of compound 28b (1 g, 4.27 mmol) in 1,2-dichloroethane (20 mL), was added triethyl amine (1.19 mL, 8.54 mmol) and chloroacetyl chloride (0.52 mL, 6.41 mmol) drop wise at 0° C. and was allowed to stir at room temperature for 2 hours. Saturated solution of sodium bicarbonate was added and extracted with dichloromethane. The organic extract was dried over anhydrous sodium sulphate and concentrated under vacuum to obtain compound 28c (1.3 g)

Step c: To a solution of compound 28c (1.4 g, 4.5 mmol) in dimethylformamide (10 mL), was added sodium hydride (110 mg, 4.95 mmol) portion wise at −10° C. and stirred for 60 minutes, warmed and stirred for 2 hours at room temperature. The reaction mixture was heated at 80° C. for 15 hours and then for 48 hours at room temperature. The reaction was cooled to room temperature and water was added and extracted with dichlormethane. The combined organic extract was dried over anhydrous sodium sulphate and concentrated under vacuum to obtain the crude product, which upon purification using silica gel (100-200 mesh size) column chromatography and 0-5% methanol and dichloromethane system as eluent gave compound 28d (450 mg).

Step d: To a solution of compound 28d (2.5 g) in methanol (30 mL), was added palladium carbon (500 mg) and stirred under hydrogen atmosphere (balloon pressure) at room temperature for overnight. The reaction mixture was filtered and filtrate was concentrated under vacuum to obtain 4-(piperidin-4-yl)morpholin-3-one (1.5 g).

[Reference Example 29] Synthesis of piperazin-1-yl(pyrimidin-2-yl)methanone

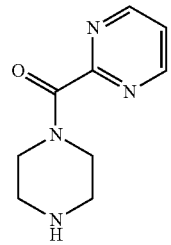

Step a: To a solution of compound 29a (500 mg, 2.688 mmol; Spectrochem) in dichloromethane (15 mL), was added pyrimidine-2 carboxylic acid (430 mg, 3.495 mmol), (1-[bis(dimethylamino)methylene]-1H-1,2,3-triazolo[4,5-b]pyridinium 3-oxid hexafluorophosphate) (1.276 g, 3.36 mmole), N,N-diisopropylethylamine (1.55 mL, 9.406 mol) and stirred the reaction mixture at room temperature for overnight. The reaction mixture was diluted with dichloromethane, washed with 10% hydrochloric acid solution, followed by sodium bicarbonate and finally with water. The organic layer was dried over anhydrous sodium sulphate and concentrated under vacuum to obtain the crude mixture, which was triturate in hexane to obtain pure compound 29b (450 mg).

Step b: To a solution of compound 29b (450 mg) in dichlormethane (5 mL) was added trifluoro acetic acid (2 mL) at room temperature and stirred for overnight. The volatiles were removed under vacuum and dichloromethane was added, washed with sodium bicarbonate solution. The organic layer was dried over anhydrous sodium sulphate and concentrated under vacuum to obtain piperazin-1-yl(pyrimidin-2-yl)methanone (250 mg)

In a similar fashion, 1-(piperazin-1-yl)-2-(pyrimidin-2-yl)ethanone (400 mg) was prepared using pyrimidine-2 acetic acid (573 mg, 3.49 mmol), (1-[bis(dimethylamino)methylene]-1H-1,2,3-triazolo[4,5-b]pyridinium 3-oxid hexafluorophosphate) (1.276 g, 3.36 mmole) and N,N-diisopropylethylamine (1.55 mL, 9.46 mmol).

[Reference Example 30] Synthesis of N-(pyrrolidin-3-yl)acetamide

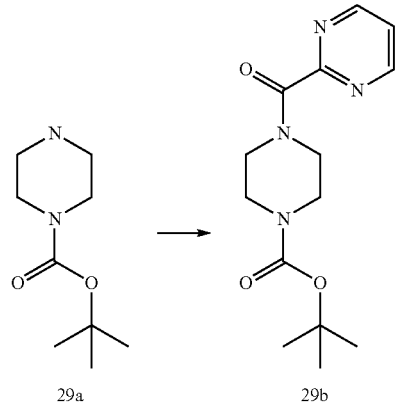

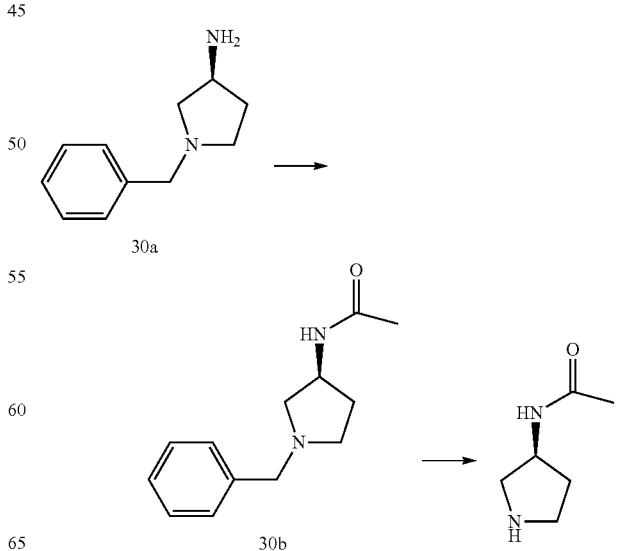

Step a: To a solution of compound 30a (500 mg, 2.83 mmol; Aldrich) in dichloromethane (15 mL) was added acetic anhydride (0.3 mL, 1.12 mmol) at 0° C. and allowed to stir at room temperature for 2 hours. The volatiles were removed under vacuum and water was added followed by saturated sodium bicarbonate and then extracted with dichloromethane. The combined organic extract was washed with brine, dried over anhydrous sodium sulphate, concentrated under vacuum and purified by column chromatography using 0-5% methanol in dichloromethane to obtain compound 30b (238 mg).

Step b: To a solution of compound 30b (238 mg) in methanol (15 mL) was added palladium carbon (250 mg) and stirred under hydrogen atmosphere (balloon pressure) at room temperature for overnight. The reaction mixture was filtered and filtrate was concentrated under vacuum to obtain N-(pyrrolidin-3-yl)acetamide (150 mg).

[Reference Example 31] Synthesis of N-(pyrrolidin-3-yl)methanesulfonamide

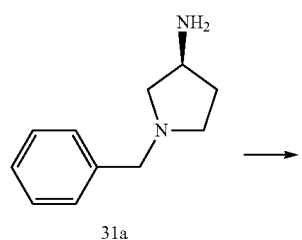

31a

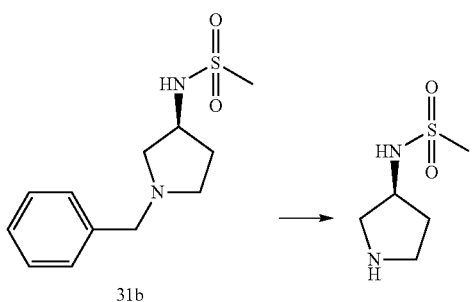

31b

Step a: To a solution of compound 31a (500 mg, 2.83 mmol) in dichloromethane (40 mL) was added triethyl amine (0.58 mL, 4.25 mmol) at 0° C. followed by methane sulfonyl chloride (0.43 mL, 3.4 mmol) and allowed to stir at room temperature for overnight. The volatiles were removed under vacuum; water was added and extracted with dichloromethane. The organic extract was washed with brine, dried over anhydrous sodium sulphate and concentrated under vacuum to obtain compound 31b (750 mg).

Step b: To a solution of compound 31b (750 mg) in methanol (15 mL) was added palladium carbon (250 mg) and stirred under hydrogen atmosphere (balloon pressure) at room temperature for overnight. The reaction mixture was filtered and filtrate was concentrated under vacuum to obtain N-(pyrrolidin-3-yl)methanesulfonamide (450 mg).

TABLE 1

| Compd. No. | $^1$H NMR (400 MHz, DMSO-d6) δppm | Mass Spectrum (ESI): m/z [M + H] | Compound (1b) (mg) (Source) | Scheme No. | Compound (1a or 2a) (mg) |
|---|---|---|---|---|---|
| 2** | 8.10 (s, 1H), 7.97 (s, 1H), 7.51 (br. s., 1H), 4.21 (br. s., 4H), 3.93-4.01 (m, 3H), 3.75-3.87 (m, 8H), 3.53-3.68 (m, 2H), 2.78 (t, J = 5.43 Hz, 2H), 2.70 (br. s., 4H) | 442.20 | 328 (Aldrich) | 2 | 300 |
| 5 | 13.40-13.60 (m, 1H), 8.24 (s, 1H), 7.93 (s, 1H), 4.85-5.01 (m, 1H), 4.43-4.55 (m, 1H), 4.09-4.39 (m, 4H), 3.88 (s, 3H), 3.75 (t, J = 4.64 Hz, 4H), 3.46-3.56 (m, 2H), 3.17-3.25 (m, 1H), 2.82-2.91 (m, 1H), 2.74 (d, J = 10.79 Hz, 2H), 2.43-2.48 (m, 1H), 1.81 (br. s., 4H), 1.31-1.51 (m, 2H), 1.04 (d, J = 6.27 Hz, 6H) | 510.11 | 208 (Synthesized) | 1 | 150 |
| 6 | 13.30-13.82 (m, 1H), 8.25 (s, 1H), 7.94 (s, 1H), 5.10-5.30 (m, 1H), 4.41-4.58 (m, 2H), 4.13-4.37 (m, 4H), 4.08 (s, 2H), 3.89 (s, 4H), 3.77 (d, J = 4.52 Hz, 4H), 3.53-3.69 (m, 2H), 3.11-3.29 (m, 1H), 2.72-2.98 (m, 2H) | 468 | 109 (Synthesized) | 1 | 100 |

TABLE 1-continued

| Compd. No. | ¹H NMR (400 MHz, DMSO-d6) δppm | Mass Spectrum (ESI): m/z [M + H] | Compound (1b) (mg) (Source) | Scheme No. | Compound (1a or 2a) (mg) |
|---|---|---|---|---|---|
| 7 | 13.52 (s, 1H), 8.24 (s, 1H), 7.94 (s, 1H), 5.15 (d, J = 13.30 Hz, 1H), 4.50-4.71 (m, 2H), 4.24 (br. s., 4H), 4.04 (s, 2H), 3.89 (s, 3H), 3.69-3.82 (m, 6H), 3.19-3.29 (m, 3H), 2.82-2.98 (m, 1H), 1.52-1.89 (m, 4H) | 496.04 | 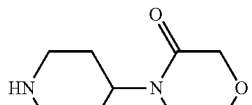<br>155<br>(Synthesized) | 1 | 150 |
| 8 | 13.22-13.64 (m, 1H), 8.14 (br. s., 1H), 7.29 (br. s., 1H), 7.03 (br. s., 1H), 4.18 (br. s., 6H), 3.78 (d, J = 17.32 Hz, 9H), 3.29-3.32 (m, 3H), 2.44-2.49 (m, 4H), 1.09 (br. s., 6H) | 497.02 | 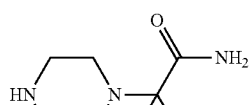<br>188<br>(Synthesized) | 2 | 200 |
| 9 | 13.27-13.57 (m, 1H), 8.14 (s, 1H), 4.03-4.39 (m, 6H), 3.85-3.94 (m, 2H), 3.71-3.82 (m, 7H), 3.62-3.70 (m, 2H), 3.21-3.31 (m, 4H), 2.52-2.60 (m, 4H), 1.65-1.76 (m, 2H), 1.34-1.48 (m, 2H) | 496.02 | 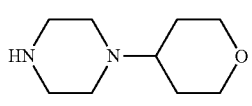<br>187<br>(Synthesized) | 2 | 200 |
| 10 | 13.10-13.78 (m, 1H), 8.15-8.35 (m, 1H), 7.83-8.03 (m, 1H), 7.22-7.43 (m, 1H), 6.94-7.14 (m, 1H), 4.05-4.42 (m, 6H), 3.88 (s, 3H), 3.68-3.81 (m, 6H), 2.35-2.49 (m, 4H), 1.09 (s, 6H) | 482.58 | 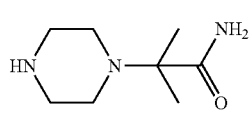<br>144<br>(Synthesized) | 1 | 150 |
| 11 | 13.37-13.67 (m, 1H), 8.24 (s, 1H), 7.93 (s, 1H), 4.05-4.38 (m, 6H), 3.88 (s, 5H), 3.73-3.78 (m, 4H), 3.63-3.69 (m, 2H), 3.27 (s, 2H), 2.56 (d, J = 3.51 Hz, 4H), 2.38-2.46 (m, 1H), 1.65-1.77 (m, 2H), 1.33-1.49 (m, 2H) | 482.02 | 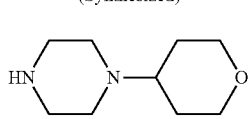<br>143<br>(Synthesized) | 1 | 150 |
| 12 | 13.17-13.69 (m, 1H), 8.15 (s, 1H), 4.87-5.09 (m, 1H), 4.51-4.70 (m, 1H), 4.20 (s, 4H), 3.70-3.84 (m, 7H), 3.01-3.13 (m, 1H), 2.65-2.78 (m, 1H), 2.50 (br. s., 4H), 1.72-1.88 (m, 2H), 1.46-1.56 (m, 1H), 1.13-1.30 (m, 2H), 1.05 (s, 6H) | 469.06 | 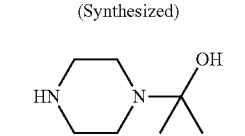<br>189<br>(Synthesized) | 2 | 200 |
| 13 | 13.37-13.62 (m, 1H), 8.24 (s, 1H), 7.93 (s, 1H), 5.02-5.17 (m, 1H), 4.44-4.79 (m, 1H), 4.14-4.39 (m, 4H), 3.89 (s, 3H), 3.75 (t, J = 4.64 Hz, 4H), 3.58 (br. s., 2H), 3.47-3.53 (m, 2H), 3.20-3.31 (m, 2H), 2.84-2.96 (m, 1H), 2.53-2.60 (m, 1H), 2.42-2.47 (m, 2H), 2.28-2.39 (m, 1H), 1.88-1.98 (m, 1H), 1.73-1.84 (m, 1H), 1.38-1.62 (m, 2H) | 482.12 | 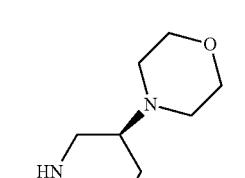<br>143<br>(Synthesized) | 1 | 150 |
| 14 | 13.47 (br. s., 1H), 8.24 (s, 1H), 7.93 (s, 1H), 4.96-5.07 (m, 1H), 4.52-4.65 (m, 1H), 4.11-4.42 (m, 5H), 3.88 (s, 3H), 3.75 (t, J = 4.29 Hz, 4H), 3.07 (br. s., 1H), 2.72 (br. s., 1H), 1.72-1.89 (m, 2H), 1.51 (br. s., 1H), 1.22 (d, J = 14.40 Hz, 2H), 1.05 (s, 6H) | 455.16 | 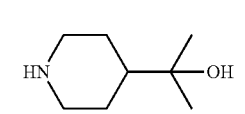<br>120<br>(Synthesized) | 1 | 150 |

TABLE 1-continued

| Compd. No. | ¹H NMR (400 MHz, DMSO-d6) δppm | Mass Spectrum (ESI): m/z [M + H] | Compound (1b) (mg) (Source) | Scheme No. | Compound (1a or 2a) (mg) |
|---|---|---|---|---|---|
| 25 | 13.34-13.86 (m, 1H), 8.93 (br. s., 2H), 8.22-8.36 (m, 1H), 7.86-8.01 (m, 1H), 7.57-7.72 (m, 1H), 3.97-4.61 (m, 6H), 3.89 (br. s., 3H), 3.80 (br. s., 6H), 3.70 (br. s., 4H) | 504.11 | 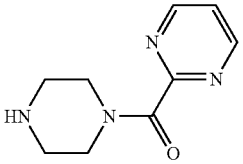<br>173<br>(Synthesized) | 1 | 100 |
| 26 | 13.19-13.69 (m, 1H), 8.24 (s, 1H), 7.93 (s, 1H), 7.84-7.91 (m, 1H), 4.70-4.87 (m, 1H), 4.04-4.47 (m, 5H), 3.89 (s, 3H), 3.76 (d, J = 4.02 Hz, 5H), 3.39-3.48 (m, 1H), 3.00-3.13 (m, 1H), 1.78-1.88 (m, 5H), 1.29-1.51 (m, 2H) | 454.18 | 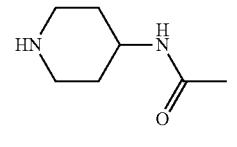<br>80<br>(Acros) | 1 | 100 |
| 27 | 13.37-13.76 (m, 1H), 8.40 (d, J = 4.77 Hz, 2H), 8.25 (s, 1H), 7.94 (s, 1H), 6.68 (t, J = 4.77 Hz, 1H), 4.29 (br. s., 6H), 3.82-3.94 (m, 7H), 3.70-3.81 (m, 6H) | 476.18 | 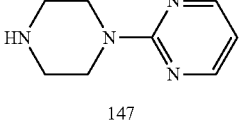<br>147<br>(Alfa aiser) | 1 | 80 |
| 28 | 13.20-13.64 (m, 1H), 8.24 (s, 1H), 7.93 (s, 1H), 7.05-7.38 (m, 1H), 4.70-4.99 (m, 1H), 4.06-4.43 (m, 5H), 3.88 (s, 3H), 3.75 (t, J = 4.64 Hz, 4H), 3.37-3.58 (m, 2H), 3.01-3.11 (m, 1H), 2.95 (s, 3H), 1.84-2.02 (m, 2H), 1.35-1.61 (m, 2H) | 490.15 | 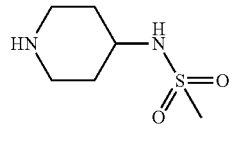<br>99<br>(Synthesized) | 1 | 100 |
| 29 | 13.00-13.77 (m, 1H), 8.54-8.60 (m, 2H), 8.48-8.54 (m, 1H), 8.23-8.28 (m, 1H), 7.79-8.02 (m, 1H), 4.11-4.45 (m, 6H), 4.02-4.06 (m, 2H), 3.89 (s, 3H), 3.64-3.81 (m, 8H), 3.56-3.63 (m, 2H) | 518.19 | 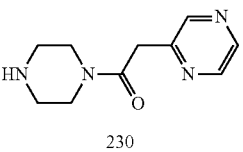<br>230<br>(Synthesized) | 1 | 100 |
| 31 | 12.92-14.36 (m, 1H), 8.22-8.30 (m, 1H), 8.08-8.21 (m, 1H), 7.81-8.02 (m, 1H), 4.71-4.83 (m, 1H), 4.10-4.45 (m, 8H), 3.89 (s, 3H), 3.80-3.86 (m, 1H), 3.76 (br. s., 4H) | 412.18 | 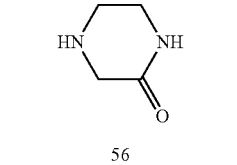<br>56<br>(Spectrochem) | 1 | 100 |
| 32 | 13.37-13.73 (m, 1H), 8.25 (s, 1H), 7.94 (s, 1H), 7.24 (s, 2H), 7.00 (s, 2H), 6.78-6.87 (m, 1H), 4.04-4.61 (m, 6H), 3.89 (s, 3H), 3.80-3.86 (m, 2H), 3.77 (d, J = 3.76 Hz, 4H), 3.25 (d, J = 4.02 Hz, 4H) | 474.22 | 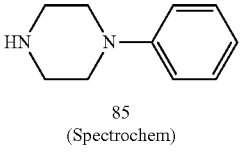 [SMILES: c1ccc(N2CCNCC2)cc1]<br>85<br>(Spectrochem) | 1 | 100 |
| 33 | 13.27-13.82 (m, 1H), 8.28-8.40 (m, 1H), 8.23 (s, 1H), 7.92 (s, 1H), 4.06-4.52 (m, 4H), 3.88 (s, 3H), 3.77 (t, J = 4.64 Hz, 5H), 1.68-1.87 (m, 4H), 1.58-1.66 (m, 1H), 1.38-1.53 (m, 2H), 1.25-1.38 (m, 2H), 1.06-1.22 (m, 1H) | 411.24 | 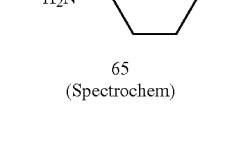<br>65<br>(Spectrochem) | 1 | 100 |

TABLE 1-continued

| Compd. No. | ¹H NMR (400 MHz, DMSO-d6) δppm | Mass Spectrum (ESI): m/z [M + H] | Compound (1b) (mg) (Source) | Scheme No. | Compound (1a or 2a) (mg) |
|---|---|---|---|---|---|
| 34 | 13.24-13.82 (m, 1H), 8.14-8.33 (m, 1H), 7.74-8.04 (m, 1H), 4.12-4.59 (m, 6H), 3.89 (s, 3H), 3.76 (br. s., 6H), 3.19-3.29 (m, 4H), 2.92 (s, 3H) | 476.22 | 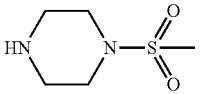<br>183<br>(Synthesized) | 1 | 100 |
| 35 | 13.50-13.52 (m, 1H), 8.20-8.30 (m, 1H), 7.90-7.98 (m, 1H), 7.21-7.34 (m, 5H), 5.04-5.15 (m, 1H), 4.62-4.71 (m, 1H), 4.09-4.44 (m, 4H), 3.87-3.90 (s, 3H), 3.61-3.82 (m, 4H), 2.87-2.97 (m, 3H), 1.84-1.99 (m, 2H), 1.58-1.74 (m, 2H) | 473.51 | 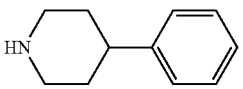<br>90<br>(Spectrochem) | 1 | 100 |
| 36 | 13.39-13.76 (m, 1H), 8.51-8.78 (m, 1H), 8.23 (s, 1H), 7.93 (s, 1H), 4.14-4.45 (m, 4H), 3.88 (s, 3H), 3.77 (t, J = 4.64 Hz, 4H), 3.09-3.21 (m, 3H), 1.67 (br. s., 6H), 1.10-1.27 (m, 4H) | 425.53 | 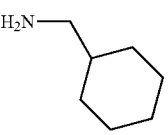<br>63<br>(Alfa aiser) | 1 | 100 |
| 37** | 7.98-8.05 (m, 1H), 7.87-7.96 (m, 1H), 5.70-5.94 (m, 1H), 4.48-4.62 (m, 1H), 4.19-4.36 (m, 4H), 4.13-4.18 (m, 1H), 3.88 (s, 3H), 3.80 (br. s., 5H), 3.70-3.77 (m, 1H), 3.69-3.76 (m, 1H), 3.56-3.66 (m, 1H), 2.05-2.29 (m, 2H), 1.94 (d, J = 5.02 Hz, 3H) | 440.50 | 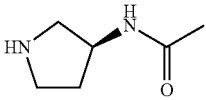<br>72<br>(Synthesized) | 1 | 100 |
| 38 | 13.12-13.84 (m, 1H), 8.14-8.34 (m, 1H), 7.84-8.02 (m, 1H), 7.32-7.57 (m, 1H), 4.14-4.41 (m, 4H), 4.04-4.18 (m, 1H), 3.95-4.04 (m, 2H), 3.89 (s, 3H), 3.73-3.80 (m, 4H), 3.64-3.71 (m, 1H), 3.48-3.58 (m, 1H), 2.98 (d, J = 7.78 Hz, 3H), 2.07-2.27 (m, 1H), 1.78-2.00 (m, 1H) | 476.48 | 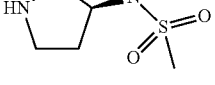<br>92<br>(Synthesized) | 1 | 100 |
| 43 | 13.46-13.67 (m, 1H), 8.24 (s, 1H), 7.93 (s, 1H), 4.09-4.39 (m, 6H), 3.89 (s, 3H), 3.76 (d, J = 4.27 Hz, 4H), 3.62-3.69 (m, 2H), 3.44 (br. s., 4H), 1.43 (s, 9H). | 498.30 | 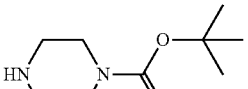<br>52<br>(Spectrochem) | 1 | 100 |
| 44 | 13.44-13.62 (m, 1H), 8.24 (s, 1H), 7.93 (s, 1H), 4.22-4.41 (m, 4H), 3.88 (s, 4H), 3.75 (br. s., 6H), 2.66-2.78 (m, 1H), 2.20 (d, J = 9.54 Hz, 8H), 1.62-1.89 (m, 1H) | 426.20 | 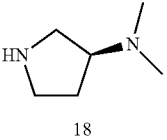<br>18<br>(Aldrich) | 1 | 50 |
| 45 | 13.53 (br. s., 1H), 8.24 (s, 1H), 7.93 (s, 1H), 4.05-4.32 (m, 8H), 3.89 (s, 3H), 3.75 (br. s., 4H), 3.68 (br. s., 2H), 3.30 (br. s., 2H), 2.61 (br.s., 4H), 1.12-1.23 (m, 3H) | 484.16 | 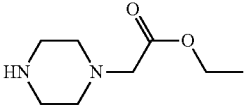<br>36<br>(Aldrich) | 1 | 80 |

TABLE 1-continued

| Compd. No. | ¹H NMR (400 MHz, DMSO-d6) δppm | Mass Spectrum (ESI): m/z [M + H] | Compound (1b) (mg) (Source) | Scheme No. | Compound (1a or 2a) (mg) |
|---|---|---|---|---|---|
| 46 | 13.47-13.59 (m, 1H), 8.24 (s, 1H), 7.93 (s, 1H), 4.10-4.33 (m, 6H), 3.88 (s, 3H), 3.72-3.78 (m, 4H), 3.64-3.70 (m, 2H), 2.38 (br. s., 4H), 2.21 (s, 3H) | 412.18 | 28 (Spectrochem) | 1 | 50 |
| 51# | 13.44-13.52 (m, 1H), 8.22-8.26 (m, 1H), 7.91-7.96 (m, 1H), 4.87-4.98 (m, 1H), 4.42-4.51 (m, 1H), 4.15-4.36 (m, 4H), 4.01-4.10 (m, 2H), 3.88 (s, 3H), 3.71-3.78 (m, 4H), 3.18-3.26 (m, 1H), 2.83-2.92 (m, 1H), 2.26-2.32 (m, 2H), 1.98-2.08 (m, 1H), 1.69-1.84 (m, 2H), 1.15-1.25 (m, 5H) | 483.19 | 287 (Aldrich) | 1 | 300 |
| 53 | 13.41-13.56 (m, 1H), 8.24 (s, 1H), 7.93 (s, 1H), 4.14-4.36 (m, 4H), 3.98-4.05 (m, 2H), 3.88 (s, 3H), 3.75 (t, J = 4.52 Hz, 4H), 3.59-3.67 (m, 2H), 1.57 (br. s., 6H) | 397.24 | 16 (Spectrochem) | 1 | 60 |
| 61 | 8.13 (s, 1H), 8.04 (s, 1H), 7.93 (t, J = 5.31 Hz, 1H), 4.27-4.47 (m, 3H), 4.15 (s, 3H), 3.96 (s, 3H), 3.84-3.91 (m, 4H), 3.67-3.76 (m, 4H), 3.55 (q, J = 6.15 Hz, 2H), 2.63 (t, J = 6.19 Hz, 2H), 2.47-2.57 (m, 4H) | 484.3 | 268 (Aldrich) | 1 | 255 |
| 63** | 8.33 (t, J = 5.52 Hz, 1H), 8.13 (s, 1H), 7.96 (s, 1H), 4.37 (br. s., 4H), 3.84-3.97 (m, 7H), 3.76 (t, J = 4.64 Hz, 4H), 3.64 (q, J = 5.77 Hz, 2H), 2.44-2.60 (m, 6H), 1.77-1.87 (m, 2H) | 456.20 | 489 489 | 2 | 500 |
| 64* | 8.17 (s, 1H), 8.05 (s, 1H), 4.37 (br. s., 4H), 3.93 (s, 3H), 3.76-3.88 (m, 4H), 3.48 (dt, J = 2.76, 7.15 Hz, 2H), 3.19-3.28 (m, 1H), 2.55 (s, 5H), 2.07-2.32 (m, 2H), 1.82-1.95 (m, 2H), 1.61-1.74 (m, 2H) | 440.20 | 261 (Aldrich) | 2 | 300 |
| 67** | 8.13 (s, 1H), 8.04 (s, 1H), 7.95 (t, J = 5.81 Hz, 1H), 4.36 (br. s., 4H), 4.16 (s, 3H), 3.96 (s, 3H), 3.83-3.91 (m, 4H), 3.72 (t, J = 4.55 Hz, 4H), 3.56 (q, J = 6.32 Hz, 2H), 2.40-2.54 (m, 6H), 1.83 (quin, J = 6.51 Hz, 2H) | 470.3 | 209 (TCI) | 1 | 180 |
| 68** | 8.16 (t, J = 6.40 Hz, 1H), 8.07 (s, 1H), 7.86 (s, 1H), 4.32 (br. s., 4H), 3.76-3.86 (m, 7H), 3.30-3.47 (m, 6H), 2.30-2.39 (m, 2H), 1.96 (quin, J = 7.53 Hz, 2H), 1.80 (quin, J = 6.34 Hz, 2H) | 454.20 | 290 (Acros) | 2 | 300 |

TABLE 1-continued

| Compd. No. | ¹H NMR (400 MHz, DMSO-d6) δppm | Mass Spectrum (ESI): m/z [M + H] | Compound (1b) (mg) (Source) | Scheme No. | Compound (1a or 2a) (mg) |
|---|---|---|---|---|---|
| 70** | 8.10 (s, 1H), 8.05 (s, 1H), 4.36 (br. s., 4H), 3.96 (s, 3H), 3.82-3.92 (m, 2H), 3.58 (t, J = 6.06 Hz, 2H), 3.39 (td, J = 1.55, 3.22 Hz, 1H), 3.03 (br. s., 7H), 2.71 (t, J = 5.81 Hz, 3H), 2.43 (br. s., 3H), 1.97-2.09 (m, 1H) | 455.20 | 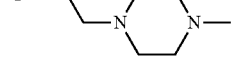<br>121<br>(Spectrochem) | 2 | 200 |
| 71 | 13.32-13.85 (m, 1H), 8.88 (br. s., 1H), 8.15 (s, 1H), 5.02 (br. s., 1H), 4.43 (d, J = 6.02 Hz, 2H), 4.17-4.36 (m, 6H), 3.82 (s, 3H), 3.76 (m, 4H) 3.54-3.67 (m, 4H), 2.45-2.55 (s, 3H) | 443.18 | 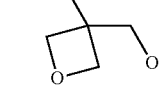<br>39.5<br>(Aldrich) | 1 | 100 |
| 73** | 8.30 (t, J = 6.44 Hz, 1H), 8.13 (s, 1H), 8.04 (s, 1H), 4.27-4.52 (m, 4H), 4.15 (s, 3H), 3.96 (s, 3H), 3.83-3.90 (m, 4H), 3.36-3.48 (m, 6H), 2.41 (t, J = 8.21 Hz, 2H), 2.05 (quin. J = 7.58 Hz, 2H), 1.78-1.87 (m, 2H) | 468.2 | 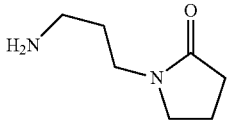<br>199<br>(Acros) | 1 | 180 |
| 76 | 13.47-13.75 (m, 1H), 8.49-8.74 (m, 1H), 8.24 (s, 1H), 7.93 (s, 1H), 4.68-4.89 (m, 1H), 4.15-4.47 (m, 4H), 3.88 (s, 3H), 3.69-3.82 (m, 4H), 3.20 (dd, J = 3.64, 5.90 Hz, 4H), 0.85 (s, 6H) | 415.27 | H₂NCH₂C(CH₃)₂CH₂OH<br><br>373<br>(Acros) | 2 | 800 |
| 77 | 13.25 (br. s., 1H), 8.23 (s, 1H), 8.10-8.30 (m, 1H), 6.84 (s, 1H), 6.73-6.96 (m, 1H), 5.13-5.27 (m, 1H), 4.61 (br. s., 2H), 4.02-4.08 (m, 2H), 3.84-3.96 (m, 7H), 3.76-3.82 (m, 6H), 3.26 (t, J = 4.64 Hz, 2H), 2.85-2.96 (m, 1H), 1.60-1.78 (m, 4H) | 495.26 | 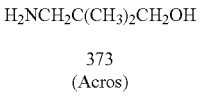<br>80<br>(Synthesized) | 1 | 103.37 |
| 78 | 13.12-13.37 (m, 1H), 8.14-8.31 (m, 1H), 7.95-8.01 (m, 1H), 6.81-6.86 (m, 1H), 4.36 (s, 4H), 4.00-4.08 (m, 2H), 3.88 (s, 8H), 3.76-3.83 (s, 3H), 3.84 (m, 1H), 3.56-3.62 (m, 2H), 1.80-1.91 (m, 4H) | 438.25 | 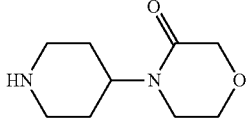<br>80<br>(Synthesized) | 1 | 71.34 |
| 79 | 1H NMR (400 MHz, DMSO-d6) d 13.25-13.45 (m, 1H), 8.18 (s, 1H), 7.92 (d, J = 1.25 Hz, 1H), 4.37 (s, 4H), 4.01-4.12 (m, 2H), 3.91 (s, 3H), 3.75-3.85 (m, 8H), 3.53-3.64 (m, 2H), 1.82-1.93 (m, 4H) | 456.28 | <br>95<br>(Synthesized) | 1 | 90 |
| 81 | 13.33-13.49 (m, 1H), 8.14-8.24 (m, 1H), 7.88-7.99 (m, 1H), 7.25-7.37 (m, 1H), 6.96-7.09 (m, 1H), 4.16-4.29 (m, 2H), 3.91 (s, 3H), 3.80 (d, J = 5.52 Hz, 10H), 2.36-2.48 (m, 4H), 1.09 (s, 6H) | 499.06 | <br>194<br>(Synthesized) | 2 | 175 |
| 82 | 13.33-13.49 (m, 1H), 8.14-8.24 (m, 1H), 7.88-7.99 (m, 1H), 7.25-7.37 (m, 1H), 6.96-7.09 (m, 1H), 4.16-4.29 (m, 2H), 3.91 (s, 3H), 3.80 (d, J = 5.52 Hz, 11H), 1.09 (s, 7H) | 500.06 | 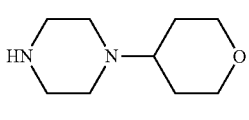<br>310<br>(Synthesized) | 2 | 175 |

TABLE 1-continued

| Compd. No. | ¹H NMR (400 MHz, DMSO-d6) δppm | Mass Spectrum (ESI): m/z [M + H] | Compound (1b) (mg) (Source) | Scheme No. | Compound (1a or 2a) (mg) |
|---|---|---|---|---|---|
| 84 | 13.29-13.41 (m, 1H), 7.97-8.01 (m, 1H), 5.06-5.17 (m, 1H), 4.55-4.66 (m, 1H), 4.17-4.21 (m, 1H), 3.71-3.88 (m, 11H), 3.00-3.12 (m, 1H), 2.65-2.78 (m, 1H), 2.36-2.44 (m, 3H), 1.73-1.89 (m, 2H), 1.47-1.61 (m, 1H), 1.18-1.39 (m, 2H), 1.05 (s, 6H) | 486.21 | 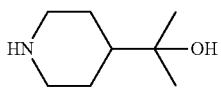 235 (Synthesized) | 2 | 170 |
| 85 | 13.22-13.54 (m, 1H), 7.87-8.14 (m, 1H), 7.24-7.50 (m, 1H), 6.75-6.92 (m, 1H), 4.91-5.11 (m, 1H), 4.32-4.59 (m, 1H), 3.70-3.87 (m, 11H), 3.61-3.69 (m, 1H), 3.21-3.30 (m, 1H), 2.86-2.97 (m, 1H), 2.41 (s, 3H), 1.75-1.88 (m, 2H), 1.46-1.71 (m, 2H) | 471.37 | 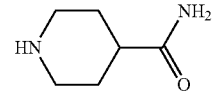 210 (Acros) | 2 | 170 |
| 86 | 13.22-13.49 (m, 1H), 7.99 (d, J = 4.02 Hz, 1H), 4.82 (d, J = 4.02 Hz, 1H), 4.46-4.60 (m, 1H), 4.01-4.11 (m, 1H), 3.74-3.87 (m, 12H), 3.61-3.73 (m, 2H), 2.41 (s, 3H), 1.78-1.88 (m, 2H), 1.32-1.53 (m, 2H) | 444.36 | 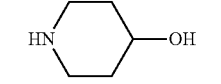 166 (Acros) | 2 | 170 |
| 103* | 7.94 (d, J = 0.76 Hz, 1H), 7.89 (s, 1H), 7.77-7.84 (m, 1H), 6.66 (s, 1H), 3.95 (s, 4H), 3.90-3.94 (m, 7H), 3.69-3.79 (m, 4H), 3.60 (d, J = 5.81 Hz, 2H), 2.66 (t, J = 6.19 Hz, 2H), 2.57 (d, J = 4.04 Hz, 4H) | 441.1 | 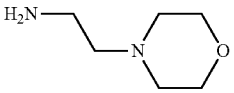 2.7 (Aldrich) | 2 | 1.5 |
| 109 | 13.12-13.37 (m, 1H), 8.18-8.28 (m, 1H), 7.98 (s, 1H), 6.79-6.88 (m, 1H), 4.89-5.05 (m, 1H), 4.42-4.56 (m, 1H), 3.88 (s, 7H), 3.79 (br. s., 4H), 3.46-3.59 (m, 2H), 3.13-3.26 (m, 1H), 2.79-2.90 (m, 1H), 2.69-2.78 (m, 2H), 1.76-1.89 (m, 5H), 1.31-1.51 (m, 2H), 1.04 (d, J = 6.32 Hz, 6H) | 509.37 | 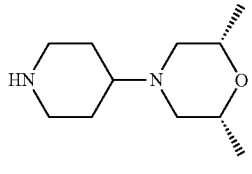 720 (Synthesized) | 2 | 800 |
| 115* | 8.15 (t, J = 5.81 Hz, 1H), 7.98 (s, 1H), 7.87 (s, 1H), 6.67 (s, 1H), 3.90-3.97 (m, 11H), 3.76 (t, J = 4.67 Hz, 4H), 3.62 (q, J = 6.23 Hz, 2H), 2.44-2.57 (m, 6H), 1.84 (quin, J = 6.38 Hz, 2H) | 455.3 | 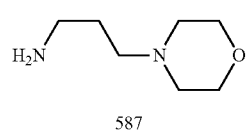 587 (TCI) | 2 | 600 |
| 116* | 8.27 (t, J = 6.32 Hz, 1H), 7.97 (s, 1H), 7.84 (s, 1H), 6.64 (s, 1H), 3.96 (d, J = 3.54 Hz, 8H), 3.89 (s, 3H), 3.35-3.53 (m, 6H), 2.41 (t, J = 8.08 Hz, 2H), 2.03 (quin, J = 7.52 Hz, 2H), 1.86 (quin, J = 6.25 Hz, 2H) | 455.3 | 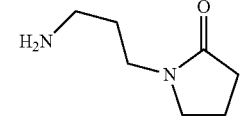 514 (Acros) | 2 | 530 |
| 117 | 13.12-13.27 (m, 1H), 8.19-8.25 (m, 1H), 7.94-7.99 (m, 1H), 6.79-6.86 (m, 1H), 4.99-5.10 (m, 1H), 4.56-4.65 (m, 1H), 4.15-4.20 (m, 1H), 3.88 (s, 7H), 3.77-3.81 (m, 4H), 3.01-3.09 (m, 1H), 2.67-2.74 (m, 1H), 1.72-1.88 (m, 2H), 1.45-1.60 (m, 1H), 1.19-1.27 (m, 2H), 1.05 (s, 6H) | 454.29 | 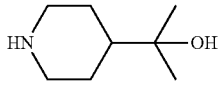 194 (Synthesized) | 2 | 300 |

TABLE 1-continued

| Compd. No. | ¹H NMR (400 MHz, DMSO-d6) δppm | Mass Spectrum (ESI): m/z [M + H] | Compound (1b) (mg) (Source) | Scheme No. | Compound (1a or 2a) (mg) |
|---|---|---|---|---|---|
| 122 | 13.27-13.62 (m, 1H), 8.24 (s, 1H), 7.93 (s, 1H), 7.57 (s, 1H), 4.19-4.28 (m, 4H), 3.94-4.01 (m, 1H), 3.88 (s, 3H), 3.70-3.80 (m, 6H), 3.49-3.60 (m, 1H), 3.11 (s, 2H), 2.15 (s, 2H), 1.62 (d, J = 5.05 Hz, 4H) | 466 | 200 (Synthesized) | 1 | 18 |
| 124 | 13.33-13.62 (m, 1H), 8.54-8.81 (m, 1H), 8.10-8.34 (m, 1H), 7.82-7.99 (m, 1H), 3.91 (s, 3H), 3.83-3.89 (m, 4H), 3.76-3.82 (m, 4H), 3.56-3.64 (m, 4H), 3.40-3.42 (m, 2H), 2.30-2.41 (m, 6H), 1.66-1.76 (m, 2H) | 472.97 | 96.25 (TCI) | 1 | NA |
| 126 | 13.39-13.74 (m, 1H), 8.18 (d, J = 2.51 Hz, 1H), 7.92 (s, 1H), 4.64-4.72 (m, 1H), 4.40-4.46 (m, 1H), 4.06-4.16 (m, 1H), 3.73-4.00 (m, 12H), 3.61 (br. s., 4H), 3.18-3.25 (m, 1H), 2.37 (br. s., 4H) | 470.96 | 75 (Synthesized) | 1 | 40 |
| 127 | 10.41-11.00 (m, 1H), 8.19 (d, J = 1.25 Hz, 1H), 7.89 (d, J = 2.01 Hz, 1H), 4.65-4.76 (m, 1H), 4.46-4.58 (m, 1H), 4.14-4.23 (m, 1H), 4.03-4.13 (m, 1H), 3.92 (s, 3H), 3.81-3.88 (m, 8H), 3.59-3.71 (m, 2H), 3.17-3.27 (m, 1H), 2.59-2.72 (m, 2H), 1.67 (d, J = 9.29 Hz, 2H), 1.14 (dd, J = 2.76, 6.27 Hz, 6H) | 498.99 | 91 (Synthesized) | 1 | 60 |

*400 MHz, MeOH-d4
**400 MHz, CDCl₃ was prepared as follows: To a solution of compound 51 (60 mg, 0.125 mmole) in tetrahydrofuran (8 mL) was added the solution of lithium hydroxide (21 mg, 0.5 mmole) in water (4 mL) and the reaction mixture was stirred at room temperature for 14 hours. The solvent was evaporated to dryness under vacuum. Water was added to the residue and washed with ethyl acetate (50 mL twice). The aqueous layer was acidified by hydrochloric acid solution (1N, pH6), then the precipitate formed was filtered and dried to obtain 25 mg of compound 50.

1H NMR (400 MHz, DMSO-d6) δ ppm: 13.42-13.57 (m, 1H), 12.07-12.25 (m, 1H), 8.21-8.26 (m, 1H), 7.90-7.96 (m, 1H), 4.88-4.96 (m, 1H), 4.42-4.52 (m, 1H), 4.14-4.36 (m, 4H), 3.88 (s, 3H), 3.73-3.80 (m, 4H), 3.16-3.26 (m, 1H), 2.81-2.91 (m, 1H), 2.17-2.25 (m, 2H), 1.94-2.07 (m, 1H), 1.71-1.85 (m, 2H), 1.11-1.21 (m, 2H). Mass Spectrum (ESI): m/z 455.11 [M+H].

TABLE 2

| Compd. No. | ¹H NMR (400 MHz, DMSO-d6) δppm | Mass Spectrum (ESI): m/z [M + H] | Compound 3b (mg) (Source) | Scheme No. | Compound (3a or 4a) (mg) |
|---|---|---|---|---|---|
| 16 | 13.32-13.56 (m, 1H), 7.90 (s, 1H), 4.86-4.96 (m, 1H), 4.43-4.53 (m, 1H), 4.03-4.38 (m, 4H), 3.74-3.79 (m, 7H), 3.52-3.60 (m, 4H), 3.16-3.32 (m, 2H), 2.81-2.94 (m, 1H), 2.68 (s, 3H), 2.45-2.49 (m, 4H), 1.78-1.94 (m, 2H), 1.31-1.51 (m, 2H) | 496.54 | 71 (Combiblock) | 3 | 100 |
| 17 | 13.51-13.71 (m, 1H), 8.44 (s, 1H), 4.76-4.89 (m, 1H), 4.44-4.52 (m, 1H), 4.10-4.42 (m, 4H), 3.97 (s, 3H), 3.74 (t, J = 4.64 Hz, 4H), 3.54-3.60 (m, 5H), 3.19-3.27 (m, 1H), 2.83-2.96 (m, 1H), 2.47 (br. s., 4H), 1.79-1.96 (m, 2H), 1.29-1.49 (m, 2H) | 550.26 | 89 (Combiblock) | 3 | 100 |
| 18 | 13.46 (br. s., 1H), 8.26 (s, 1H), 7.95 (s, 1H), 4.91 (br. s., 1H), 4.52-4.61 (m, 1H), 4.47 (d, J = 12.55 Hz, 1H), 4.25 (br. s., 4H), 3.76 (br. s., 4H), 3.57 (br. s., 4H), 3.23 (br. s., 2H), 2.88 (br. s., 1H), 2.47 (br. s., 4H), 1.85 (d, J = 15.81 Hz, 2H), 1.35-1.49 (m, 8H) | 510.54 | 81 (Aldrich) | 3 | 100 |
| 19 | 13.68-13.81 (m, 1H), 13.54-13.64 (m, 1H), 8.36-8.50 (m, 1H), 4.76-4.87 (m, 1H), 4.43-4.53 (m, 1H), 4.05-4.39 (m, 4H), 3.74 (t, J = 4.64 Hz, 4H), 3.53-3.63 (m, 4H), 3.16-3.28 (m, 2H), 2.84-2.95 (m, 1H), 2.47 (br. s., 4H), 1.80-1.95 (m, 2H), 1.30-1.46 (m, 2H) | 536.51 | 84 (Combiblock) | 3 | 100 |
| 21 | 8.22-8.41 (m, 1H), 7.89-8.04 (m, 1H), 4.42-4.52 (m, 1H), 4.14-4.39 (m, 6H), 4.06-4.14 (m, 1H), 3.84-3.94 (m, 3H), 3.71-3.78 (m, 4H), 3.15-3.23 (m, 1H), 2.91-2.99 (m, 1H), 2.31-2.43 (m, 1H), 2.17 (s, 6H), 1.85-1.92 (m, 1H), 1.74-1.80 (m, 1H), 1.32-1.41 (m, 5H) | 468.11 | 69.15 (Aldrich) | 3 | 100 |

TABLE 2-continued

| Compd. No. | ¹H NMR (400 MHz, DMSO-d6) δppm | Mass Spectrum (ESI): m/z [M + H] | Compound 3b (mg) (Source) | Scheme No. | Compound (3a or 4a) (mg) |
|---|---|---|---|---|---|
| 22 | 8.30 (s, 1H), 8.23-8.50 (m, 1H), 7.98 (s, 1H), 4.48 (d, J = 13.14 Hz, 1H), 4.17-4.40 (m, 5H), 4.12 (d, J = 13.39 Hz, 1H), 3.89 (s, 3H), 3.75 (br. s., 5H), 3.57 (br. s., 4H), 3.12-3.21 (m, 1H), 2.89-2.97 (m, 1H), 2.46 (br. s., 4H), 1.92 (d, J = 12.38 Hz, 1H), 1.80 (d, J = 12.13 Hz, 1H), 1.31-1.45 (m, 5H) | 510.11 | 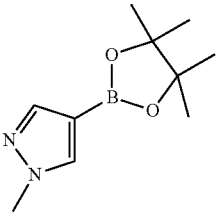<br>60.89 (Aldrich) | 3 | 100 |
| 23 | 8.30 (s, 1H), 7.99 (s, 1H), 4.43-4.51 (m, 1H), 4.21 (br. s., 7H), 3.89 (s, 3H), 3.67-3.82 (m, 7H), 3.57 (br. s., 4H), 3.11-3.21 (m, 1H), 2.87-2.96 (m, 1H), 2.47 (br. s., 4H), 1.74-1.99 (m, 2H), 1.33-1.51 (m, 2H) | 496.12 | 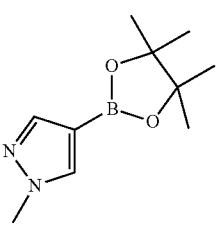<br>71.54 (Aldrich) | 3 | 100 |
| 24 | 9.87-10.19 (m, 1H), 8.21-8.43 (m, 1H), 7.92-8.11 (m, 1H), 4.59-4.68 (m, 1H), 4.43-4.51 (m, 1H), 4.09-4.39 (m, 4H), 3.89 (s, 3H), 3.79 (s, 7H), 3.11-3.22 (m, 1H), 2.83-2.94 (m, 1H), 2.66-2.79 (s, 6H), 2.00-2.19 (m, 2H), 1.58-1.74 (m, 2H) | 510.11 | 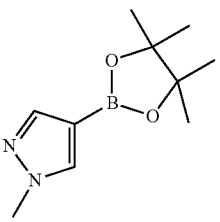<br>64.71 (Aldrich) | 3 | 100 |
| 39 | 8.03-8.12 (m, 1H), 7.89-7.98 (m, 1H), 4.47-4.63 (m, 2H), 4.15-4.42 (m, 4H), 3.88 (s, 3H), 3.84-3.87 (m, 1H), 3.74-3.84 (m, 6H), 3.67-3.74 (m, 2H), 3.49-3.61 (m, 2H), 2.11 (s, 3H) | 440.54 | 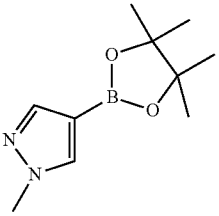<br>33 (Aldrich) | 3 | 45 |
| 40 | 13.27-13.52 (m, 1H), 7.80-8.02 (m, 1H), 4.87-4.98 (m, 1H), 4.42-4.53 (m, 1H), 3.93-4.38 (m, 5H), 3.77 (br. s., 7H), 3.57 (br. s., 4H), 3.13-3.17 (m, 1H), 2.82-2.94 (m, 1H), 2.68 (s, 3H), 2.44-2.48 (m, 4H), 1.80-1.96 (m, 2H), 1.28-1.51 (m, 2H) | 496.58 | 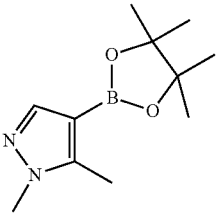<br>71 (Combiblock) | 3 | 100 |

TABLE 2-continued

| Compd. No. | ¹H NMR (400 MHz, DMSO-d6) δppm | Mass Spectrum (ESI): m/z [M + H] | Compound 3b (mg) (Source) | Scheme No. | Compound (3a or 4a) (mg) |
|---|---|---|---|---|---|
| 41 | 13.22-13.52 (m, 1H), 8.04-8.22 (m, 1H), 4.82-4.96 (m, 1H), 4.43-4.52 (m, 1H), 4.01-4.36 (m, 5H), 3.80 (s, 3H), 3.70-3.78 (m, 4H), 3.49-3.60 (m, 4H), 3.18-3.27 (m, 1H), 2.82-2.93 (m, 1H), 2.41-2.48 (m, 4H), 2.43-2.48 (s, 3H) 1.80-1.95 (m, 2H), 1.34-1.53 (m, 2H) | 496.58 | 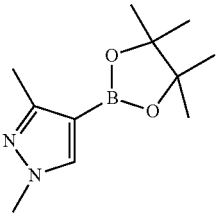<br>71<br>(Aldrich) | 3 | 100 |
| 42 | 13.31-13.61 (m, 1H), 12.84-13.22 (m, 1H), 8.17-8.42 (m, 1H), 7.81-8.16 (m, 1H), 4.86-4.99 (m, 1H), 4.43-4.54 (m, 1H), 3.87-4.39 (m, 4H), 3.75 (t, J = 4.39 Hz, 5H), 3.57 (br. s., 4H), 3.19-3.27 (m, 1H), 2.83-2.93 (m, 1H), 2.47 (br. s., 4H), 1.83-1.95 (m, 2H), 1.34-1.49 (m, 2H) | 496.58 | 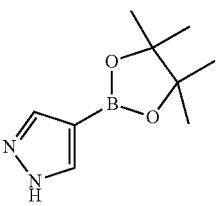<br>62<br>(Combiblock) | 3 | 100 |
| 47# | 13.14-13.74 (m, 1H), 8.40-8.46 (m, 1H), 8.23 (s, 1H), 7.92 (s, 1H), 4.20-4.45 (m, 4H), 3.88 (s, 3H), 3.78 (d, J = 4.52 Hz, 5H), 2.77-2.84 (m, 2H), 2.18 (s, 3H), 1.91-2.03 (m, 2H), 1.67-1.80 (m, 4H) | 426.16 | 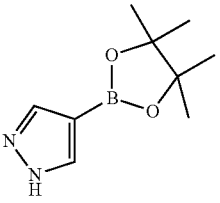<br>226<br>(Combiblock) | 3 | 350 |
| 49 | 13.47-13.67 (m, 1H), 8.38-8.47 (m, 1H), 8.21-8.26 (m, 1H), 7.89-7.95 (m, 1H), 7.22-7.39 (m, 5H), 4.13-4.39 (m, 4H), 3.88 (s, 3H), 3.74-3.83 (m, 5H), 3.43-3.52 (m, 2H), 2.79-2.88 (m, 2H), 1.96-2.09 (m, 2H), 1.65-1.83 (m, 4H) | 502.28 | 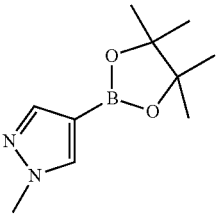<br>32<br>(Aldrich) | 3 | 50 |
| 52 | 13.58-13.69 (m, 1H), 8.64-8.70 (m, 1H), 8.22-8.26 (m, 1H), 7.90-7.95 (m, 1H), 4.15-4.49 (m, 4H), 3.89 (s, 3H), 3.75-3.80 (m, 4H), 3.43-3.52 (m, 4H), 3.27 (s, 3H) | 387.2 | 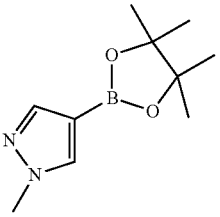<br>61<br>(Aldrich) | 3 | 100 |

TABLE 2-continued

| Compd. No. | ¹H NMR (400 MHz, DMSO-d6) δppm | Mass Spectrum (ESI): m/z [M + H] | Compound 3b (mg) (Source) | Scheme No. | Compound (3a or 4a) (mg) |
|---|---|---|---|---|---|
| 54 | 13.31-13.71 (m, 1H), 12.94-13.24 (m, 1H), 8.15-8.31 (m, 1H), 7.94-8.12 (m, 1H), 4.90-5.14 (m, 1H), 4.46-4.55 (m, 1H), 4.13-4.37 (m, 4H), 3.72-3.80 (m, 4H), 3.15-3.28 (m, 2H), 2.82-2.92 (m, 1H), 2.20-2.38 (m, 6H), 1.84-1.98 (m, 2H), 1.34-1.55 (m, 2H) | 426.99 | 69 (Combiblock) | 3 | 100 |
| 55 | 13.27-13.66 (m, 1H), 8.24-8.28 (m, 1H), 7.93-7.98 (m, 1H), 4.91-5.11 (m, 1H), 4.46-4.55 (m, 1H), 4.17-4.36 (m, 4H), 4.08-4.14 (m, 2H), 3.73-3.80 (m, 4H), 3.15-3.29 (m, 2H), 2.82-2.92 (m, 1H), 2.24-2.38 (m, 6H), 1.78-1.95 (m, 4H), 1.34-1.54 (m, 2H), 0.82-0.87 (m, 3H) | 469.11 | 85 (Aldrich) | 3 | 100 |
| 56 | 12.82-13.96 (m, 1H), 8.25-8.30 (m, 1H), 7.92-7.98 (m, 1H), 4.89-5.02 (m, 1H), 4.45-4.53 (m, 1H), 4.07-4.39 (m, 6H), 3.73-3.79 (m, 4H), 3.18-3.29 (m, 2H), 2.83-2.94 (m, 1H), 2.26 (br. s., 6H), 1.81-1.95 (m, 2H), 1.40 (s, 5H) | 455.54 | 80 (Aldrich) | 3 | 100 |
| 57 | 13.00-13.97 (m, 1H), 8.24 (s, 1H), 7.93 (s, 1H), 4.87-5.01 (m, 1H), 4.44-4.53 (m, 1H), 4.16-4.37 (m, 4H), 3.89 (s, 3H), 3.75 (br. s., 4H), 3.18-3.28 (m, 2H), 2.82-2.94 (m, 1H), 2.23 (s, 6H), 1.80-1.95 (m, 2H), 1.32-1.49 (m, 2H) | 440.17 | 75 (Aldrich) | 3 | 100 |
| 58 | 13.41-13.53 (m, 1H), 8.23 (s, 1H), 7.93 (s, 1H), 4.85-4.97 (m, 1H), 4.43-4.53 (m, 1H), 4.08-4.39 (m, 4H), 3.88 (s, 3H), 3.76 (d, J = 4.77 Hz, 4H), 3.56 (d, J = 4.27 Hz, 4H), 3.17-3.29 (m, 2H), 2.83-2.94 (m, 1H), 2.46 (d, J = 5.02 Hz, 4H), 1.78-1.94 (m, 2H), 1.30-1.48 (m, 2H) | 482.16 | 67 (Aldrich) | 3 | 100 |

TABLE 2-continued

| Compd. No. | ¹H NMR (400 MHz, DMSO-d6) δppm | Mass Spectrum (ESI): m/z [M + H] | Compound 3b (mg) (Source) | Scheme No. | Compound (3a or 4a) (mg) |
|---|---|---|---|---|---|
| 65 | 13.35-13.59 (m, 1H), 12.95-13.15 (m, 1H), 8.12-8.43 (m, 1H), 7.94-8.12 (m, 1H), 4.89-5.00 (m, 1H), 4.44-4.53 (m, 1H), 4.11-4.42 (m, 4H), 3.76 (t, J = 4.64 Hz, 4H), 3.47-3.55 (m, 2H), 3.15-3.24 (m, 1H), 2.81-2.90 (m, 1H), 2.68-2.78 (m, 2H), 1.77-1.92 (m, 4H), 1.34 (s, 3H), 1.04 (d, J = 6.27 Hz, 6H) | 496.23 | 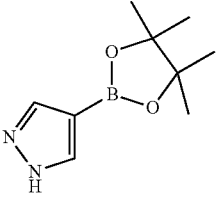<br>81.70 (Combiblock) | 3 | 130 |
| 66* | 8.25 (br. s., 1H), 5.74 (d, J = 14.81 Hz, 1H), 4.76 (d, J = 14.05 Hz, 1H), 4.34 (br. s., 4H), 3.88 (br. s., 4H), 3.74 (br. s., 5H), 3.26-3.38 (m, 1H), 2.91 (br. s., 1H), 2.76 (br. s., 3H), 2.48-2.65 (m, 6H), 1.99 (br. s., 2H), 1.63 (br. s., 2H) | 482.26 | 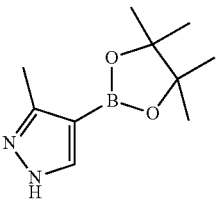<br>86.29 (Aldrich) | 3 | 120 |
| 72 | 13.34-13.62 (m, 1H), 12.63-13.25 (m, 1H), 7.55-8.39 (m, 2H), 4.36 (s, 4H), 4.17-4.32 (m, 4H), 3.94-4.05 (m, 2H), 3.76 (t, J = 4.64 Hz, 4H), 3.52-3.63 (m, 2H), 1.86 (d, J = 3.76 Hz, 4H) | 425.19 | 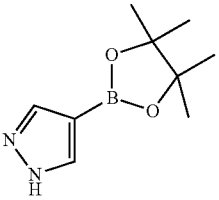<br>59.38 (Combiblock) | 3 | 80 |
| 74 | 13.37-13.67 (m, 1H), 12.89-13.17 (m, 1H), 8.13-8.38 (m, 1H), 7.86-8.08 (m, 1H), 5.03-5.28 (m, 1H), 4.45-4.71 (m, 2H), 4.13-4.41 (m, 4H), 4.04 (s, 2H), 3.75 (t, J = 4.64 Hz, 6H), 3.25-3.30 (m, 2H), 3.20-3.24 (m, 1H), 2.83-2.95 (m, 1H), 1.60-1.84 (m, 4H) | 482.26 | 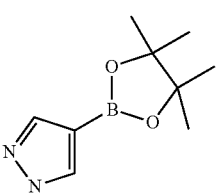<br>71.29 (Combiblock) | 3 | 110 |
| 87 | 1H NMR (400 MHz, DMSO-d6) d 8.05 (d, J = 4.29 Hz, 1H), 4.45-4.54 (m, 1H), 4.24-4.35 (m, 1H), 3.71-3.88 (m, 14H), 3.57 (t, J = 4.42 Hz, 4H), 3.09-3.21 (m, 1H), 2.86-2.98 (m, 1H), 2.40-2.60 (m, 8H), 1.78-1.97 (m, 2H), 1.34-1.56 (m, 2H) | 527.52 | 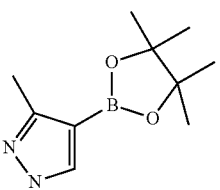<br>1.26 (Aldrich) | 3 | 2.45 |

TABLE 2-continued

| Compd. No. | ¹H NMR (400 MHz, DMSO-d6) δppm | Mass Spectrum (ESI): m/z [M + H] | Compound 3b (mg) (Source) | Scheme No. | Compound (3a or 4a) (mg) |
|---|---|---|---|---|---|
| 88 | 13.02-13.40 (m, 1H), 5.05-5.20 (m, 1H), 4.44-4.56 (m, 1H), 3.78 (t, J = 4.52 Hz, 4H), 3.71 (s, 3H), 3.44-3.62 (m, 8H), 3.18-3.28 (m, 1H), 2.83-2.94 (m, 1H), 2.45-2.55 (m, 5H), 2.07 (d, J = 9.29 Hz, 6H), 1.97 (s, 3H), 1.81-1.94 (m, 2H), 1.31-1.55 (m, 2H) | 523.32 | 77 (Labex) | 4 | 120 |
| 89 | 13.04-13.39 (m, 1H), 7.78 (s, 1H), 5.04-5.19 (m, 1H), 4.38-4.63 (m, 1H), 3.70-3.87 (m, 7H), 3.41-3.61 (m, 8H), 3.19-3.29 (m, 1H), 2.83-2.95 (m, 1H), 2.39-2.48 (m, 5H), 2.15-2.28 (m, 6H), 1.90 (br. s., 2H), 1.31-1.56 (m, 2H) | 509.29 | 70 (Aldrich) | 4 | 120 |
| 90 | 13.10-13.35 (m, 1H), 8.07 (s, 1H), 7.83 (s, 1H), 5.06-5.18 (m, 1H), 4.45-4.56 (m, 1H), 3.91 (s, 3H), 3.79 (t, J = 4.52 Hz, 4H), 3.42-3.63 (m, 8H), 3.19-3.29 (m, 1H), 2.81-2.93 (m, 1H), 2.45-2.55 (m, 5H), 2.41 (s, 3H), 1.82-1.96 (m, 2H), 1.31-1.56 (m, 2H) | 495.25 | 66 (Aldrich) | 4 | 120 |
| 91 | 13.48-13.64 (m, 1H), 7.93 (s, 1H), 4.97-5.16 (m, 1H), 4.43-4.58 (m, 1H), 3.74-3.86 (m, 7H), 3.53-3.72 (m, 8H), 3.19-3.29 (m, 1H), 2.85-2.98 (m, 1H), 2.47 (br. s., 5H), 2.21 (s, 3H), 1.83-1.95 (m, 2H), 1.30-1.59 (m, 2H) | 529.16 | 81 (Aldrich) | 4 | 145 |
| 92 | 13.53 (br. s., 1H), 8.31 (s, 1H), 7.99 (s, 1H), 4.97-5.12 (m, 1H), 4.42-4.56 (m, 1H), 3.92 (s, 3H), 3.73-3.85 (m, 5H), 3.51-3.70 (m, 8H), 3.17-3.29 (m, 1H), 2.83-2.96 (m, 1H), 2.47 (br. s., 4H), 1.80-2.00 (m, 2H), 1.32-1.56 (m, 2H) | 515.06 | 112 (Aldrich) | 4 | 200 |

TABLE 2-continued

| Compd. No. | ¹H NMR (400 MHz, DMSO-d6) δppm | Mass Spectrum (ESI): m/z [M + H] | Compound 3b (mg) (Source) | Scheme No. | Compound (3a or 4a) (mg) |
|---|---|---|---|---|---|
| 94 | 12.92-13.37 (m, 1H), 8.12 (s, 1H), 6.69 (s, 1H), 4.86-5.02 (m, 1H), 4.41-4.57 (m, 1H), 3.73-3.93 (m, 11H), 3.50-3.63 (m, 4H), 3.15-3.27 (m, 1H), 2.78-2.93 (m, 1H), 2.42-2.49 (m, 8H), 1.77-1.95 (m, 2H), 1.30-1.53 (m, 2H) | 495.4 | 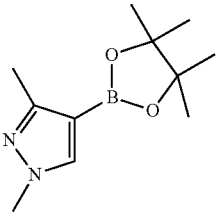<br>66<br>(Aldrich) | 3 | 100 |
| 95 | 13.38 (br. S., 1H), 7.66 (d, J = 3.76 Hz, 1H), 4.91-5.18 (m, 1H), 4.41-4.64 (m, 1H), 3.70-3.88 (m, 11H), 3.57 (t, J = 4.39 Hz, 4H), 3.17-3.27 (m, 1H), 2.82-2.94 (m, 1H), 2.47 (br. S., 8H), 1.89 (br. S., 2H), 1.31-1.55 (m, 2H) | 513.12 | 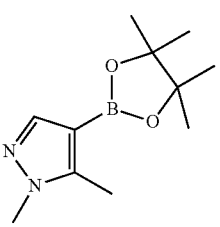<br>78<br>(Combiblock) | 4 | 140 |
| 96 | 13.36 (s, 1H), 7.99 (d, J = 4.02 Hz, 1H), 4.98-5.19 (m, 1H), 4.41-4.69 (m, 1H), 3.71-3.85 (m, 11H), 3.57 (t, J = 4.52 Hz, 4H), 3.22 (br. S., 1H), 2.83-2.94 (m, 1H), 2.48 (m, 5H), 2.41 (s, 3H), 1.89 (br. S., 2H), 1.24-1.57 (m, 2H) | 513.62 | 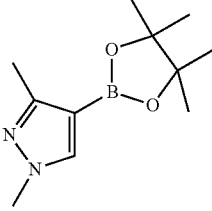<br>1.266<br>(Aldrich) | 4 | 2.45 |
| 97 | 13.12-13.55 (m, 1H), 7.95-8.04 (m, 1H), 4.85-5.07 (m, 1H), 4.35-4.58 (m, 1H), 3.80 (d, J = 13.55 Hz, 11H), 3.17-3.27 (m, 1H), 2.82-2.95 (m, 1H), 2.41 (s, 4H), 2.19 (s, 6H), 1.79-1.92 (m, 2H), 1.30-1.51 (m, 2H) | 471.58 | 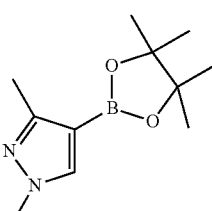<br>64<br>(Aldrich) | 4 | 110 |
| 98 | 13.14-13.56 (m, 1H), 8.07-8.26 (m, 1H), 7.81-8.02 (m, 1H), 4.94-5.14 (m, 1H), 4.44-4.64 (m, 1H), 3.91 (s, 3H), 3.71-3.86 (m, 8H), 3.54-3.62 (m, 4H), 3.16-3.26 (m, 1H), 2.81-2.94 (m, 1H), 2.43-2.49 (m, 5H), 1.81-1.95 (m, 2H), 1.30-1.54 (m, 2H) | 499.5 | 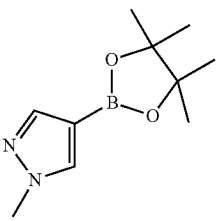<br>66<br>(Aldrich) | 4 | 140 |

TABLE 2-continued

| Compd. No. | ¹H NMR (400 MHz, DMSO-d6) δppm | Mass Spectrum (ESI): m/z [M + H] | Compound 3b (mg) (Source) | Scheme No. | Compound (3a or 4a) (mg) |
|---|---|---|---|---|---|
| 99 | 13.13-13.63 (m, 1H), 8.14-8.24 (m, 1H), 7.85-7.96 (m, 1H), 4.92-5.06 (m, 1H), 4.35-4.55 (m, 1H), 3.92 (s, 3H), 3.73-3.86 (m, 8H), 3.16-3.27 (m, 1H), 2.81-2.94 (m, 1H), 2.35-2.47 (m, 1H), 2.19 (s, 6H), 1.78-1.91 (m, 2H), 1.31-1.53 (m, 2H) | 457.47 | 48 (Aldrich) | 4 | 120 |
| 100 | 8.30 (s, 1H), 8.04 (s, 1H), 6.90 (s, 1H), 5.76 (s, 1H), 4.42-4.69 (m, 2H), 3.86-3.97 (m, 7H), 3.74-3.85 (m, 7H), 3.10-3.22 (m, 1H), 2.82-2.95 (m, 1H), 2.69 (br. s., 6H), 1.96-2.16 (m, 2H), 1.52-1.70 (m, 2H) | 453.44 | 75 (Aldrich) | 3 | 120 |
| 101 | 13.15-13.35 (m, 1H), 8.24 (s, 1H), 8.98 (s, 1H), 6.84 (s, 1H), 4.95-5.1 (m, 2H), 4.4-4.6 (m, 1H), 3.7-3.96 (m, 11H), 3.15-3.25 (m, 1H), 2.81-2.91 (m, 1H), 2.29 (br. s., 6H), 1.8-2.0 (m, 2H), 1.32-1.62 (m, 2H) | 439.33 | 69 (Aldrich) | 3 | 100 |
| 102 | 13.10-13.32 (m, 1H), 8.23 (s, 1H), 7.97 (s, 1H), 6.84 (s, 1H), 4.88-5.06 (m, 1H), 4.40-4.54 (m, 1H), 3.84-3.95 (m, 7H), 3.72-3.82 (m, 4H), 3.51-3.62 (m, 4H), 3.15-3.26 (m, 1H), 2.81-2.92 (m, 1H), 2.42-2.49 (m, 5H), 1.80-1.94 (m, 2H), 1.30-1.50 (m, 2H) | 481.39 | 68 (Aldrich) | 3 | 110 |
| 105* | 8.29 (s, 1H), 7.87 (d, J = 2.53 Hz, 1H), 7.62 (t, J = 5.05 Hz, 1H), 3.95 (s, 4H), 3.67-3.81 (m, 12H), 3.56 (d, J = 5.31 Hz, 2H), 2.69 (t, J = 5.81 Hz, 2H), 2.60 (br. s., 4H) | 459.2 | 86 (Aldrich) | 4 | 160 |

TABLE 2-continued

| Compd. No. | ¹H NMR (400 MHz, DMSO-d6) δppm | Mass Spectrum (ESI): m/z [M + H] | Compound 3b (mg) (Source) | Scheme No. | Compound (3a or 4a) (mg) |
|---|---|---|---|---|---|
| 106 | 8.30 (s, 1H), 8.04 (s, 1H), 6.88 (s, 1H), 4.42-4.58 (m, 1H), 4.14-4.34 (m, 1H), 3.83-3.98 (m, 7H), 3.75-3.82 (m, 7H), 3.59 (br. s., 4H), 3.07-3.25 (m, 2H), 2.75-3.03 (m, 2H), 1.72-2.10 (m, 3H), 1.35-1.54 (m, 2H), 1.23 (s, 2H) | 495.25 | 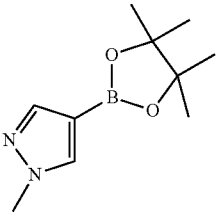<br>60<br>(Aldrich) | 3 | 100 |
| 111 | 8.25 (s, 1H), 8.00 (s, 1H), 4.41-4.54 (m, 1H), 4.25-4.34 (m, 1H), 3.92 (s, 3H), 3.68-3.89 (m, 12H), 3.57 (br. s., 4H), 3.09-3.20 (m, 1H), 2.87-2.99 (m, 1H), 2.44-2.48 (m, 4H), 1.80-1.97 (m, 2H), 1.34-1.53 (m, 2H) | 513.36 | 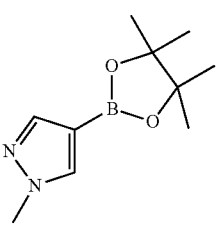<br>116<br>(Aldrich) | 3 | 200 |
| 112 | 8.06 (d, J = 4.27 Hz, 1H), 4.44-4.54 (m, 1H), 4.25-4.35 (m, 1H), 3.75-3.84 (m, 14H), 3.47-3.58 (m, 2H), 3.15 (br. s., 1H), 2.90 (br. s., 1H), 2.75 (d, J = 10.29 Hz, 2H), 2.49 (d, J = 1.25 Hz, 4H), 1.75-1.93 (m, 4H), 1.36-1.56 (m, 2H), 1.05 (dd, J = 2.13, 6.15 Hz, 6H) | 555.45 | 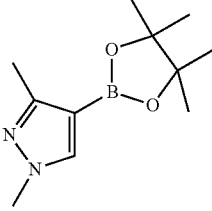<br>58<br>(Aldrich) | 3 | 100 |
| 114 | 1H NMR (400 MHz. DMSO-d6) Shift 8.24 (s, 1H), 6.77 (s, 1H), 4.43-4.53 (m, 1H), 4.19-4.28 (m, 1H), 3.85-3.90 (m, 4H), 3.75-3.83 (m, 10H), 3.46-3.57 (m, 2H), 3.15 (br. s., 1H), 2.89 (br. s., 1H), 2.74 (d, J = 10.54 Hz, 2H), 2.48-2.50 (m, 4H), 1.74-1.94 (m, 4H), 1.35-1.54 (m, 2H), 1.04 (dd, J = 2.26, 6.27 Hz, 6H) | 537.44 | 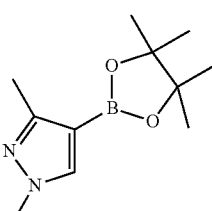<br>132<br>(Aldrich) | 3 | 250 |
| 113 | 13.21 (s, 1H), 8.13 (s, 1H), 6.70 (s, 1H), 4.88-5.01 (m, 1H), 4.43-4.54 (m, 1H), 3.85 (d, J = 5.02 Hz, 4H), 3.78-3.82 (m, 6H), 3.47-3.56 (m, 2H), 3.19 (br. s., 1H), 2.85 (br. s., 1H), 2.74 (d, J = 10.54 Hz, 2H), 2.46 (s, 4H), 1.76-1.91 (m, 4H), 1.33-1.52 (m, 2H), 1.04 (d, J = 6.02 Hz, 6H) | 523.39 | 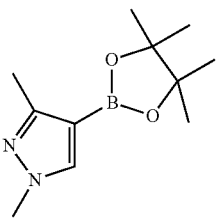<br>132<br>(Aldrich) | 4 | 250 |

TABLE 2-continued

| Compd. No. | ¹H NMR (400 MHz, DMSO-d6) δppm | Mass Spectrum (ESI): m/z [M + H] | Compound 3b (mg) (Source) | Scheme No. | Compound (3a or 4a) (mg) |
|---|---|---|---|---|---|
| 118 | 12.68-13.45 (m, 2H), 7.86-8.50 (m, 2H), 6.88 (s, 1H), 4.89-5.03 (m, 1H), 4.41-4.55 (m, 1H), 3.90 (d, J = 4.52 Hz, 4H), 3.80 (d, J = 4.77 Hz, 4H), 3.46-3.57 (m, 2H), 3.19 (br. s., 1H), 2.85 (br. s., 1H), 2.74 (d, J = 10.54 Hz, 2H), 1.72-1.92 (m, 4H), 1.36-1.52 (m, 2H), 1.04 (d, J = 6.27 Hz, 6H) | 495.34 | 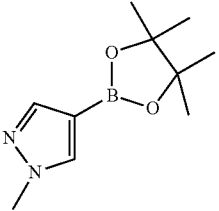 92 (Aldrich) | 4 | 200 |
| 120 | 13.20-13.45 (m, 1H), 8.23 (s, 1H), 7.97 (s, 1H), 6.83 (s, 1H), 4.61-4.70 (m, 1H), 4.36-4.45 (m, 1H), 4.05-4.14 (m, 1H), 3.93 (d, J = 5.05 Hz, 5H), 3.88 (s, 3H), 3.76-3.83 (m, 4H), 3.61 (t, J = 4.29 Hz, 4H), 3.18-3.25 (m, 1H), 2.36 (d, J = 4.29 Hz, 4H) | 452.97 | 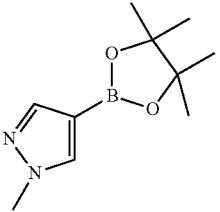 200 (Aldrich) | 4 | 110 |
| 123 | 13.81-14.01 (m, 1H), 13.37-13.64 (m, 1H), 8.15-8.30 (m, 1H), 4.90-4.99 (m, 1H), 4.43-4.54 (m, 1H), 3.71-3.86 (m, 8H), 3.57 (t, J = 4.29 Hz, 4H), 3.16-3.27 (m, 1H), 2.83-2.94 (m, 1H), 2.44-2.49 (m, 4H), 1.79-1.98 (m, 2H), 1.18-1.58 (m, 3H) | 552.97 | 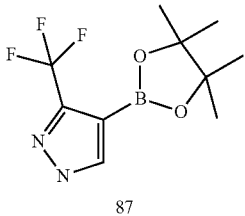 87 (Combiblock) | 3 | NA |
| 125 | 13.22-13.59 (m, 1H), 13.07-13.27 (m, 1H), 8.06-8.31 (m, 1H), 7.88-8.13 (m, 1H), 4.85-5.10 (m, 1H), 4.38-4.68 (m, 1H), 3.80 (d, J = 8.34 Hz, 8H), 3.57 (br. s., 4H), 3.16-3.26 (m, 2H), 2.81-2.93 (m, 1H), 2.44-2.48 (m, 4H), 1.89 (br. s., 2H), 1.31-1.57 (m, 2H) | 484.96 | 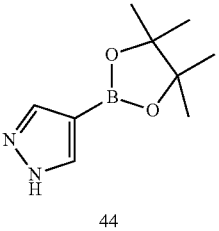 44 (Combiblock) | 3 | NA |
| 132 | 13.42-13.49 (m, 1H), 8.21-8.26 (m, 1H), 7.90-7.95 (m, 1H), 4.84-4.97 (m, 1H), 4.52-4.55 (m, 3H), 4.38-4.42 (m, 4H), 4.19-4.32 (m, 4H), 3.88 (s, 6H), 3.71-3.80 (m, 8H), 2.93-2.95 (m, 3H), 2.79-2.82 (m, 3H), 1.72-1.87 (m, 8H) | 481.98 | 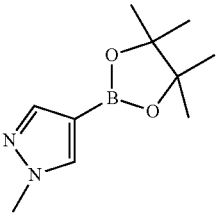 155 (Aldrich) | 4 | 90 |

TABLE 2-continued

| Compd. No. | ¹H NMR (400 MHz, DMSO-d6) δppm | Mass Spectrum (ESI): m/z [M + H] | Compound 3b (mg) (Source) | Scheme No. | Compound (3a or 4a) (mg) |
|---|---|---|---|---|---|
| 133 | 13.16-13.34 (m, 1H), 12.94-13.07 (m, 1H), 8.25-8.38 (m, 1H), 7.98-8.11 (m, 1H), 6.89 (s, 1H), 4.87-5.04 (m, 1H), 4.41-4.55 (m, 1H), 3.90 (d, J = 4.77 Hz, 4H), 3.76-3.84 (m, 4H), 3.57 (t, J = 4.27 Hz, 4H), 3.15-3.27 (m, 1H), 2.80-2.92 (m, 1H), 2.48 (br. s., 4H), 1.80-1.95 (m, 2H), 1.31-1.50 (m, 2H) | 467.21 | 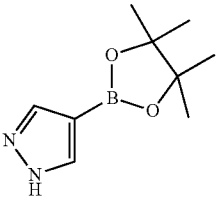<br>116 (Combiblock) | 3 | 100 |
| 134 | 13.74 (br. s., 1H), 13.37 (br. s., 1H), 8.38 (s, 1H), 6.75 (s, 1H), 4.83 (d, J = 13.55 Hz, 1H), 4.49 (d, J = 12.80 Hz, 1H), 3.87 (d, J = 4.52 Hz, 4H), 3.80 (d, J = 4.52 Hz, 4H), 3.57 (br. s., 4H), 3.21 (t, J = 11.67 Hz, 1H), 2.84-2.94 (m, 1H), 2.48 (br. s., 4H), 1.80-1.95 (m, 2H), 1.64-1.75 (m, 1H), 1.36-1.52 (m, 2H) | 535.23 | 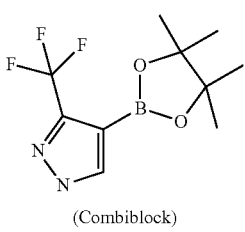 [SMILES: CC1(C)OB(c2c[nH]nc2C(F)(F)F)OC1(C)C]<br>(Combiblock) | 4 | 100 |
| 135 | 13.22-13.35 (m, 1H), 8.15-8.32 (m, 1H), 7.92-8.03 (m, 1H), 6.74-6.91 (m, 1H), 4.09-4.22 (m, 2H), 3.88 (s, 9H), 3.75-3.82 (m, 4H), 3.63-3.70 (m, 2H), 3.23-3.30 (m, 2H), 2.54-2.59 (m, 4H), 2.39-2.47 (m, 1H), 1.67-1.76 (m, 2H), 1.34-1.50 (m, 2H) | 481.22 | 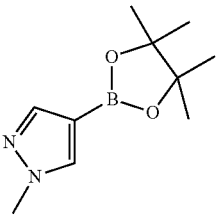<br>116 (Aldrich) | 4 | 48 |

*(400 MHz, CDCl₃)

Compound 47 was prepared as follows: To a solution of compound 49 (260 mg, 0.57 mmole) was added palladium on carbon powder (200 mg), and the reaction mixture was stirred for 24 hour under hydrogen atmosphere using balloon. The reaction mixture was filtered through celite and washed with methanol (50 mL); the filtrate was evaporated under vacuum and purified by column chromatography using methanol and dichloromethane (5% methanol) as eluent to obtain 30 mg of compound 47.

PI3K inhibitors of formula (I) as exemplified herein are shown in Table 3, below.

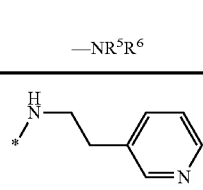

formula (I)

TABLE 3

| Compound No. | R¹ | R² | R³ | Y | R⁴ | —NR⁵R⁶ | PI3Kδ IC₅₀ (nM) |
|---|---|---|---|---|---|---|---|
| 1 | Me | H | H | N | H | 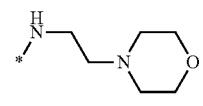 | 61 |
| 2 | Me | H | H | N | H | 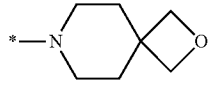 [SMILES: *N1CCC2(CC1)COC2] | 48 |
| 3 | Me | H | H | N | H |  | 15 |
| 4 | Me | H | H | N | H | 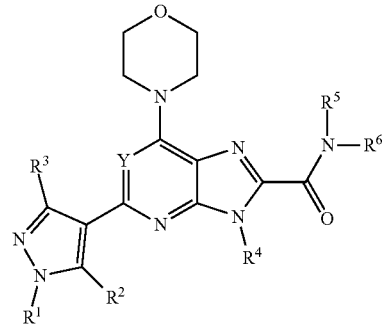 | 27 |

TABLE 3-continued

| Compound No. | R¹ | R² | R³ | Y | R⁴ | —NR⁵R⁶ | PI3Kδ IC₅₀ (nM) |
|---|---|---|---|---|---|---|---|
| 5 | Me | H | H | N | H | (2,6-dimethylmorpholin-4-yl)piperidine | 11 |
| 6 | Me | H | H | N | H | hexahydropyrazino-oxazin-one | 36 |
| 7 | Me | H | H | N | H | 4-(3-oxomorpholin-4-yl)piperidine | 42 |
| 8 | Me | H | Me | N | H | 2-methyl-2-(piperazin-1-yl)propanamide | 10 |
| 9 | Me | H | Me | N | H | 4-(tetrahydropyran-4-yl)piperazine | 9 |
| 10 | Me | H | H | N | H | 2-methyl-2-(piperazin-1-yl)propanamide | 25 |
| 11 | Me | H | H | N | H | 4-(tetrahydropyran-4-yl)piperazine | 26 |
| 12 | Me | H | Me | N | H | 4-(2-hydroxypropan-2-yl)piperidine | 34 |
| 13 | Me | H | H | N | H | 3-morpholinopiperidine | 88 |
| 14 | Me | H | H | N | H | 4-(2-hydroxypropan-2-yl)piperidine | 16 |
| 15 | Me | H | H | N | H | thiomorpholine 1,1-dioxide | 123 |
| 16 | H | Me | Me | N | H | 4-morpholinopiperidine | 88 |
| 17 | Me | H | CF₃ | N | H | 4-morpholinopiperidine | 12 |
| 18 | iPr | H | H | N | H | 4-morpholinopiperidine | 230 |
| 19 | H | H | CF₃ | N | H | 4-morpholinopiperidine | 13 |
| 20 | Me | H | H | N | H | piperazine | 86 |
| 21 | Me | H | H | N | Et | 4-(dimethylamino)piperidine | 313 |
| 22 | Me | H | H | N | Et | 4-morpholinopiperidine | 368 |
| 23 | Me | H | H | N | Me | 4-morpholinopiperidine | 198 |
| 24 | Me | H | H | N | Me | 4-(dimethylamino)piperidine | 271 |
| 25 | Me | H | H | N | H | pyrimidin-2-yl-carbonyl-piperazine | 99 |
| 26 | Me | H | H | N | H | 4-acetamidopiperidine | 101 |
| 27 | Me | H | H | N | H | 1-(pyrimidin-2-yl)piperazine | 128 |
| 28 | Me | H | H | N | H | 4-(methylsulfonamido)piperidine | 69 |
| 29 | Me | H | H | N | H | 1-(pyrazin-2-ylcarbonyl)piperazine | 140 |
| 30 | Me | H | H | N | H | imidazo[1,2-a]pyrazine (tetrahydro) | 627 |
| 31 | Me | H | H | N | H | piperazin-2-one | 465 |
| 32 | Me | H | H | N | H | 1-phenylpiperazine | 56 |
| 33 | Me | H | H | N | H | cyclohexylamine | 366 |

TABLE 3-continued

| Compound No. | R¹ | R² | R³ | Y | R⁴ | —NR⁵R⁶ | PI3 Kδ IC₅₀ (nM) |
|---|---|---|---|---|---|---|---|
| 34 | Me | H | H | N | H | piperazinyl-SO₂Me | 305 |
| 35 | Me | H | H | N | H | 4-phenylpiperidin-1-yl | 17 |
| 36 | Me | H | H | N | H | *NH-CH₂-cyclohexyl | 15 |
| 37 | Me | H | H | N | H | (3R)-3-acetamidopyrrolidin-1-yl | 31 |
| 38 | Me | H | H | N | H | (3R)-3-(methylsulfonamido)pyrrolidin-1-yl | 20 |
| 39 | Me | H | H | N | H | 4-acetylpiperazin-1-yl | 26 |
| 40 | Me | Me | H | N | H | 4-morpholinopiperidin-1-yl | 28 |
| 41 | Me | H | Me | N | H | 4-morpholinopiperidin-1-yl | 14 |
| 42 | H | H | H | N | H | 4-morpholinopiperidin-1-yl | 9 |
| 43 | Me | H | H | N | H | 4-Boc-piperazin-1-yl | 57 |
| 44 | Me | H | H | N | H | (3R)-3-(dimethylamino)pyrrolidin-1-yl | 76 |
| 45 | Me | H | H | N | H | 4-(ethoxycarbonylmethyl)piperazin-1-yl | 48 |
| 46 | Me | H | H | N | H | 4-methylpiperazin-1-yl | 69 |
| 47 | Me | H | H | N | H | *NH-(1-methylpiperidin-4-yl) | 139 |
| 48 | Me | H | H | N | H | *—N(CH₃)₂ | 76 |
| 49 | Me | H | H | N | H | *NH-(1-benzylpiperidin-4-yl) | 62 |
| 50 | Me | H | H | N | H | 4-(carboxymethyl)piperidin-1-yl | 205 |
| 51 | Me | H | H | N | H | 4-(ethoxycarbonylmethyl)piperidin-1-yl | 56 |
| 52 | Me | H | H | N | H | *—NH(CH₂)₂OCH₃ | 231 |
| 53 | Me | H | H | N | H | piperidin-1-yl | 88 |
| 54 | H | H | H | N | H | 4-(dimethylamino)piperidin-1-yl | 31 |
| 55 | nPr | H | H | N | H | 4-(dimethylamino)piperidin-1-yl | 565 |
| 56 | Et | H | H | N | H | 4-(dimethylamino)piperidin-1-yl | 260 |
| 57 | Me | H | H | N | H | 4-(dimethylamino)piperidin-1-yl | 68 |
| 58 | Me | H | H | N | H | 4-morpholinopiperidin-1-yl | 14 |
| 59 | Me | H | H | N | H | N-ethyl-N-(2-morpholinoethyl)amino | 206 |
| 60 | Me | H | H | N | H | N-methyl-N-(2-morpholinoethyl)amino | 159 |
| 61 | Me | H | H | N | Me | *NH-(2-morpholinoethyl) | 80 |
| 62 | Me | H | H | N | H | (3S)-3-hydroxypyrrolidin-1-yl | 61 |
| 63 | Me | H | H | N | H | *NH-(3-morpholinopropyl) | 21 |

TABLE 3-continued
| Compound No. | R¹ | R² | R³ | Y | R⁴ | —NR⁵R⁶ | PI3Kδ IC₅₀ (nM) |
|---|---|---|---|---|---|---|---|
| 64 | Me | H | H | N | H | 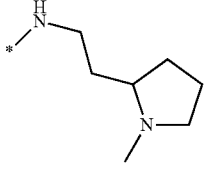 [SMILES: *NCCC1CCCN1C] | 17 |
| 65 | H | H | H | N | H | 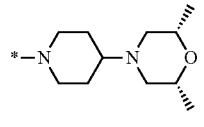 | 12 |
| 66 | H | H | Me | N | H | 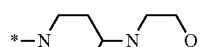 | 21 |
| 67 | Me | H | H | N | Me | 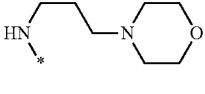 | 11 |
| 68 | Me | H | H | N | H | 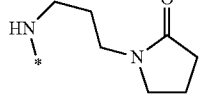 | 17 |
| 69 | Me | H | H | N | H | 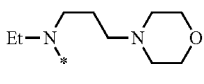 | 61 |
| 70 | Me | H | H | N | H | 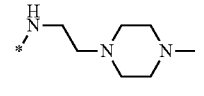 [SMILES: *NCCN1CCN(C)CC1] | 54 |
| 71 | Me | H | Me | N | H | 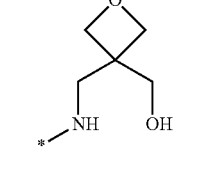 | 30 |
| 72 | H | H | H | N | H |  | 18 |
| 73 | Me | H | H | N | Me | 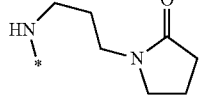 | 60 |
| 74 | H | H | H | N | H | 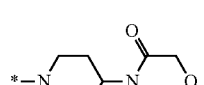 | 8 |
| 75 | Me | H | H | N | H | 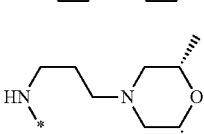 | 18 |
| 76 | Me | H | H | N | H | —NHCH₂C(CH₃)₂CH₂OH | 101 |
| 77 | Me | H | H | CH | H | 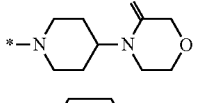 | 9 |
| 78 | Me | H | H | CH | H | 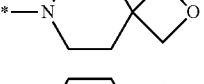 | 13 |
| 79 | Me | H | H | CF | H | 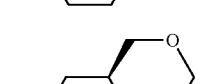 | 20 |
| 80 | Me | H | H | CF | H | 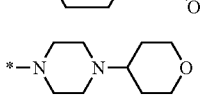 | 194 |
| 81 | Me | H | H | CF | H | 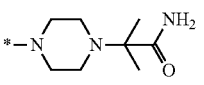 | 7 |
| 82 | Me | H | H | CF | H |  | 11 |
| 83 | Me | H | Me | CF | CH₂Cyp | 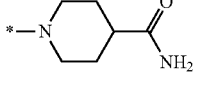 | 92 |
| 84 | Me | H | Me | CF | H | 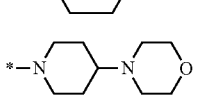 | 5 |
| 85 | Me | H | Me | CF | H | 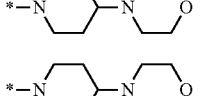 | 19 |
| 86 | Me | H | Me | CF | H | 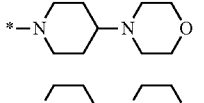 | 27 |
| 87 | Me | H | Me | CF | Me | 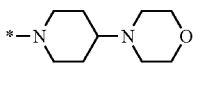 | 3 |
| 88 | Me | Me | Me | CMe | H |  | 365 |
| 89 | Me | H | Me | CMe | H |  | 46 |
| 90 | Me | H | H | CMe | H | | 188 |
| 91 | Me | H | Me | CCl | H | | 31 |
| 92 | Me | H | H | CCl | H | | 163 |
| 93 | Me | Me | Me | CF | H | | 26 |

TABLE 3-continued

| Compound No. | R¹ | R² | R³ | Y | R⁴ | —NR⁵R⁶ | PI3Kδ IC$_{50}$ (nM) |
|---|---|---|---|---|---|---|---|
| 94 | Me | H | Me | CH | H | *-N(piperidine)-N(morpholine) | 4 |
| 95 | Me | Me | H | CF | H | *-N(piperidine)-N(morpholine) | 202 |
| 96 | Me | H | Me | CF | H | *-N(piperidine)-N(morpholine) | 3 |
| 97 | Me | H | Me | CF | H | *-N(piperidine)-N(Me)₂ | 3 |
| 98 | Me | H | H | CF | H | *-N(piperidine)-N(morpholine) | 6 |
| 99 | Me | H | H | CF | H | *-N(piperidine)-N(Me)₂ | 29 |
| 100 | Me | H | H | CH | Me | *-N(piperidine)-N(Me)₂ | 64 |
| 101 | Me | H | H | CH | H | *-N(piperidine)-N(Me)₂ | 41 |
| 102 | Me | H | H | CH | H | *-N(piperidine)-N(morpholine) | 19 |
| 103 | Me | H | H | CH | H | *HN-CH₂CH₂-N(morpholine) | 147 |
| 104 | Me | H | Me | CH | Me | *-N(piperidine)-N(morpholine) | 22 |
| 105 | Me | H | H | CF | H | *HN-CH₂CH₂-N(morpholine) | 32 |
| 106 | Me | H | H | CH | Me | *-N(piperidine)-N(morpholine) | 30 |
| 107 | Me | H | Me | CF | Me | *-N(piperidine)-C(Me)₂OH | 58 |
| 108 | Me | H | H | CF | Me | *-N(piperidine-spiro-oxetane) | 131 |
| 109 | Me | H | H | CH | H | *-N(piperidine)-N(2-Me-morpholine) | 19 |
| 110 | Me | H | H | CH | Me | *-N(piperidine)-N(2,6-diMe-morpholine) | 63 |
| 111 | Me | H | H | CF | Me | *-N(piperidine)-N(morpholine) | 184 |
| 112 | Me | H | Me | CF | Me | *-N(piperidine)-N(2,6-diMe-morpholine) | 15 |
| 113 | Me | H | Me | CH | H | *-N(piperidine)-N(2,6-diMe-morpholine) | 6 |
| 114 | Me | H | Me | CH | Me | *-N(piperidine)-N(2,6-diMe-morpholine) | 72 |
| 115 | Me | H | H | CH | H | HN-CH₂CH₂CH₂-N(morpholine)-* | 16 |
| 116 | Me | H | H | CH | H | HN-CH₂CH₂CH₂-N(2-pyrrolidinone)-* | 19 |
| 117 | Me | H | H | CH | H | *-N(piperidine)-C(Me)₂OH | 122 |
| 118 | H | H | H | CH | H | *-N(piperidine)-N(2,6-diMe-morpholine) | 50 |
| 119 | Me | H | H | CH | H | *-N(azetidine)-N(2,6-diMe-morpholine) | 5 |
| 120 | Me | H | H | CH | H | *-N(azetidine)-N(morpholine) | 10 |

TABLE 3-continued

| Compound No. | R¹ | R² | R³ | Y | R⁴ | —NR⁵R⁶ | PI3Kδ IC₅₀ (nM) |
|---|---|---|---|---|---|---|---|
| 121 | Me | H | H | N | H | 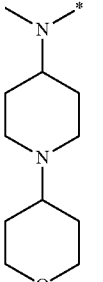 | 52 |
| 122 | Me | H | H | N | H | 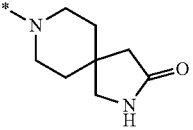 [SMILES: *N1CCC2(CC1)CNC(=O)C2] | 20 |
| 123 | H | H | CF₃ | CF | H | 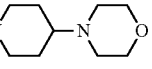 | 4 |
| 124 | Me | H | H | CF | H | 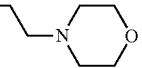 | 17 |
| 125 | H | H | H | CF | H | 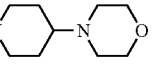 | 43 |
| 126 | Me | H | H | CF | H | 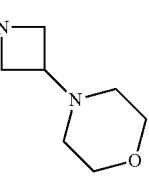 | 25 |
| 127 | Me | H | H | CF | H | 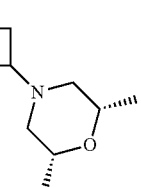 | 36 |
| 128 | Me | H | H | CH | H | 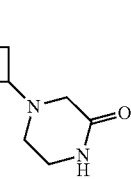 | 19 |
| 129 | Me | H | H | CH | H | 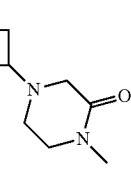 | 10 |
| 130 | Me | H | H | N | H |  | 10 |
| 131 | Me | H | H | CH | Me | 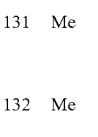 | 146 |
| 132 | Me | H | H | N | Me | 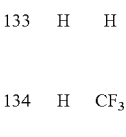 | 240 |
| 133 | H | H | H | CH | H | 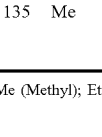 | 19 |
| 134 | H | CF₃ | H | CH | H | 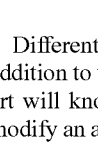 | 3 |
| 135 | Me | H | H | CH | H | 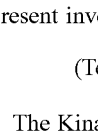 | 19 |

[Me (Methyl); Et (Ethyl); iPr (isopropyl); nPr (n-propyl); Cyp (cyclopropyl)]

BIOLOGICAL EVALUATION

Different assays for PI3K activity can be utilized. In addition to the assays mentioned below, one of skilled in the art will know of other assays that can be utilized and can modify an assay for a particular application. Such assays and modification thereon are within the spirit and scope of the present invention.

(Test Example 1) In Vitro Enzyme Assay

The Kinase-Glo luminescent kinase assay kit (from Promega) was used to measure kinase activity. In this assay, amount of ATP remaining in solution following a kinase reaction is measured. The effect of compounds on PI3Kδ inhibition was carried out by adding 2.29 µg/ml of recombinant PI3K δ enzyme (Proteros, Germany) to reaction mixture containing assay buffer (50 mM HEPES, pH 7.4, 50 mM NaCl, 0.05% CHAPS) supplemented with 10 mM MgCl₂, 5 mM DTT, 60 µM Phosphatidyl inositol bisphosphate (PIP2) and 10 µM ATP in the absence or presence of different concentrations of the compounds in a final volume of 15 µl/well, in a 384 well plate. The reaction mixture was incubated for 2 hours at room temperature. At the end of incubation period the equal volume of Kinase-Glo plus (Promega, V3772), was added per well and the luminescence was measured after incubating for 10 minutes at room temperature in dark. Results were calculated by measuring the luminescence units of test samples to blanks containing no enzyme.

In certain embodiments, the compounds showed IC₅₀ of less than 1000 nM, in another embodiment, the IC₅₀ values range from about 100 nM to 500 nM, and in yet another embodiment, it is even less than 30 nM for PI3Kδ as shown in Table 3 and 4.

The compounds of the present invention were tested for their selectivity for PI3Kδ over PI3Kα, PI3Kβ and PI3Kγ following the above assay using specific recombinant enzymes (Proteros, Germany) for each kinase. Assay condition of kinase assay (PI3Kα, PI3Kβ, PI3Kγ and PI3Kδ) was as follows. Enzyme: 2.29 µg/mL; ATP: 10 µM; PIP2 substrate: 60 µM and Reaction Time: 2 hours.

Abbreviation:
HEPES: 2-[4-(2-hydroxyethyl) piperazin-1-yl] ethanesulfonic acid
CHAPS: 3-[(3-cholamidopropyl) dimethylammonio]-1-propanesulfonate
$MgCl_2$: Magnesium chloride
PIP2: Phosphatidylinositol 4,5-bisphosphate
DTT: Dithiothreitol
ATP: Adenosine triphosphate

TABLE 4

($IC_{50}$ in nM)

| Compound # | PI3Kα | PI3Kβ | PI3Kγ | PI3Kδ | Cell Based |
|---|---|---|---|---|---|
| 3 | >1000 | >10000 | >1000 | 15 | 55 |
| 5 | >1000 | NA | 1184 | 11 | 111 |
| 8 | 6475 | >1000 | 6535 | 10 | 422 |
| 10 | 1206 | >1000 | 251 | 25 | 270 |
| 14 | >1000 | >10000 | 584 | 16 | 810 |
| 19 | 4049 | >10000 | 5665 | 13 | 192 |
| 41 | 8817 | >10000 | 2098 | 14 | 225 |
| 58 | >1000 | >10000 | >1000 | 14 | 6 |
| 64 | 984 | >10000 | 6132 | 17 | 112 |
| 65 | 986 | >10000 | 9768 | 12 | 79 |
| 67 | >1000 | >10000 | >1000 | 11 | 27 |
| 68 | >1000 | >10000 | >1000 | 17 | 296 |
| 72 | >1000 | >10000 | >1000 | 18 | 333 |
| 75 | >1000 | >10000 | >1000 | 18 | 84 |
| 78 | 2191 | >10000 | 640 | 13 | 28 |
| 79 | >1000 | >10000 | >1000 | 20 | 13 |
| 82 | >1000 | >10000 | >1000 | 11 | 346 |
| 85 | >1000 | >10000 | >1000 | 19 | 1273 |
| 86 | >1000 | >10000 | 8459 | 27 | 222 |
| 87 | >10000 | >10000 | >10000 | 3 | 47 |
| 94 | 971 | 9909 | 3026 | 4 | 11 |
| 97 | 1078 | >10000 | 961 | 3 | 183 |
| 98 | >10000 | >10000 | >10000 | 6 | 43 |
| 113 | >1000 | 1154 | >1000 | 6 | 7 |
| 116 | >1000 | >10000 | >1000 | 19 | 72 |

(Test Example 2) Phytohaemagglutinin (PHA)-Induced Interferon (IFN)-Gamma Release in Mouse Splenocytes Effect of compounds on mitogen-induced IFN-γ release in mouse splenocytes was used to evaluate their potency in cell-based assay system [*Blood* (2010) 115: 2203-2213; *Current Protocols in Immunology* (2004) 3.12.1-3.12.20].

Mouse splenocytes were obtained from the spleen of a C57BL/6 mouse and plated at a density of 0.25 million cells/well in a 96 well tissue culture plate. The effect of the compounds to inhibit IFN-γ release was evaluated by treating the splenocytes with various concentrations of the test compounds followed by stimulation with PHA (10 µg/ml) for 48 hours. The IFN-γ release in the cell culture supernatant was quantified by ELISA as per the manufacturer's protocol (BD Biosciences, #555138).

The $IC_{50}$ values of the compounds of the present invention were found to be less than about 1.5 µM, preferably less than about 1 µM, most preferably less than about 0.50. In a preferred embodiment, the $IC_{50}$ values were found to be even less than 0.20. Representative compounds are listed in Table 4, above.

(Test Example 3) Methods for Testing Therapeutic Effect (Test Example 3a) Ovalbumin-Induced Airway Eosinophilia Model in Brown Norway Rats The protocols were followed in similar fashion as described in *Clin. Exp. Immunol.*, 2001; 126:9-15 and *J. Pharmacol. Exp. Ther.*, 2011; 337:145-54. Male Brown Norway rats were sensitized by intraperitoneal injection of a suspension of 1 mg of ovalbumin and 100 mg of aluminum hydroxide (in sterile 0.9% saline) on day 0 and 7. On day 14, the compounds were administered to the rats by oral gavage. One hour after oral administration, the animals were placed into a perspex chamber and exposed to an aerosol of 5% ovalbumin for ten minutes. Compounds were administered on Day 14 and Day 15 either once or twice daily. Forty-eight hours after ovalbumin challenge, the animals were euthanized and bronchoalveolar lavage fluid was collected. The cell suspensions were processed and absolute eosinophil count was enumerated.

In this model, the compounds of the present invention showed efficacy, for example compound nos. 3, 78 and 84 showed $ED_{50}$ of 46, 45 and 26% @ 3 mg/Kg, respectively. The $ED_{50}$ values were found to be less than 3 mg/kg, bid, for example the compound no. 96 was having $ED_{50}$ of 2.5 mg/kg, bid. In a preferred embodiment, the $ED_{50}$ values were even less than 1.5 mg/Kg, bid, for example compound no. 58 and 87 showed $ED_{50}$ of 0.3 mg/Kg, bid and 0.8 mg/Kg, bid, respectively.

(Test Example 3b) House dust mite (HDM) Induced Chronic Asthma Model in Balb/c Mice The protocol was followed as described in *Am. J. Respir. Crit. Care Med.*, 2004; 169: 378-385. Female Balb/c mice were exposed to purified HDM (*Dermatophagoides pteronyssinus*) extract, intranasally (25 µg of protein in 20 µl of saline) for 5 days/week for up to five consecutive weeks. Compounds were administered orally twice daily from week 3 to week 5. Forty-eight hours after last HDM exposure, the animals were euthanized and bronchoalveolar lavage fluid was collected. The cell suspensions were processed and absolute eosinophil count was enumerated.

In this model, the compounds of the present invention were found to be efficacious. The $ED_{50}$ values were found to be less than 2 mg/Kg, bid, for example compound no. 5 and 58 showed $ED_{50}$ of 1.6 mg/Kg, bid and 0.1 mg/Kg, bid, respectively.

(Test Example 4) Method for Testing Oral Bioavailability (BA) in Rats and Mouse (Test Example 4a) Oral Bioavailability (BA) in Rats To Female Wistar rats (210±10 g) test compound was administered as 2.0 mg/mL solution in a vehicle containing polysorbate and dextrose (pH 5.0) by intravenous or as 1.0 mg/mL suspension in methylcellulose for oral route. The final dose was 3.0 mg/kg body weight (intravenous) or 10.0 mg/kg body weight (oral). Plasma samples were analyzed for test compound using LC-MS/MS method. Estimation of pharmacokinetic parameters was done by using moment analysis. WinNonlin software 6.1 (Pharsight) was utilized for the estimation of PK parameters. Oral bioavailability was calculated using dose normalized oral and intravenous plasma exposures. Compounds disclosed herein showed bioavailability amenable for use as oral therapy, for example bioavailability of compound nos. 3, 58 and 97 were 82, 88 and 123, respectively.

(Test Example 4b) Oral Bioavailability (BA) in Mouse

To Male Swiss mouse (23±3 g) test compound was administered as 0.3 mg/mL solution in a vehicle containing polysorbate and dextrose (pH 5.0) by intravenous or as 1.0 mg/mL suspension in methylcellulose for oral route. The final dose was 3.0 mg/kg body weight (intravenous) or 10.0 mg/kg body weight (oral). Plasma samples analyzed for test compound using LC-MS/MS method. Estimation of pharmacokinetic parameters was done by using moment analysis. WinNonlin software 6.1 (Pharsight) was utilized for the estimation of PK parameters. Oral bioavailability was calculated using dose normalized oral and intravenous plasma exposures. Compounds disclosed herein showed bioavailability amenable for use as oral therapy, for example bioavailability of compound nos. 3, 5, 58 and 103 were 73, 116, 100 and 112, respectively.

(Test Example 5) Method of Testing Solubility

A 10 mmol/L solution of the test compound was prepared in DMSO and dispensed 100 μL of 10 mmol/L DMSO stock solutions into labeled glass tubes in duplicate, one for Japanese Pharmacopeia First Fluid (JP1) and second for Japanese Pharmacopeia Second Fluid (JP2). After evaporation of DMSO from each tube, 500 μL of JP1 and JP2 fluid were added in each tube, respectively. These tubes were sonicated for 1 minute and placed on shaker for 30 minutes with an interval of 30 seconds at every 5 minute. Tubes were placed in dark at room temperature for 1 hour and solution was filtered through membrane filter. The filtrate was diluted 2-fold and 10-fold. The resulting test solutions was analyzed and quantified against the standards using UPLC (standard preparation-10 mmol/L solution in DMSO is serially diluted with 50% aqueous acetonitrile solution to prepare 2 solutions; 100 μmol/L standard solution and 5 μmol/L standard solution). The solubility of representative compounds is as shown in Table 5 below.

TABLE 5

| Compound No. | [Solubility, μg/mL] | |
|---|---|---|
| | JP1 | JP2 |
| 5 | 834 | 286 |
| 42 | >1507 | 124 |
| 58 | >1200 | 170 |
| 77 | 1431 | 251 |
| 94 | 808 | 754 |
| 96 | >1024 | 424 |
| 97 | >936 | >923 |
| 99 | 816 | 321 |
| 102 | 932 | 560 |

The invention claimed is:
1. A pyrazole derivative of formula (I)

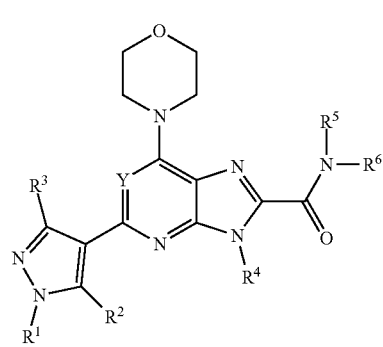

formula (I)

or a pharmaceutically acceptable salt thereof, wherein:
Y represents N, CH, CF, CCl, or $CCH_3$;
$R^1$, $R^2$, and $R^3$ independently represent H, alkyl containing 1 to 3 carbon atoms or halogenated alkyl containing 1 to 3 carbon atoms;
$R^4$ and $R^5$ independently represent H or optionally substituted alkyl containing 1 to 3 carbon atoms; and
$R^6$ represents alkyl, cycloalkyl, or heterocyclyl, wherein alkyl, cycloalkyl and heterocyclyl are optionally substituted; or
$R^5$ and $R^6$ are taken together with nitrogen to which they are attached to form optionally substituted heterocyclyl optionally containing one or more heteroatom(s) selected from N, O, or S.

2. The compound according to claim 1 or a pharmaceutically acceptable salt thereof, wherein:
Y represents N, CH, CF, CCl, or $CCH_3$;
$R^1$, $R^2$, and $R^3$ independently represent H, a ($C_1$-$C_3$)alkyl group or a halogenated ($C_1$-$C_3$)alkyl group;
$R^4$ represents H or a ($C_1$-$C_3$)alkyl group, wherein the ($C_1$-$C_3$)alkyl group is optionally substituted with a ($C_3$-$C_6$)cycloalkyl group;
$R^5$ represents H or a ($C_1$-$C_3$)alkyl group; and
$R^6$ represents a group of formula —X—$R^{6a}$,
wherein X represents a bond or a ($C_1$-$C_3$) alkylenyl group,
$R^{6a}$ represents a ($C_3$-$C_6$)cycloalkyl group or a 4 to 6 membered heterocyclyl group which has optionally 1 to 3 substituents independently selected from the substituent group A, or
$R^5$ and $R^6$ are taken together with nitrogen to which they are attached to form a 4 to 6 membered heterocyclyl ring, or a spiro or fused ring containing 5-7 carbon atoms, and at least one N or O,
wherein the 4 to 6 membered heterocyclyl ring is optionally substituted with a group having the formula —W—$R^{6b}$,
wherein W represents the group consisting of a bond, a ($C_1$-$C_3$)alkylenyl group, —NH—, —CO—, —($C_1$-$C_3$) alkylenyl-CO— or —CO—($C_1$-$C_3$)alkylenyl-,
$R^{6b}$ represents a hydroxy group, a ($C_1$-$C_6$)alkoxy group, an amino group, di($C_1$-$C_3$)alkyl amino group, a ($C_1$-$C_3$)alkylcarbonyl group, a ($C_1$-$C_3$)alkylsulfonyl group, an aryl group, or a 4 to 6 membered heterocyclyl group which optionally has 1 to 3 substituents independently selected from substituent group A,
the substituent group A represents the group consisting of a ($C_1$-$C_3$)alkyl group, an aryl-($C_1$-$C_3$)alkyl group, an oxo group, a hydroxy-($C_1$-$C_3$)alkyl group, and an oxetanyl group.

3. The compound according to claim 1 or a pharmaceutically acceptable salt thereof, wherein Y represents N.

4. The compound according to claim 1 or a pharmaceutically acceptable salt thereof, wherein Y represents CH, CF, CCl, or CCH$_3$.

5. The compound according to claim 1 or a pharmaceutically acceptable salt thereof, wherein $R^1$ represents a methyl group, and $R^2$ and $R^3$ independently represent H or a methyl group.

6. The compound according to claim 1 or a pharmaceutically acceptable salt thereof, wherein $R^4$ represents H or a methyl group.

7. The compound according to claim 1 or a pharmaceutically acceptable salt thereof, wherein $R^5$ and $R^6$ are taken together with nitrogen to which they are attached to form an azetidine ring, a pyrrolidine ring, a piperidine ring or a piperazine ring, wherein the azetidine ring, the pyrrolidine ring, the piperidine ring, and the piperazine ring are optionally substituted with a tetrahydropyranyl group, a morpholinyl group or a 2,6-dimethylmorpholinyl group.

8. The compound according to claim 1 or a pharmaceutically acceptable salt thereof, which is {4-[cis-2,6-Dimethylmorpholin-4-yl]piperidin-1-yl}[2-(1-methyl-1H-pyrazol-4-yl)-6-(morpholin-4-yl)-9H-purin-8-yl]methanone.

9. The compound according to claim 1 or a pharmaceutically acceptable salt thereof, which is [5-(1,3-Dimethyl-1H-pyrazol-4-yl)-6-fluoro-3-methyl-7-(morpholin-4-yl)-3H-imidazo[4,5-b]pyridin-2-yl][4-(morpholin-4-yl)piperidin-1-yl]methanone.

10. The compound according to claim 1 or a pharmaceutically acceptable salt thereof, which is [2-(1-Methyl-1H-pyrazol-4-yl)-6-(morpholin-4-yl)-9H-purin-8-yl][4-(morpholin-4-yl)piperidin-1-yl]methanone.

11. The compound according to claim 1 or a pharmaceutically acceptable salt thereof, which is [5-(1,3-Dimethyl-1H-pyrazol-4-yl)-7-(morpholin-4-yl)-3H-imidazo[4,5-b]pyridin-2-yl][4-(morpholin-4-yl)piperidin-1-yl]methanone.

12. The compound according to claim 1 or a pharmaceutically acceptable salt thereof, which is {4-[cis-2,6-Dimethylmorpholin-4-yl]piperidin-1-yl}[5-(1,3-dimethyl-1H-pyrazol-4-yl)-7-(morpholin-4-yl)-3H-imidazo [4,5-b]pyridin-2-yl]methanone.

13. A pharmaceutical composition comprising a compound according to claim 1 or a pharmaceutically acceptable salt thereof as an active ingredient and one or more pharmaceutically acceptable excipient(s).

14. A method for treating or lessening the severity of a disease or a disorder in a patient, wherein the disease or disorder is selected from allergic asthma, severe asthma, steroid resistant asthma, or COPD, comprising administering to the patient a therapeutically effective amount of a compound according to claim 1 or a pharmaceutically acceptable salt thereof.

* * * * *